US012741161B2

(12) United States Patent
Agarwal et al.

(10) Patent No.: US 12,741,161 B2
(45) **Date of Patent: *Sep. 22, 2026**

(54) METHODS OF USING ULTRASOUND WAVES FOR SONODYNAMIC THERAPY

(71) Applicant: Alpheus Medical, Inc., Chanhassen, MN (US)

(72) Inventors: Vijay Agarwal, New York, NY (US); Braden Eliason, Minneapolis, MN (US); Jeremy Ling, Mendota Heights, MN (US)

(73) Assignee: Alpheus Medical, Inc., Chanhassen, MN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/411,849

(22) Filed: Jan. 12, 2024

(65) Prior Publication Data

US 2024/0207652 A1 Jun. 27, 2024

Related U.S. Application Data

(63) Continuation of application No. 18/214,372, filed on Jun. 26, 2023, now Pat. No. 11,872,414, which is a (Continued)

(51) Int. Cl.
*A61N 7/00* (2006.01)
*A61B 17/00* (2006.01)

(Continued)

(52) U.S. Cl.
CPC .............. *A61N 7/00* (2013.01); *A61F 7/0085* (2013.01); *A61K 9/0053* (2013.01);

(Continued)

(58) Field of Classification Search
CPC ................ A61N 7/00; A61N 2007/003; A61N 2007/006; A61N 2007/0073;

(Continued)

(56) References Cited

U.S. PATENT DOCUMENTS

| | | | |
|---|---|---|---|
| 4,576,177 | A | 3/1986 | Webster |
| 4,735,201 | A | 4/1988 | O'Reilly |
| 4,807,633 | A | 2/1989 | Fry |
| 4,875,487 | A | 10/1989 | Seppi |
| 5,344,974 | A | 9/1994 | Descotes et al. |

(Continued)

FOREIGN PATENT DOCUMENTS

| | | | |
|---|---|---|---|
| CN | 1775327 | A | 5/2006 |
| CN | 101022852 | A | 8/2007 |
| CN | 101228460 | A | 7/2008 |
| CN | 201586334 | U | 9/2010 |

(Continued)

OTHER PUBLICATIONS

Why use random phase driving signal google search.*

(Continued)

*Primary Examiner* — Hien N Nguyen
(74) *Attorney, Agent, or Firm* — KNOBBE, MARTENS, OLSON & BEAR, LLP

(57) ABSTRACT

Disclosed are methods of producing ultrasound waves for providing sonodynamic therapy. The method includes coupling a sonodynamic therapy device with an array of piezoelectric transducer elements to a skin surface. A controller is configured to generate an electrical drive signal to produce ultrasound waves to activate a sonosensitizer in a treatment region without damaging healthy cells in the treatment region.

25 Claims, 30 Drawing Sheets

Related U.S. Application Data continuation of application No. 17/960,443, filed on Oct. 5, 2022, now Pat. No. 11,724,132, which is a continuation of application No. 17/400,011, filed on Aug. 11, 2021, now Pat. No. 11,491,353, which is a continuation of application No. PCT/US2020/017983, filed on Feb. 12, 2020.

(60) Provisional application No. 62/805,186, filed on Feb. 13, 2019.

(51) Int. Cl.

| | |
|---|---|
| ***A61B 17/32*** | (2006.01) |
| ***A61B 18/00*** | (2006.01) |
| ***A61F 7/00*** | (2006.01) |
| ***A61F 7/02*** | (2006.01) |
| ***A61K 9/00*** | (2006.01) |
| ***A61K 31/197*** | (2006.01) |
| ***A61K 41/00*** | (2020.01) |
| ***A61M 21/00*** | (2006.01) |
| ***A61M 21/02*** | (2006.01) |
| ***A61N 7/02*** | (2006.01) |
| ***A61P 35/00*** | (2006.01) |
| ***B06B 1/02*** | (2006.01) |
| ***B06B 1/06*** | (2006.01) |

(52) U.S. Cl.

CPC ........ *A61K 31/197* (2013.01); *A61K 41/0033* (2013.01); *A61K 41/0061* (2013.01); *A61M 21/02* (2013.01); *A61N 7/02* (2013.01); *A61P 35/00* (2018.01); *B06B 1/0207* (2013.01); *B06B 1/0622* (2013.01); *A61B 2017/00084* (2013.01); *A61B 2017/320069* (2017.08); *A61B 2018/00023* (2013.01); *A61B 2018/00446* (2013.01); *A61F 2007/0056* (2013.01); *A61F 2007/0096* (2013.01); *A61F 2007/0288* (2013.01); *A61M 2021/0027* (2013.01); *A61M 2021/005* (2013.01); *A61N 2007/003* (2013.01); *A61N 2007/006* (2013.01); *A61N 2007/0073* (2013.01); *A61N 2007/0078* (2013.01); *A61N 2007/0082* (2013.01); *A61N 2007/0095* (2013.01); *B06B 2201/76* (2013.01)

(58) Field of Classification Search

CPC .... A61N 2007/0078; A61N 2007/0082; A61N 2007/0095; A61F 7/0085; A61F 2007/0056; A61F 2007/0096; A61F 2007/0288; A61K 9/0053; A61K 31/197; A61K 41/0033; A61K 41/0061; A61P 35/00; B06B 1/0207; B06B 1/0622; B06B 2201/76; A61B 2017/00084; A61B 2017/320069; A61B 2018/00023; A61B 2018/00446

See application file for complete search history.

(56) References Cited

U.S. PATENT DOCUMENTS

| | | | |
|---|---|---|---|
| 5,558,092 | A | 9/1996 | Unger et al. |
| 5,733,770 | A | 3/1998 | Watanabe et al. |
| 5,738,635 | A | 4/1998 | Chapelon et al. |
| 5,817,048 | A | 10/1998 | Lawandy |
| 6,176,842 | B1 | 1/2001 | Tachibana et al. |
| 6,379,320 | B1 | 4/2002 | Lafon et al. |
| 6,428,968 | B1 | 8/2002 | Molnar-Kimber et al. |
| 6,498,945 | B1 | 12/2002 | Alheim et al. |
| 6,514,258 | B1 | 2/2003 | Brown et al. |
| 6,572,839 | B2 | 6/2003 | Sugita et al. |
| 6,575,922 | B1 | 6/2003 | Fearnside et al. |
| 6,576,257 | B1 | 6/2003 | Yarmut |
| 6,599,246 | B1 | 7/2003 | Coffey et al. |
| 6,613,005 | B1 | 9/2003 | Friedman et al. |
| 6,622,049 | B2 | 9/2003 | Penner et al. |
| 6,723,750 | B2 | 4/2004 | Voet |
| 6,733,450 | B1 | 5/2004 | Alexandrov et al. |
| 6,739,872 | B1 | 5/2004 | Turri |
| 7,018,395 | B2 | 3/2006 | Chen |
| 7,125,387 | B2 | 10/2006 | Kawabata et al. |
| 7,252,677 | B2 | 8/2007 | Burwell et al. |
| 7,498,029 | B2 | 3/2009 | Hasan et al. |
| 7,514,069 | B2 | 4/2009 | Achileu et al. |
| 7,652,410 | B2 | 1/2010 | Prus |
| 7,674,229 | B2 | 3/2010 | Hynynen et al. |
| 7,699,783 | B2 | 4/2010 | Hanover et al. |
| 7,713,203 | B2 | 5/2010 | Lacoste et al. |
| 7,790,144 | B2 | 9/2010 | Achileu et al. |
| 8,070,682 | B2 | 12/2011 | Zhu |
| 8,123,789 | B2 | 2/2012 | Khanna |
| 8,173,839 | B2 | 5/2012 | Tachiya et al. |
| 8,206,326 | B2 | 6/2012 | Schafer et al. |
| 8,318,133 | B2 | 11/2012 | Achileu et al. |
| 8,318,794 | B2 | 11/2012 | Wang et al. |
| 8,353,853 | B1 | 1/2013 | Kyle et al. |
| 8,409,099 | B2 | 4/2013 | Vitek et al. |
| 8,492,578 | B2 | 7/2013 | Glanzmann et al. |
| 8,548,562 | B2 | 10/2013 | Trachtenberg et al. |
| 8,574,174 | B2 | 11/2013 | Schafer et al. |
| 8,603,014 | B2 | 12/2013 | Alleman et al. |
| 8,613,714 | B2 | 12/2013 | Alleman et al. |
| 8,617,073 | B2 | 12/2013 | Prus et al. |
| 8,718,758 | B2 | 5/2014 | Wagner et al. |
| 8,741,262 | B2 | 6/2014 | Ni et al. |
| 8,747,811 | B2 | 6/2014 | Sharma et al. |
| 8,758,725 | B2 | 6/2014 | Sharma et al. |
| 8,770,203 | B2 | 7/2014 | Bourke, Jr. et al. |
| 8,771,741 | B2 | 7/2014 | Adair et al. |
| 8,932,237 | B2 | 1/2015 | Vitek et al. |
| 8,977,354 | B2 | 3/2015 | Wagner et al. |
| 8,979,775 | B2 | 3/2015 | Schafer et al. |
| 8,992,958 | B2 | 3/2015 | Kanehira et al. |
| 9,012,502 | B2 | 4/2015 | Chibazakura et al. |
| 9,023,090 | B2 | 5/2015 | Palti |
| 9,072,774 | B2 | 7/2015 | Zheng et al. |
| 9,220,718 | B2 | 12/2015 | Park et al. |
| 9,249,086 | B2 | 2/2016 | Braenden et al. |
| 9,313,423 | B2 | 4/2016 | Wang et al. |
| 9,326,964 | B2 | 5/2016 | Stensrud |
| 9,371,555 | B2 | 6/2016 | Roberts |
| 9,463,256 | B2 | 10/2016 | Lub et al. |
| 9,475,028 | B2 | 10/2016 | Krishna et al. |
| 9,492,121 | B2 | 11/2016 | Andrews et al. |
| 9,492,681 | B2 | 11/2016 | Aydt et al. |
| 9,493,810 | B2 | 11/2016 | Ezrin |
| 9,498,650 | B2 | 11/2016 | Schafer et al. |
| 9,510,909 | B2 | 12/2016 | Grant et al. |
| 9,572,880 | B2 | 2/2017 | Harris et al. |
| 9,764,029 | B2 | 9/2017 | Shibaguchi et al. |
| 9,816,118 | B2 | 11/2017 | Lee et al. |
| 9,833,634 | B2 | 12/2017 | Bourke et al. |
| 9,963,724 | B2 | 5/2018 | Saito et al. |
| 9,974,974 | B2 | 5/2018 | Groseth |
| 9,999,760 | B2 | 6/2018 | Fang |
| 10,035,027 | B2 | 7/2018 | Deisseroth et al. |
| 10,098,539 | B2 | 10/2018 | Konofagou et al. |
| 10,265,234 | B1 | 4/2019 | Zwierstra et al. |
| 10,272,008 | B2 | 4/2019 | Zwierstra et al. |
| 10,286,091 | B2 | 5/2019 | Desgranges et al. |
| 10,456,603 | B2 | 10/2019 | Tlusty et al. |
| 10,493,296 | B2 | 12/2019 | Vo-Dinh et al. |
| 10,512,691 | B2 | 12/2019 | Kalifa et al. |
| 10,555,861 | B2 | 2/2020 | Zwierstra et al. |
| 10,589,129 | B2 | 3/2020 | Vortman et al. |
| 10,653,653 | B2 | 5/2020 | Zhao et al. |
| 10,675,482 | B2 | 6/2020 | Agarwal |
| 10,702,244 | B2 | 7/2020 | O'Reilly et al. |
| 10,765,892 | B1 | 9/2020 | Vitek et al. |

(56) References Cited

U.S. PATENT DOCUMENTS

| | | | | |
|---|---|---|---|---|
| 10,773,098 | B2 | 9/2020 | Liu et al. | |
| 10,835,756 | B2 | 11/2020 | Bourke, Jr. et al. | |
| 10,918,718 | B2 | 2/2021 | Mo et al. | |
| 10,974,077 | B2 | 4/2021 | Guha et al. | |
| 11,040,101 | B2 | 6/2021 | Nomikou | |
| 11,071,522 | B2 | 7/2021 | Hynynen et al. | |
| 11,305,133 | B2 | 4/2022 | Khuri-Yakub et al. | |
| 11,307,204 | B2 | 4/2022 | Ezrin | |
| 11,318,332 | B2 | 5/2022 | Agarwal et al. | |
| 11,344,498 | B2 | 5/2022 | Rwei et al. | |
| 11,382,987 | B2 | 7/2022 | Callan et al. | |
| 11,389,395 | B2 | 7/2022 | Wrenn et al. | |
| 11,491,353 | B2 | 11/2022 | Agarwal et al. | |
| 11,504,290 | B2 | 11/2022 | Hewes et al. | |
| 11,534,630 | B2 | 12/2022 | Ramamurthy | |
| 11,559,585 | B2 | 1/2023 | Li et al. | |
| 11,607,197 | B2 | 3/2023 | Muller et al. | |
| 11,617,904 | B2 | 4/2023 | Agarwal et al. | |
| 11,639,360 | B2 | 5/2023 | Fan et al. | |
| 11,660,068 | B2 | 5/2023 | Kim et al. | |
| 11,660,342 | B2 | 5/2023 | Kim et al. | |
| 11,691,033 | B2 | 7/2023 | Sverdlik et al. | |
| 11,712,473 | B2 | 8/2023 | Callan et al. | |
| 11,724,132 | B2 | 8/2023 | Agarwal et al. | |
| 11,730,980 | B2 | 8/2023 | Agarwal et al. | |
| 11,771,370 | B2 | 10/2023 | Hynynen | |
| 11,793,490 | B2 | 10/2023 | Hynynen et al. | |
| 11,793,983 | B2 | 10/2023 | Chen et al. | |
| 11,794,040 | B2 | 10/2023 | Capelli | |
| 11,813,330 | B2 | 11/2023 | Mandel et al. | |
| 11,826,288 | B2 | 11/2023 | Hewes et al. | |
| 11,857,812 | B2 | 1/2024 | Ramamurthy | |
| 11,865,371 | B2 | 1/2024 | Capelli | |
| 11,865,372 | B2 | 1/2024 | Agarwal et al. | |
| 11,872,413 | B2 | 1/2024 | Carpentier et al. | |
| 11,878,059 | B2 | 1/2024 | Callan et al. | |
| 11,957,936 | B2 | 4/2024 | Yan et al. | |
| 11,975,156 | B2 | 5/2024 | Agarwal et al. | |
| 11,980,777 | B2 | 5/2024 | Agarwal et al. | |
| 11,998,395 | B2 | 6/2024 | Specht et al. | |
| 12,011,482 | B2 | 6/2024 | Zhao et al. | |
| 12,017,093 | B2 | 6/2024 | Ramamurthy et al. | |
| 12,097,392 | B2 | 9/2024 | Agarwal et al. | |
| 12,103,941 | B2 | 10/2024 | Zhu et al. | |
| 12,168,055 | B2 | 12/2024 | Marcus | |
| 12,201,643 | B2 | 1/2025 | Li et al. | |
| 12,290,403 | B2 | 5/2025 | Hynynen et al. | |
| 12,303,722 | B2 | 5/2025 | Zhang et al. | |
| 12,329,566 | B2 | 6/2025 | Kubanek | |
| 12,397,179 | B2 | 8/2025 | Noh et al. | |
| 12,403,333 | B2 | 9/2025 | Ramamurthy et al. | |
| 12,426,836 | B2 | 9/2025 | Hynynen | |
| 12,433,569 | B2 | 10/2025 | Ramamurthy et al. | |
| 2001/0041163 | A1 | 11/2001 | Sugita et al. | |
| 2002/0038086 | A1 | 3/2002 | Hynynen et al. | |
| 2003/0069526 | A1 | 4/2003 | Thopson et al. | |
| 2003/0092667 | A1 | 5/2003 | Tachibana et al. | |
| 2003/0114434 | A1 | 6/2003 | Chen et al. | |
| 2004/0002677 | A1 | 1/2004 | Gentsler | |
| 2004/0049134 | A1 | 3/2004 | Tosaya et al. | |
| 2004/0054282 | A1 | 3/2004 | Aubry et al. | |
| 2004/0171601 | A1 | 9/2004 | Fukumura et al. | |
| 2004/0210135 | A1 | 10/2004 | Hynynen et al. | |
| 2005/0060012 | A1 | 3/2005 | Voorhees et al. | |
| 2005/0085726 | A1 | 4/2005 | Lacoste et al. | |
| 2005/0118550 | A1 | 6/2005 | Turri | |
| 2005/0124897 | A1 | 6/2005 | Chopra | |
| 2005/0197577 | A1 | 9/2005 | Makin et al. | |
| 2005/0240124 | A1 | 10/2005 | Mast et al. | |
| 2005/0277824 | A1 | 12/2005 | Aubry et al. | |
| 2006/0058661 | A1* | 3/2006 | Hirama | A61B 8/14 600/437 |
| 2006/0241530 | A1 | 10/2006 | Ostrovsky et al. | |
| 2007/0005121 | A1 | 1/2007 | Khanna | |
| 2007/0038099 | A1 | 2/2007 | Sugita et al. | |
| 2007/0112344 | A1 | 5/2007 | Keilman et al. | |
| 2007/0260295 | A1 | 11/2007 | Chen et al. | |
| 2008/0194954 | A1 | 8/2008 | Unger et al. | |
| 2008/0319375 | A1 | 12/2008 | Hardy | |
| 2009/0049907 | A1 | 2/2009 | Wu et al. | |
| 2009/0062724 | A1 | 3/2009 | Chen | |
| 2009/0099483 | A1 | 4/2009 | Rybyanets | |
| 2010/0069746 | A1 | 3/2010 | St. John | |
| 2010/0106229 | A1 | 4/2010 | Gammons et al. | |
| 2010/0217160 | A1 | 8/2010 | Saguchi et al. | |
| 2010/0228523 | A1 | 9/2010 | Kajitani et al. | |
| 2010/0262115 | A1 | 10/2010 | Madiyalakan et al. | |
| 2011/0020429 | A1 | 1/2011 | Lauten et al. | |
| 2011/0263967 | A1 | 10/2011 | Bailey et al. | |
| 2012/0016429 | A1 | 1/2012 | Klorg | |
| 2012/0040312 | A1 | 2/2012 | Hinders | |
| 2012/0065494 | A1 | 3/2012 | Gertner et al. | |
| 2012/0089205 | A1 | 4/2012 | Boyden et al. | |
| 2012/0209150 | A1 | 8/2012 | Zeng et al. | |
| 2012/0271167 | A1 | 10/2012 | Holland et al. | |
| 2012/0283605 | A1 | 11/2012 | Lewis, Jr. | |
| 2013/0101468 | A1 | 4/2013 | Boutin et al. | |
| 2013/0172739 | A1 | 7/2013 | Paladini | |
| 2013/0281890 | A1 | 10/2013 | Mishelevich | |
| 2014/0257262 | A1 | 9/2014 | Carpentier et al. | |
| 2014/0316269 | A1 | 10/2014 | Zhang et al. | |
| 2014/0316387 | A1 | 10/2014 | Harris et al. | |
| 2015/0126910 | A1 | 5/2015 | Koskela et al. | |
| 2015/0224345 | A1 | 8/2015 | Warlick | |
| 2015/0320591 | A1 | 11/2015 | Smith et al. | |
| 2016/0151618 | A1 | 6/2016 | Powers et al. | |
| 2016/0157964 | A1 | 6/2016 | Suttin et al. | |
| 2016/0243381 | A1 | 8/2016 | Alford et al. | |
| 2016/0325110 | A1 | 11/2016 | Agarwal et al. | |
| 2017/0007699 | A1 | 1/2017 | Park et al. | |
| 2017/0095557 | A1 | 4/2017 | Fang | |
| 2017/0173351 | A1 | 6/2017 | Agarwal et al. | |
| 2018/0001114 | A1 | 1/2018 | Li et al. | |
| 2018/0049762 | A1 | 2/2018 | Seip et al. | |
| 2018/0177491 | A1 | 6/2018 | Hynynen et al. | |
| 2018/0207447 | A1 | 7/2018 | Liu | |
| 2018/0236270 | A1 | 8/2018 | Hananel et al. | |
| 2018/0296859 | A1 | 10/2018 | Guha et al. | |
| 2018/0344849 | A1 | 12/2018 | Trouard et al. | |
| 2018/0344872 | A1 | 12/2018 | Callan et al. | |
| 2019/0009111 | A1 | 1/2019 | Myhr et al. | |
| 2019/0021666 | A1 | 1/2019 | Hynynen | |
| 2019/0030375 | A1 | 1/2019 | Zachar | |
| 2019/0069949 | A1 | 3/2019 | Vrba et al. | |
| 2019/0070296 | A1 | 3/2019 | Wang et al. | |
| 2019/0105517 | A1 | 4/2019 | Tyler | |
| 2019/0175433 | A1 | 6/2019 | Zwierstra et al. | |
| 2019/0183457 | A1 | 6/2019 | Ramamurthy | |
| 2019/0184204 | A1 | 6/2019 | Ramamurthy | |
| 2019/0307472 | A1 | 10/2019 | Lu et al. | |
| 2019/0339387 | A1 | 11/2019 | Pang et al. | |
| 2019/0344099 | A1 | 11/2019 | Tlusty et al. | |
| 2020/0124607 | A1 | 4/2020 | Ezrin | |
| 2020/0139161 | A1 | 5/2020 | Gomori | |
| 2020/0146917 | A1 | 5/2020 | Zwierstra et al. | |
| 2020/0197659 | A1 | 6/2020 | Wilcox et al. | |
| 2020/0282196 | A1 | 9/2020 | Chen et al. | |
| 2021/0008385 | A1 | 1/2021 | Agarwal et al. | |
| 2021/0106849 | A1 | 4/2021 | Liu et al. | |
| 2021/0177759 | A1 | 6/2021 | Sosnik et al. | |
| 2021/0236862 | A1 | 8/2021 | Eliason | |
| 2021/0251599 | A1 | 8/2021 | Torp et al. | |
| 2021/0260411 | A1 | 8/2021 | Khuri-Yakub et al. | |
| 2021/0330294 | A1 | 10/2021 | Hynynen et al. | |
| 2021/0369843 | A1 | 12/2021 | Agarwal et al. | |
| 2021/0370102 | A1 | 12/2021 | Agarwal et al. | |
| 2021/0370103 | A1 | 12/2021 | Agarwal et al. | |
| 2022/0062417 | A1 | 3/2022 | Callan et al. | |
| 2022/0072128 | A1 | 3/2022 | Airan | |
| 2022/0126120 | A1 | 4/2022 | Zachar | |
| 2022/0175357 | A1 | 6/2022 | Ding et al. | |
| 2022/0175926 | A1 | 6/2022 | Karp et al. | |
| 2022/0184234 | A1 | 6/2022 | Marcus | |
| 2022/0226471 | A1 | 7/2022 | Marcus | |

(56) References Cited

U.S. PATENT DOCUMENTS

| | | | |
|---|---|---|---|
| 2022/0233695 | A1 | 7/2022 | Yoo et al. |
| 2022/0257214 | A1 | 8/2022 | Anquez et al. |
| 2022/0257984 | A1 | 8/2022 | Agarwal et al. |
| 2022/0266063 | A1 | 8/2022 | Emery et al. |
| 2022/0347314 | A1 | 11/2022 | Callan et al. |
| 2022/0370609 | A1 | 11/2022 | Park et al. |
| 2022/0378692 | A1 | 12/2022 | Sontum et al. |
| 2023/0037342 | A1 | 2/2023 | Agarwal et al. |
| 2023/0041402 | A1 | 2/2023 | Tsuboi |
| 2023/0201553 | A1 | 6/2023 | Levy et al. |
| 2023/0225748 | A1 | 7/2023 | Hassan et al. |
| 2023/0226379 | A1 | 7/2023 | Agarwal et al. |
| 2023/0277877 | A1 | 9/2023 | Agarwal et al. |
| 2023/0293913 | A1 | 9/2023 | Achrol et al. |
| 2023/0330441 | A1 | 10/2023 | Agarwal et al. |
| 2023/0330442 | A1 | 10/2023 | Agarwal et al. |
| 2023/0330443 | A1 | 10/2023 | Agarwal et al. |
| 2023/0338751 | A1 | 10/2023 | Agarwal et al. |
| 2023/0338752 | A1 | 10/2023 | Agarwal et al. |
| 2023/0338753 | A1 | 10/2023 | Agarwal et al. |
| 2023/0338754 | A1 | 10/2023 | Agarwal et al. |
| 2024/0024649 | A1 | 1/2024 | Agarwal et al. |
| 2024/0041429 | A1 | 2/2024 | Hynynen et al. |
| 2024/0042043 | A1 | 2/2024 | Kim et al. |
| 2024/0042242 | A1 | 2/2024 | Ramamurthy et al. |
| 2024/0050774 | A1 | 2/2024 | Capelli |
| 2024/0057967 | A1 | 2/2024 | Treeby et al. |
| 2024/0057971 | A1 | 2/2024 | Chiang et al. |
| 2024/0091363 | A1 | 3/2024 | Callan et al. |
| 2024/0091564 | A1 | 3/2024 | Capelli |
| 2024/0091758 | A1 | 3/2024 | Kwan et al. |
| 2024/0108917 | A1 | 4/2024 | Agarwal et al. |
| 2024/0131071 | A1 | 4/2024 | Heimberger |
| 2024/0156745 | A1 | 5/2024 | Alphandery |
| 2024/0189427 | A1 | 6/2024 | Marcus |
| 2024/0198139 | A1 | 6/2024 | Sverdlik et al. |
| 2024/0216549 | A1 | 7/2024 | Sontum et al. |
| 2024/0269287 | A1 | 8/2024 | Khorsandi et al. |
| 2024/0269489 | A1 | 8/2024 | Kvale et al. |
| 2024/0278041 | A1 | 8/2024 | Agarwal et al. |
| 2024/0293683 | A1 | 9/2024 | Agarwal et al. |
| 2024/0335680 | A1 | 10/2024 | Achrol et al. |
| 2024/0342510 | A1 | 10/2024 | Hacker et al. |
| 2024/0423904 | A1 | 12/2024 | Robb et al. |
| 2025/0001219 | A1 | 1/2025 | Noh et al. |
| 2025/0032822 | A1 | 1/2025 | Sato et al. |
| 2025/0041577 | A1 | 2/2025 | Shapira et al. |
| 2025/0073504 | A1 | 3/2025 | Daft et al. |
| 2025/0099589 | A1 | 3/2025 | Wang et al. |
| 2025/0108237 | A1 | 4/2025 | Sato et al. |
| 2025/0114582 | A1 | 4/2025 | Canney et al. |
| 2025/0121216 | A1 | 4/2025 | Murphy et al. |
| 2025/0121219 | A1 | 4/2025 | Daft et al. |
| 2025/0177557 | A1 | 6/2025 | Keenan |
| 2025/0186343 | A1 | 6/2025 | Urbach et al. |
| 2025/0222281 | A1 | 7/2025 | Satir et al. |

FOREIGN PATENT DOCUMENTS

| | | | |
|---|---|---|---|
| CN | 102233159 | A | 11/2011 |
| CN | 102885648 | A | 1/2013 |
| CN | 104519960 | A | 4/2015 |
| CN | 107864633 | A | 8/2018 |
| CN | 211536251 | U | 9/2020 |
| EP | 1909908 | B1 | 3/2011 |
| EP | 2318086 | B1 | 4/2016 |
| EP | 3359134 | B1 | 10/2016 |
| EP | 2931290 | B1 | 8/2018 |
| EP | 3298066 | B1 | 8/2019 |
| EP | 3060255 | B1 | 12/2019 |
| EP | 3554378 | B1 | 7/2021 |
| EP | 3558457 | B1 | 11/2021 |
| EP | 3374024 | B1 | 7/2022 |
| EP | 2726152 | B1 | 8/2022 |
| EP | 3597111 | B1 | 5/2023 |
| EP | 4241763 | | 9/2023 |
| EP | 3229906 | B1 | 11/2023 |
| EP | 3924046 | B1 | 11/2023 |
| EP | 3419548 | B1 | 7/2024 |
| EP | 3487410 | B1 | 2/2025 |
| EP | 3890781 | B1 | 10/2025 |
| JP | S60-053131 | A | 3/1985 |
| JP | S62-087151 | | 4/1987 |
| JP | S62-202813 | U | 12/1987 |
| JP | H07-231894 | | 9/1995 |
| JP | H09-122164 | | 5/1997 |
| JP | 2001-104355 | | 4/2001 |
| JP | 2003503103 | A | 1/2003 |
| JP | 2005125075 | A | 5/2005 |
| JP | 2005152093 | A | 6/2005 |
| JP | 2005-537071 | | 12/2005 |
| JP | 2007-007279 | | 1/2007 |
| JP | 2008-188160 | | 8/2008 |
| JP | 4492818 | B | 6/2010 |
| JP | 2011509737 | A | 3/2011 |
| JP | 2013-512016 | A | 4/2013 |
| JP | 2015-517350 | | 6/2015 |
| KR | 100796450 | B1 | 1/2008 |
| KR | 20100027584 | | 3/2010 |
| WO | WO 92/10142 | A1 | 6/1992 |
| WO | WO 95/05214 | A1 | 2/1995 |
| WO | WO 96/28200 | A1 | 9/1996 |
| WO | WO 2009/026724 | A1 | 3/2009 |
| WO | WO 2009/095912 | A1 | 8/2009 |
| WO | WO 2010/078929 | A1 | 7/2010 |
| WO | WO 2011/057028 | | 5/2011 |
| WO | WO 2012/035747 | A1 | 3/2012 |
| WO | WO 2013/170223 | | 11/2013 |
| WO | WO 2014/083614 | | 6/2014 |
| WO | WO 2015/03484 | A1 | 7/2015 |
| WO | WO 2017/074509 | | 5/2017 |
| WO | WO 2018026738 | A1 | 2/2018 |
| WO | WO 2018035256 | A1 | 2/2018 |
| WO | WO 2018/112664 | A1 | 6/2018 |
| WO | WO 2019059027 | A1 | 3/2019 |
| WO | WO 2019/123411 | | 6/2019 |
| WO | WO 2019/205285 | | 10/2019 |
| WO | WO 2020/033764 | A1 | 2/2020 |
| WO | WO 2020/167922 | | 8/2020 |
| WO | WO 2020/167992 | A1 | 8/2020 |
| WO | WO 2020/217472 | A1 | 10/2020 |
| WO | WO 2020/243319 | A1 | 12/2020 |
| WO | WO 2021154730 | A1 | 8/2021 |
| WO | WO 2022/032283 | A1 | 2/2022 |
| WO | WO 2022/115695 | | 6/2022 |
| WO | WO 2023/105290 | | 6/2023 |
| WO | WO 2023/170231 | | 9/2023 |
| WO | WO 2023/178964 | | 9/2023 |
| WO | WO 2023/230246 | A1 | 11/2023 |
| WO | WO 2023/233475 | | 12/2023 |
| WO | WO 2023/240256 | | 12/2023 |
| WO | WO 2024/076537 | | 4/2024 |
| WO | WO 2024/211443 | A1 | 4/2024 |
| WO | WO 2024/148416 | | 7/2024 |
| WO | WO 2024/209347 | A1 | 10/2024 |
| WO | WO 2024/233948 | A1 | 11/2024 |
| WO | WO 2024/239160 | A1 | 11/2024 |
| WO | WO 2024/257021 | A1 | 12/2024 |
| WO | WO 2025/013486 | A1 | 1/2025 |
| WO | WO 2025/025574 | A1 | 2/2025 |
| WO | WO 2025/085439 | A1 | 4/2025 |
| WO | WO 2025/103733 | A1 | 5/2025 |
| WO | WO 2025/122626 | A1 | 6/2025 |
| WO | WO 2025/129148 | A1 | 6/2025 |
| WO | WO 2025/141545 | A1 | 7/2025 |
| WO | WO 2025/163636 | A1 | 8/2025 |

OTHER PUBLICATIONS

Fisher et al., "ALA-Pp IX mediated photodynamic therapy of malignant gliomas augmented by hypothermia," PLoS One Jul. 2017. 31 ;12(7): e0181654. PMID: 28759636. (Year: 2017).

(56) References Cited

OTHER PUBLICATIONS

Hynynen et al. "Pre-clinical testing of a phased array ultrasound system for MRI-guided noninvasive surgery of the brain-A primate study", Apr. 7, 2006, European Journal of Radiology, pp. 149-156.

Jain et al., "Ultrasound-based triggered drug delivery to tumors", Drug Delivery and Translational Search, Springer, Germany, vol. 8, No. 1, Dec. 4, 2017.

Kinoshita et al., Mechanism of Porphyrin-Induced Sonodynamic Effect: Possible Role of Hyperthermia, Radiation Research 165, pp. 229-306, 2006.

Li et al., "Cytotoxic Effect of Protoporphyrin IX to Human Leukemia U937 Cells under Ultrasonic Irradiation", Apr. 15, 2014, pp. 1186-1196 (Year: 2014).

McDannold et al., "Transcranial Magnetic Resonance Imaging-Guided Focused Ultrasound Surgery of Brain Tumors: Initial Findings in 3 Patients", Feb. 2010, Neurosurgery, vol. 66 No. 2, pp. 323-332.

Nonaka et al. "Sonodynamic therapy consisting of focused ultrasound and photosensitizer causes a selective antitumor effect in a rat intracranial glioma model", Anticancer Res 29: 943-950, 2009 (Year: 2009).

Ohmura et al., "Sonodynamic therapy with 5-aminolevulinic acid and focused ultrasound for deep-seated intracranial glioma in rat," Anticancer Res. Jul. 2011.;31(7):2527-33. PMID: 21873170. (Year: 2011).

Song et al., "Overview of therapeutic hypothermia," Curr. Treat. Options. Neural. Dec. 2012; 14(6):541-8. PMID: 23007950. (Year: 2012).

Tetard et al., "Experimental use of photodynamic therapy in high grade gliomas: A revie focused on 5-aminolevulinic acid", Photodiagnosis and Photodynamic Therapy, vol. 11, No. 3, Sep. 1, 2014, pp. 319-330.

Umemura et al., "Recent advances in sonodynamic approach to cancer therapy" 1996, Ultrasonics Sonochemistry, pp. S187-S191.

Wang et al., "Study of cell killing effect on S180 by ultrasound activating protoporphyrin IX", Nov. 7, 2007 Ultrasonics, pp. 135-140.

Wood et al. "A Review of Low-Intensity Ultrasound for Cancer Therapy" Ultrasound in Med. & Biol., vol. 41, No. 4, pp. 905-928, 2015.

Yumita et al. "Sonodynamically induced antitumor effect of Photofrin II on colon 26 carcinoma." J Cancer Res Clin Oneal 126: 601-606, 2000 (Year: 2000).

International Search Report and Written Opinion for International PCT Application No. PCT/US2020/017983, dated Jun. 15, 2020 (6WO).

Galkin, "The Use of Transcranial Focused Ultrasound in CNS Diseases", Jan. 2016, Problems of Neurosurgery, pp. 1-108 (Year: 2016).

Hendee et al., "Medical Imaging Physics, Fourth Edition", 2002, pp. 303-353 (Year: 2002).

J. Chen, S. LeBlang, A. Hananel, R. Aginsky, J. Perez, M. Gofeld, Y. Shir & J. F. Aubry (2020) An incoherent HIFU transducer for treatment of the medial branch nerve: Numerical study and in vivo validation, International Journal of Hyperthermia, 37: 1, 1219-1228, DOI: 10.1080/02656736.2020.1828628 (Year: 2020).

Olympus Corporation, "Ultrasonic Transducers", 2010 (Year: 2010).

Serpe et al., "Sonodynamic antimicrobial chemotherapy: First steps towards a sound approach for microbe inactivation", Journal of Photochemistry and Photobiology B: Biology, vol. 150, Sep. 2015, pp. 44-49 (Year: 2015).

Wang et al., "Rapid and selective cerebral hypothermia achieved using a cooling helmet," J. Neurosurg. 2004; 100(2):272-77. PMI D: 15086235. (Year: 2004).

Xu et al., "Protoporphyrin IX Induces a Necrotic Cell Death in Human TH P-1 Macrophages through Activation of Reactive Oxygen" Species/c-Jun N-Terminal Protein Kinase, 2014, Cellular Physiology and Biochemistry (Year: 2014).

Chen et al., "Combination of sonodynamic with temozolomide inhibits C6 glioma migration and promotes mitrochondrial pathway apoptosis via suppressing NHE-1 expression", Ultrasonics Sonochemistry, Butterworth-Heinmann, GB, vol. 39, May 17, 2017 (May 17, 2017), pp. 654-661.

Hand et al., "A random phased array device for delivery of high intensity focused ultrasound", Physics in Medicine and Biology, 54(19), pp. 5675-5693, 2009.

Kast R, Salacz M. DIPG-30. A New Treatment Opportunity for Dipg: 5-ALA and Sonodynamic Augmented meV Irradiation, The Asai Protocol. Neuro Oncol. Jun. 2018;20(Suppl 2):55. doi: 10.1093/neuonc/noy059.123. Epub Jun. 22, 2018. PMCID: PMC6012850.

Wu, SK., Santos, M.A., Marcus, S.L et al. MR-guided Focused Ultrasound Facilitates Sonodynamic Therapy with 5-Aminolevulinic Acid in a Rat Glioma Model. Sci Rep 9, 10465 (2019). https://doi.org/10.1038/s41598-019-46832-2.

C. Adams et al., "Implementation of a Skull-Conformal Phased Array for Transcranial Focused Ultrasound Therapy," (in eng), IEEE Trans Biomed Eng, vol. 68, No. 11 , pp. 3457-3468, Nov. 2021 , doi: 10.1109/tbme.2021 .3077802.

* cited by examiner

METHODS OF USING ULTRASOUND WAVES FOR SONODYNAMIC THERAPY

CROSS-REFERENCE TO RELATED APPLICATIONS

This application is a continuation of U.S. patent application Ser. No. 18/214,372, filed Jun. 26, 2023, which is a continuation of U.S. patent application Ser. No. 17/960,443, filed Oct. 5, 2022, which is a continuation of U.S. patent application Ser. No. 17/400,011, filed Aug. 11, 2021, which is a continuation of PCT Application No. PCT/US2020/017983, filed Feb. 12, 2020, and titled NON-INVASIVE SONODYNAMIC THERAPY, which claims priority under 35 U.S.C. § 119 to U.S. Provisional Patent Application No. 62/805,186, filed, Feb. 13, 2019, and titled NON-INVASIVE SONODYNAMIC THERAPY, each of which is hereby incorporated by reference herein in its entirety.

FIELD

This disclosure relates to a broadly applicable technology platform for treating lesions using sonodynamic therapy. More particularly, this disclosure relates to devices, systems, and methods for treating tumors and cancer in body parts using sonodynamic therapy.

BACKGROUND

Sonodynamic therapy is a proposed form of treatment using drugs that only become cytotoxic upon exposure to ultrasound. Since ultrasound can be focused into small tissue volumes within the body, this method provides a potential means of localizing treatment and reducing the risk of side effects elsewhere in the body. In this respect it is similar to photodynamic therapy, which uses light for drug activation, and there are several drugs that have been shown to be sensitive to both light and sound. A potential key advantage of sonodynamic over photodynamic therapy is the much greater tissue depth that can be reached non-invasively by ultrasound compared to light.

The drug is a sonosensitizing agent (i.e., sonosensitizer) that preferentially accumulates in the cells of the lesions. Sonosensitizers initiate a cytotoxic response in target tissues when exposed to ultrasonic energy. Upon activation by the ultrasonic energy, sonodynamic therapy drugs or "sonosensitisers" produce reactive oxygen species (ROS) that generate the cytotoxic effect. The detailed mechanisms of ROS production are not fully understood but several studies have indicated that acoustic cavitation and the associated thermal, chemical or luminescence phenomena may be involved. They can be used alone or in concert with other sonosensitizers, many of which are approved by the Food and Drug Administration (FDA) for use in neurosurgical diagnostic imaging or treatment of tumors throughout the body.

The promise of sonodynamic therapy is the ability to treat a lesion, such as a region in an organ or tissue which has suffered damage through injury or disease, such as a wound, ulcer, abscess, or tumor, with levels of ultrasound that are safe for healthy tissue yet lethal to cells within the lesion harboring a sonosensitizer.

In a contemplated minimally invasive sonodynamic process, lesions could be treated directly with a catheter placed in situ using a relatively simple procedure mimicking a biopsy. Getting an acoustic wave to be consistent and omnidirectional from a small, needle-like catheter device can present technical challenges in some instances. The small diameter of the catheter device, necessary for a minimally invasive procedure, can limit the aperture size for any element acoustically radiating axially from the tip. Because of this, the field strength can fall off due to spherical divergence. Even the acoustic wave emitted radially from a sufficiently long transducer falls off cylindrically.

Because of the acoustic intensity falling off due to divergence, the acoustic wave near the catheter device may need to be relatively high to have acoustic intensities sufficient for activating a sonosensitizer several centimeters away from the catheter device. These higher intensities near the catheter device may even be enough to cause indiscriminant cell death close to the catheter device, creating a necrotic region around the catheter device. If this "necrotic" region of the catheter device were unavoidable, it can limit the locations of the body where the catheter device can be placed and limit the number of patients eligible for treatment.

High intensity focused ultrasound (HIFU) provides a non-invasive treatment of lesions using intensities of 500 $W/cm^2$ to 20000 $W/cm^2$ precisely pinpointed over just a few cubic millimeters to cause thermal ablation of the tissue. HIFU techniques can ablate tissue non-invasively by heating the tissue to temperatures above 42° C. causing necrotic cell death. The levels of ultrasound used in this procedure are by design lethal to all cells within the ultrasound focus, therefore with this approach it is not possible to provide broad coverage that discriminates between healthy tissue and diseased tissue.

Additional challenges of non-invasive techniques employing sonodynamic therapy can be the strong attenuation and reflection of acoustic pressure from the patient's body, in particular the skull when treating soft tissue and bone. The impedance mismatch between water/skin and bone is significant resulting in strong reflection at the skin-bone and the bone-brain interfaces. The attenuation coefficient of the skull can also be quite high resulting in losses due to absorption and scattering within the skull.

The following disclosure describes various sonodynamic therapy apparatuses, systems, and methods for a completely non-invasive treatment that can penetrate deep into the body.

SUMMARY

An illustrative non-invasive approach to sonodynamic therapy includes locating several ultrasound transducers or a single transducer with multiple elements outside of the body part used to transmit acoustic waves through the skin and into the body part. The size of the transducers can allow incident acoustic waves to be roughly planar and not suffer from as much divergent loss as cylindrical or spherical divergence. In one aspect, the acoustic waves generated by several ultrasound transducers or several elements of a single transducer converge to allow the wavefronts to constructively interfere. Additionally, the total surface area of acoustic elements can allow the energy transmission to split up amongst many elements instead of requiring all the energy to come from a single element.

Clinically speaking, such a system can improve the experience of patients. It is non-invasive, so the cost and risk of surgery, infection, and hemorrhage is eliminated as well as the cost and complexity of health care is greatly reduced. Preparing a patient for treatment can take significantly less time. The therapy may last 30 minutes to an hour in a non-surgical clinic setting, such as an oncology clinic. A single practitioner can monitor several patients at the same time. Because the risk of the device is lower, this may open the door to more frequent treatment, early treatment within a disease progression, and treatment of less lethal disease.

The illustrative non-invasive apparatuses, systems, and methods described in the following disclosure can use relatively low acoustic intensity over a broader treatment area versus conventional methods. The illustrative non-invasive techniques discussed hereinbelow produce non-thermally ablative temporal average acoustic intensities in the ranges of about 0.1 to about 50 W/cm$^2$, or about 0.2 to about 20 W/cm$^2$, or about 0.5 W/cm$^2$ to about 8.0 W/cm$^2$ over most or all of the body part being treated for lesions such as a region in an organ or tissue which has suffered damage through injury or disease, such as a wound, ulcer, abscess, or tumor. Unless otherwise specifically stated, the terms "about" and "generally," with respect to values, means within 10% of the least significant unit. For example, "about 0.1" means between 0.09 and 0.11.

BRIEF DESCRIPTION OF THE DRAWINGS

The following drawings are illustrative of particular aspects of the present disclosure and therefore do not limit the scope of the appended claims. The drawings are intended for use in conjunction with the explanations in the following description. The disclosed aspects will hereinafter be described in conjunction with the appended drawings, wherein like numerals denote like elements.

DETAILED DESCRIPTION

The following detailed description is exemplary in nature and provides some practical illustrations and examples. Those skilled in the art will recognize that many of the noted examples have a variety of suitable alternatives. A number of various exemplary transcranial sonodynamic therapy devices are disclosed herein using the description provided as follows in addition to the accompanying drawings. Each of the aspects disclosed herein can be employed independently or in combination with one or more (e.g., all) of the other aspects disclosed herein.

Prior to launching into a description of the figures, the present disclosure first turns to a general description of various aspects of non-invasive sonodynamic therapy systems. In one aspect, the present disclosure is directed to a system for sonodynamic therapy. The system comprises a transducer, a patient interface to acoustically couple the transducer to a patient, and a controller coupled to the transducer. The controller is configured to generate an electrical drive signal from a set of modulated acoustic wave parameters, modulate the drive signal, and drive the transducer with the modulated drive signal at a frequency to produce a modulated acoustic wave to produce an acoustic intensity sufficient to activate a sonosensitizer in a treatment region.

In another aspect, the present disclosure is directed to another system for sonodynamic therapy. The system comprises a first transducer, a second transducer, and a controller coupled to the first and second transducers. The controller is configured to generate a first electrical drive signal from a set of modulated acoustic wave parameters, generate a second electrical drive signal from the set of modulated acoustic wave parameters, drive the first transducer at the first electrical drive signal to produce a first acoustic wave, and drive the second transducer at the second electrical drive signal to produce a second acoustic wave. The first and second acoustic waves are combinable to produce an acoustic intensity sufficient to activate a sonosensitizer in a treatment region.

In yet another aspect, the present disclosure is directed to yet another system for sonodynamic therapy. The system comprises a plurality of transducers and a controller coupled to the plurality of transducers. The controller is configured to generate a plurality of electrical drive signals from a set of modulated acoustic wave parameters and drive the plurality of transducers at the plurality of electrical drive signals to produce a plurality of modulated acoustic waves. The plurality of modulated acoustic waves are combinable to produce an acoustic intensity sufficient to activate a sonosensitizer in a treatment region.

Figure 1:
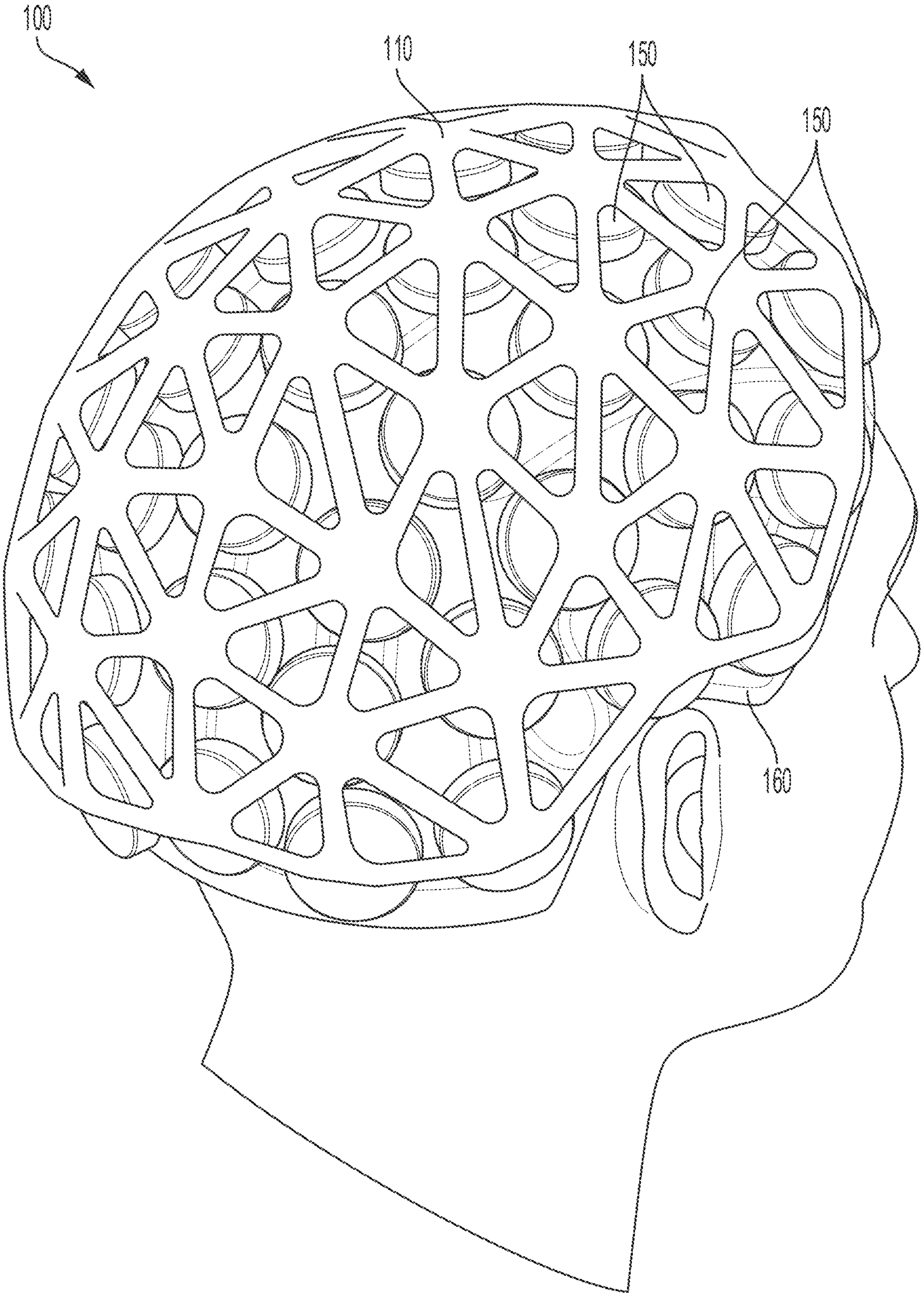
FIG. 1 is a perspective view of a transcranial sonodynamic therapy device with a shell having multiple transducers and a cooling system placed over the head of a patient, according to at least one aspect of the present disclosure.

The following description provides illustrative examples of applications of non-invasive sonodynamic therapy techniques to treat tumors within the brain. It will be appreciated, however, that such techniques can be applied to treat tumors within other body parts. Turning now to FIG. 1, human skulls can vary by gender and anatomical location. One aspect of the present disclosure provides a non-invasive sonodynamic therapy device 100 as shown in FIG. 1. The non-invasive sonodynamic therapy device 100 may comprise a shell 110 with transducers 150 that can provide predictable and consistent insonication despite these variations. The shell 110 may comprise a rigid material. Known relative positions of the transducers 150 can allow for imaging of the head, even in low resolution with large transducers 150. The illustrated aspect may require a mobile stand to hold in position on the patient while he/she waits in a seated or supine position. The rigid shell 110 may be a lightweight helmet that can be worn by the patient during treatment, allowing for predictable placement of the transducers 150 with little infrastructure requirements.

The non-invasive sonodynamic therapy device 100 may comprise a flexible shell 110 (e.g., a helmet) with transducers 150 placed over a liquid-cooled skull cap 160 as described further elsewhere herein, requiring little infrastructure to support the array of transducers 150. It may be possible for the patient to don the skull cap 160 and shell 110 in any chair while he/she waits for treatment to complete. The lightweight design may minimize neck pain from the patient holding up his/her head for extended periods with the weight of the transducers 150 and cooling cap. The flexible shell 110 can conform to the shape of each skull. Such a device may account for subtle variations between treatments depending on the shape of each patient's head curving some transducers 150 more inward or outward.

The non-invasive sonodynamic therapy device 100 may comprise rigid or flexible patches with several transducers 150 that can be removably applied to the head. Such an aspect may require clinicians to apply each patch individually. Having separate patches can allow for some treatment flexibility without requiring each transducer 150 to be planned and placed individually. An illustrative non-invasive sonodynamic therapy device 100 may minimize sores caused by adhering patches to the head repeatedly, which may be a particular concern for older and sicker patients.

The non-invasive sonodynamic therapy device 100 may comprise patches with single transducers 150 that can be removable applied to the head. Individual transducers 150 can provide the most treatment flexibility. Such a device may require a detailed process for planning to apply and applying the transducers 150. Given the additional flexibility, the illustrative non-invasive sonodynamic therapy device 100 may accommodate for greater usability risk.

Figure 2:
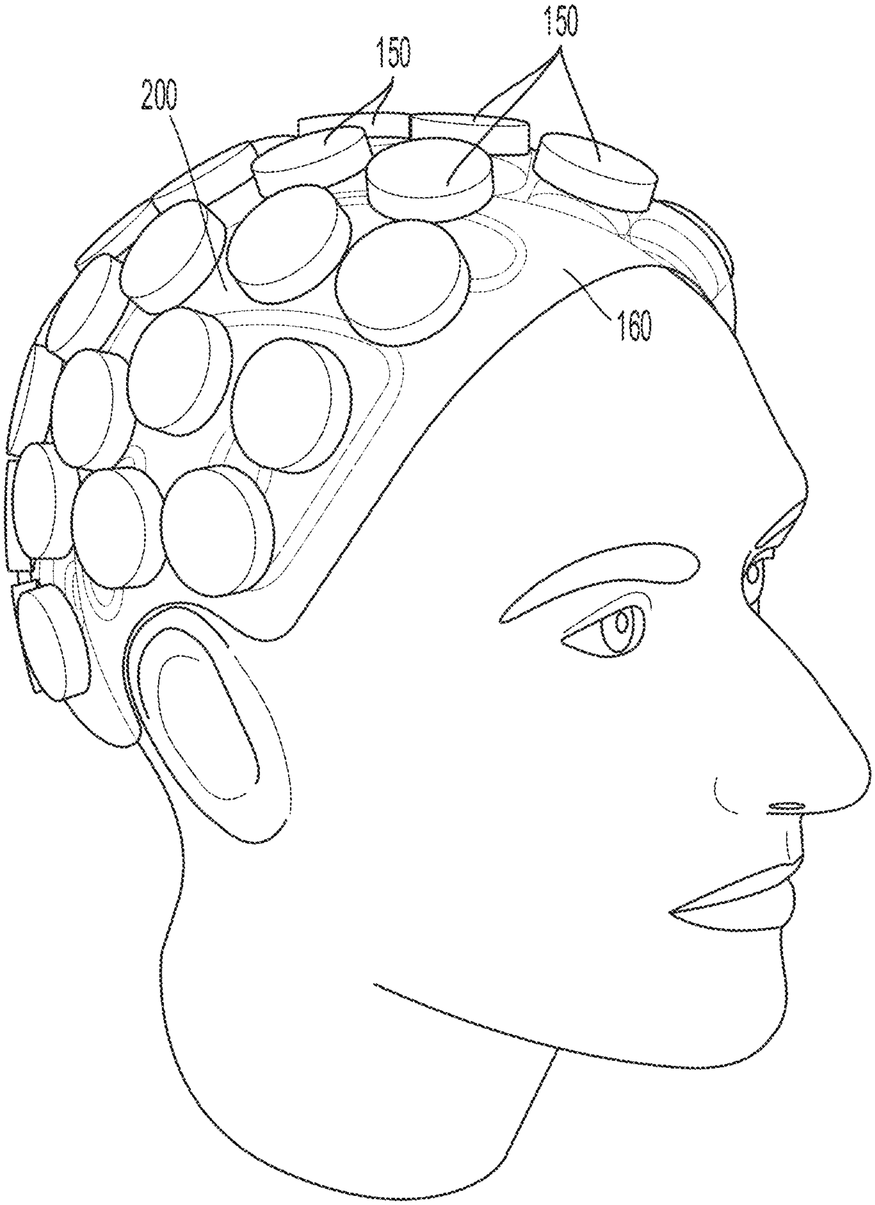
FIG. 2 is a perspective view of a transcranial sonodynamic therapy device with multiple transducers and a cooling system placed over the head of a patient, according to at least one aspect of the present disclosure.

The size and shape of the transducers 150, as can be seen in FIG. 2, may vary across various disclosed aspects. For a cost-effective and simple system, larger transducers 150, which produce directional acoustic waves, may be used. Large transducers 150 can be made less directional by applying to each transducer 150 an acoustic lens that bends the acoustic waves as described further elsewhere herein. For a system that can conform to the head, smaller transducers 150, which can radiate more broadly than larger transducers 150, can be used. Such small transducers 150 can have a greater ability to image or beam steer as an array.

Figure 3:
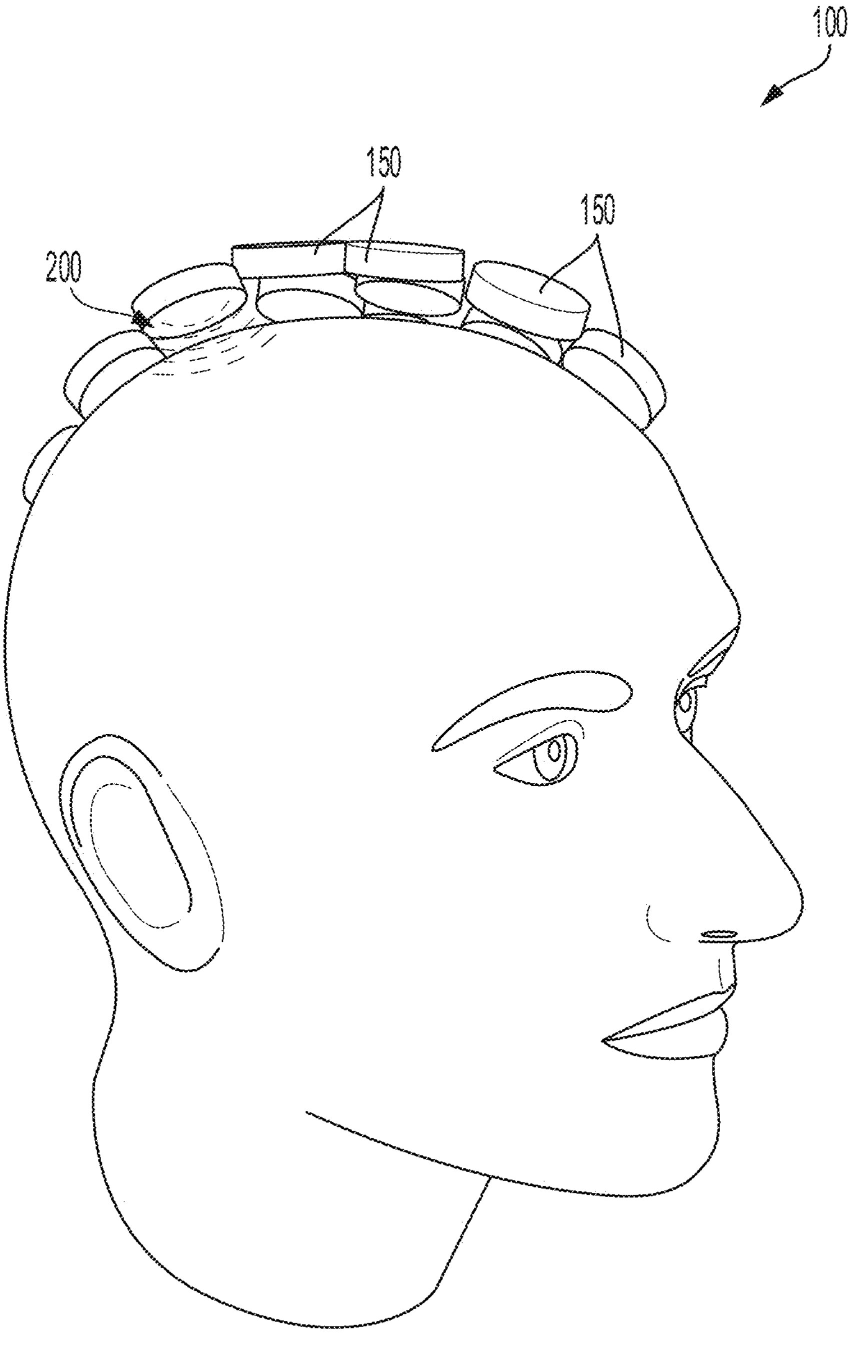
FIG. 3 is a partial cutaway view of a transcranial sonodynamic therapy device placed over the head of a patient showing a partial view of the multiple transducers, according to at least one aspect of the present disclosure.

FIG. 3 is a partial cutaway view of a transcranial sonodynamic therapy device 100 placed over the head of a patient showing a partial view of the multiple transducers 150, according to at least one aspect of the present disclosure. Instead of focusing an acoustic wave 200 to a small point, the acoustic wave 200 can be defocused to minimize the spatial variation of the acoustic wave intensity in the brain.

The size and shape of the transducers 150 may defocus or focus each transducer 150. As used herein, the term focused refers to an acoustic wavefront that is more convergent than a wavefront produced by a transducer 150 with a planar emitting surface and the term defocused refers to an acoustic wavefront that is more divergent than a wavefront produced by a transducer 150 with a planar emitting surface. Whether a lens needs to be concave or convex to make a wave more divergent depends on whether the acoustic wave is transitioning from a region of low acoustic impedance to a region of high acoustic impedance or the acoustic wave is transitioning from a region of high acoustic impedance to a region of low acoustic impedance. In this regard, if a lens is made of a material with higher acoustic impedance than the target medium (water/tissue), the acoustic wave originates in the high-impedance material and transitions to the low-acoustic impedance target medium. If the lens is concave, the lens will "focus" the acoustic wave to make it more convergent. If the lens is convex, the lens will "defocus" the acoustic wave to make it more divergent.

Figure 4:
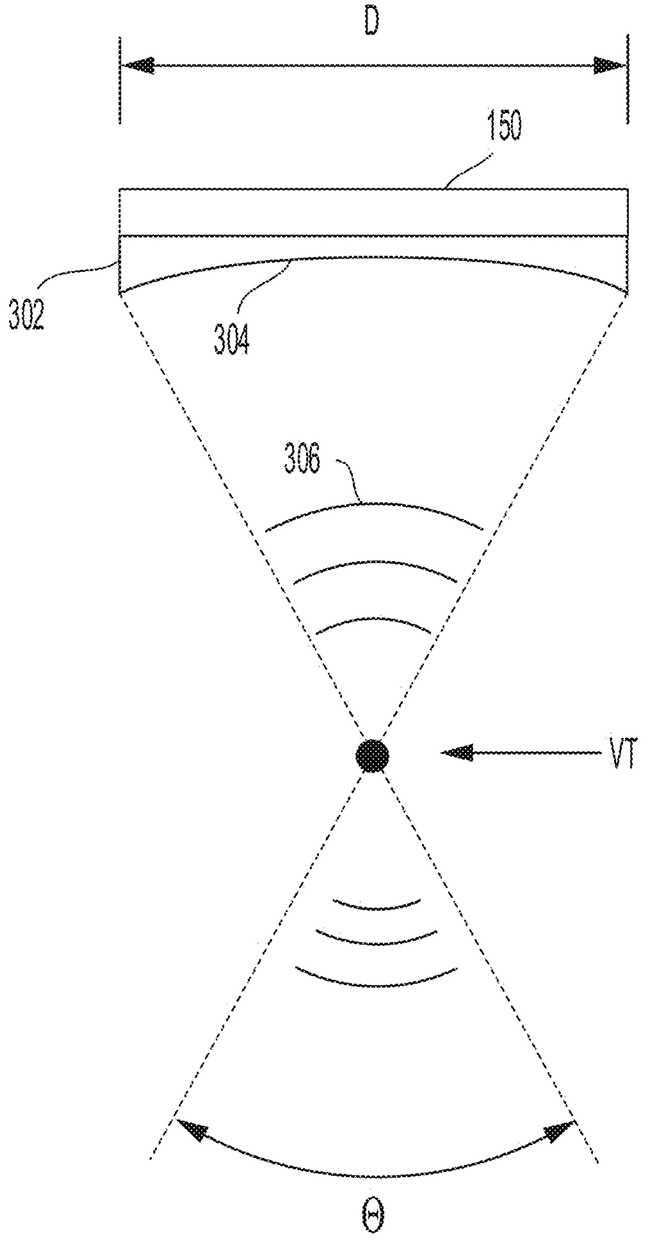
FIG. 4 is a schematic view of a transducer with a lens defining a concave surface, according to at least one aspect of the present disclosure.

FIG. 4 is a schematic view of a transducer 150 with a lens 302 defining a concave surface 304, according to at least one aspect of the present disclosure. The lens 302 may be acoustically coupled to the transducer 150 or may be formed integrally therewith. In the illustrated example, the lens 302 is made of a material with higher acoustic impedance than the target medium (water/tissue) such that the acoustic wave 306 originates in the high-impedance material and transitions to the low-acoustic impedance target medium causing the acoustic wave 306 "focus" or converge to the target tissue.

Figure 5:
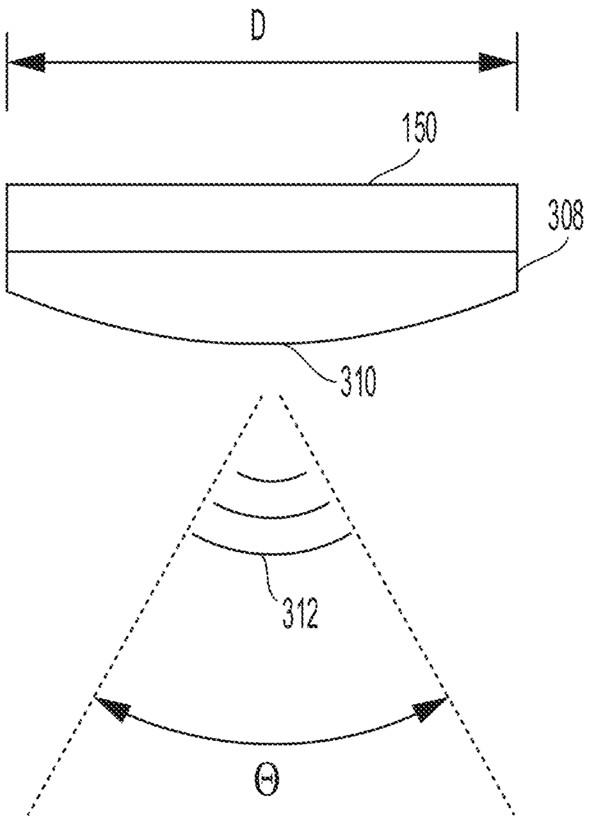
FIG. 5 is a schematic view of a transducer with a lens defining a convex surface, according to at least one aspect of the present disclosure.

FIG. 5 is a schematic view of a transducer 150 with a lens 308 defining a convex surface 310, according to at least one aspect of the present disclosure. The lens 308 may be acoustically coupled to the transducer 150 or may be formed integrally therewith. In the illustrated example, the lens 308 is made of a material with higher acoustic impedance than the target medium (water/tissue). Accordingly, an acoustic wave 312 originates in the high-impedance material and transitions to the low-acoustic impedance target medium causing the acoustic wave 312 to "defocus" or diverge to the target tissue.

The focus of the transducers 150 also depends on the material and shape of the lens (not shown). Using a lens 302, 308 allows the transducers 150 to be flat, which may minimize manufacturing costs. Both the lens 302 with the concave surface 304 and the lens 310 with the convex surface 310 may be configured to produce a fixed focus.

It may be possible to produce a lens that can adjust its shape to create different focuses. It may be possible to create an elastic, fluid-filled pocket that functions as a lens. The fluid can be pumped in or out of the lens to adjust shape of the pocket and thus the focus of the transducers.

Figure 6:
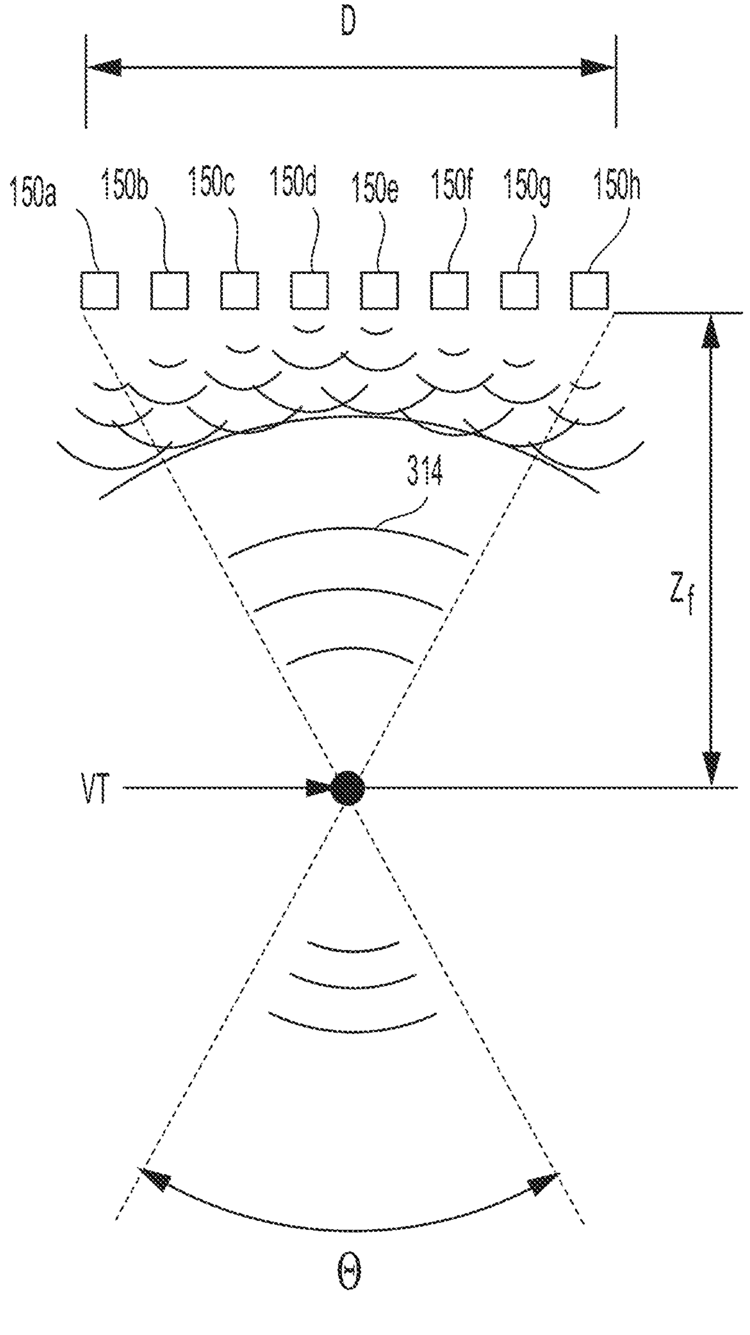
FIG. 6 is a schematic view of a transducer with multiple elements that can be individually energized to produce a variety of acoustic waves, according to at least one aspect of the present disclosure.

FIG. 6 is a schematic view of a transducer 150 with multiple elements 150*a*-150*h* that can be individually energized to produce a variety of acoustic waves, according to at least one aspect of the present disclosure. As shown in FIG. 6, multiple transducer elements 150*a*-150*h* can be arranged in an array to produce converging, diverging, or planar, acoustic waves. For examples, the transducer elements 150*a*-150*h* can be activated in a predetermined sequence to selectively generate convergent/divergent/planar acoustic waves, such as, for example, the convergent acoustic wave 314, shown in FIG. 4, or a divergent acoustic wave 312 shown in FIG. 5. To generate a converging acoustic wave 314, for example, the outer transducer elements 150*a*, 150*h* are initially energized and after a time delay the adjacent inner transducer elements 150*b*, 150*g* are energized. The next adjacent inner transducer elements 150*c*, 150*f* are energized after a second time delay. Finally, the inner transducer elements 150*d*, 150*e* are energized after a third time delay. This pattern can be repeated to generate the converging acoustic wave 314. The first, second, and third time delays may be equal or may vary in order to generate more complex acoustic waves. Alternatively, the transducer elements 150*a*-150*h* may be energized in reverse order to produce a diverging acoustic wave using equal or different time delays. The transducer elements 150*a*-150*h* can be interchangeably configured to transmit or receive acoustic waves.

Figure 7:
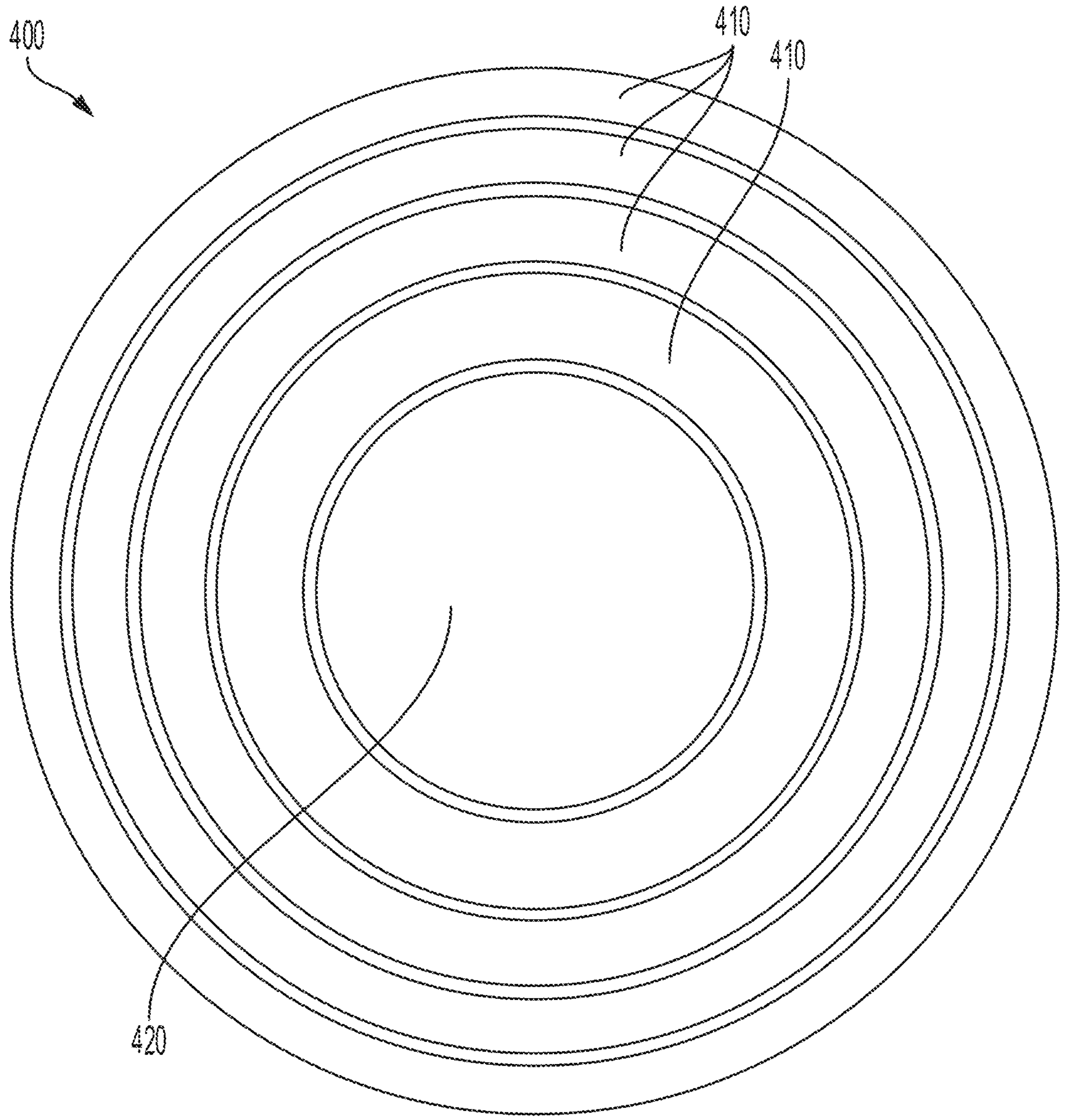
FIG. 7 is a bottom view of a transducer having an internal element surrounded by concentric rings, according to at least one aspect of the present disclosure.

FIG. 7 is a bottom view of a transducer 400 having an internal element 420 surrounded by concentric rings 410, according to at least one aspect of the present disclosure. Each transducer 150 can be adapted and configured to produce an acoustic wave with variable focus. One way to accomplish this can be with each transducer 400 having concentric rings 410 (e.g., an annular array) as shown in FIG. 7. Each concentric ring 410 can be driven with a different signal. To focus the acoustic wave, the signal going to the inner element 420 may be progressively more delayed than the outer of the concentric ring 410. The acoustic waves from each concentric ring 410 may converge at a point. To defocus the acoustic wave coming from an annular array, the acoustic wave at the outer of the concentric rings 410 may be progressively more delayed relative to the inner element 420. One way to make an annular array can be with concentric rings 410 of equal area. In another aspect, the annular array may comprise concentric rings 410 of unequal area.

Figure 8:
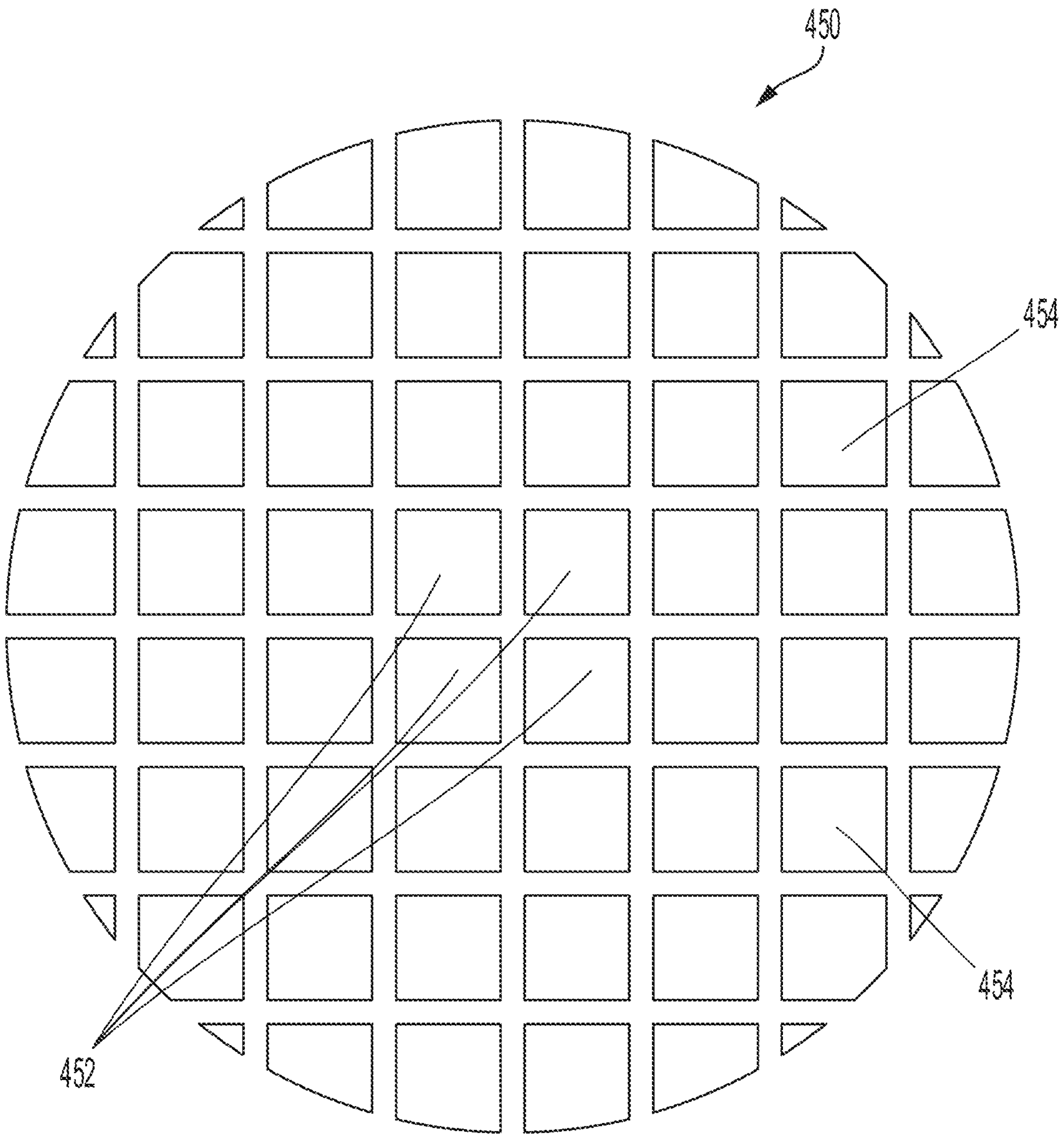
FIG. 8 is a bottom view of a transducer having internal elements arranged in 2-dimensional (2D) grid array, according to at least one aspect of the present disclosure.

FIG. 8 is a bottom view of a transducer comprising internal elements 452 arranged in 2-dimensional (2D) grid array 450, according to at least one aspect of the present disclosure. Each internal element 452 of the 2D grid transducer array 450 can be driven with a different signal. To produce a converging acoustic wave (e.g., "focus"), the signal applied to the inner element 454 may be progressively more delayed than the signal applied to the outer elements of the 2D grid transducer array 450. To produce a diverging acoustic wave (e.g., "defocus"), the acoustic wave produced by the outer elements 452 may be progressively more delayed relative to the inner element 454. In one aspect, each of the internal elements 452 of the 2D grid transducer array 450 may define an equal area. In another aspect, each of the internal elements 452 of the 2D grid transducer 450 array may define an unequal area.

In one aspect, the transducer 150, 400, 450 may be implemented as a single transducer comprising multiple piezoelectric elements with acoustically/electrically-independent sections arranged in an array. In other aspects, the transducer 150, 400, 450 may be implemented as different transducers working in a coordinated manner. There is little or no distinction from a physics perspective between a single transducer with multiple elements and different transducers working in coordination. The elements of an array can be sized on the order of a wavelength. In one aspect, the transducer 150, 400, 450 may be implemented as a single transducer comprising a plurality of elements implemented as an annular array as shown in FIG. 7 or as a grid array as shown in FIG. 8. In another aspect, the transducer 150, 400, 450 may be implemented as a plurality of individual transducers.

In one aspect, each of the transducers 150, 400, 450 shown in FIGS. 4-8, or elements thereof, are non-invasive and may be implemented in a suitable size and shape to fit on the body part of the patient. Also, the individual number and arrangement of transducer elements may be selected to fit on the body part of the patient. In one aspect, the transducer 150, 400, 450, or elements thereof, may be made of piezoelectric or single crystal material which converts electrical energy to ultrasonic energy. The transducer 150, 400, 450 also can receive back ultrasonic energy and converts it to electrical energy. Each of the transducers 150, 400, 450, or elements thereof, may be adaptively focused to produce acoustic waves by collaborative transducer performance. For example, each of the transducers 150, 400, 450, or elements thereof, may be selectively controlled to operate either as a transmitter or as a receiver by a controller as described hereinbelow. Further, each of the transducers 150 400, 450, or elements thereof, may be selectively energized and actuated to produce convergent, divergent, or planar acoustic waves as discussed in more detail in the following description.

With reference now to FIGS. 4-8, in one aspect, the acoustic wave produced by the transducer 150, 400, 450 may be defined by vergence—a measure of the curvature of the acoustic wavefront. A negative vergence is when the acoustic wavefront propagates away from a point (i.e., divergence). A positive vergence is when the acoustic wavefront propagates towards a point (i.e., convergence). A zero vergence is a planar acoustic wavefront that does not converge or diverge. Vergence is a property of a single acoustic wavefront. A single converging/diverging acoustic wavefront may be produced by multiple elements of a transducer 150, 400, 450 (e.g., a transducer comprising an annular array 400 or a grid array 450).

In one aspect, the acoustic wave produced by the transducer 150, 400, 450 may be characterized by phase and/or delay. The phase and/or delay may be employed to measure a relative shift in time between two acoustic waves. The phase is the amount of time shifted between two acoustic waves relative to the period of the two acoustic waves (e.g., measured in degrees or radians). The delay is a measure of the amount of time shifted between two acoustic waves (e.g., measured in milliseconds). Delay and phase are often used interchangeably. For example, although "delay" may be described in units of degrees or radians, it is well understood that "delay" is an abbreviation for "phase delay." For a single acoustic wave pulse, it is clearer to discuss delay between the peaks of two acoustic wave pulses in terms of time because a phase shift requires a periodic signal. For repeating acoustic waves, the relative delay is often measured terms of phase. For continuous, periodic acoustic waves, delaying an integer number of periods should have no effect because, by definition, a periodic signal exhibits symmetry over full period shifts. For pulses of a repeating acoustic wave (e.g., 1000 cycles of a sine wave), the acoustic wave can be delayed by an integer number of cycles. The beginning and end of the wave packet will have some edge effect when one signal begins/ends before the other. In the middle of the two wave packets, there will be no effect (provided the signals still overlap).

In one aspect, the transducers 150, 400, 450 may be adapted and configured to produce a "focused" acoustic wave by producing a convergent acoustic wave that converges to a point. In another aspect, the transducers 150, 400, 450 may be adapted and configured to produce a "defocused" acoustic wave, e.g., a divergent acoustic wave. In other aspects, the transducers 150, 400, 450 may be adapted and configured to produce a planar acoustic wave (e.g., zero vergence) where the acoustic wave is neither "defocused" nor "defocused."

In various aspects, the transducers 150, 400, 450 may be driven at ultrasonic frequencies in a range of about 20.00 kHz to about 12.00 MHz. More particularly, the transducers 150, 400, 450 may be driven at ultrasonic frequencies in a range of about 650.00 kHz to about 2.00 MHz. In a preferred range, the transducers 150, 400, 450 may be driven at ultrasonic frequencies in a range of about 900.00 kHz to about 1.20 MHz and more preferably at about 1.06 MHz.

Figure 9:
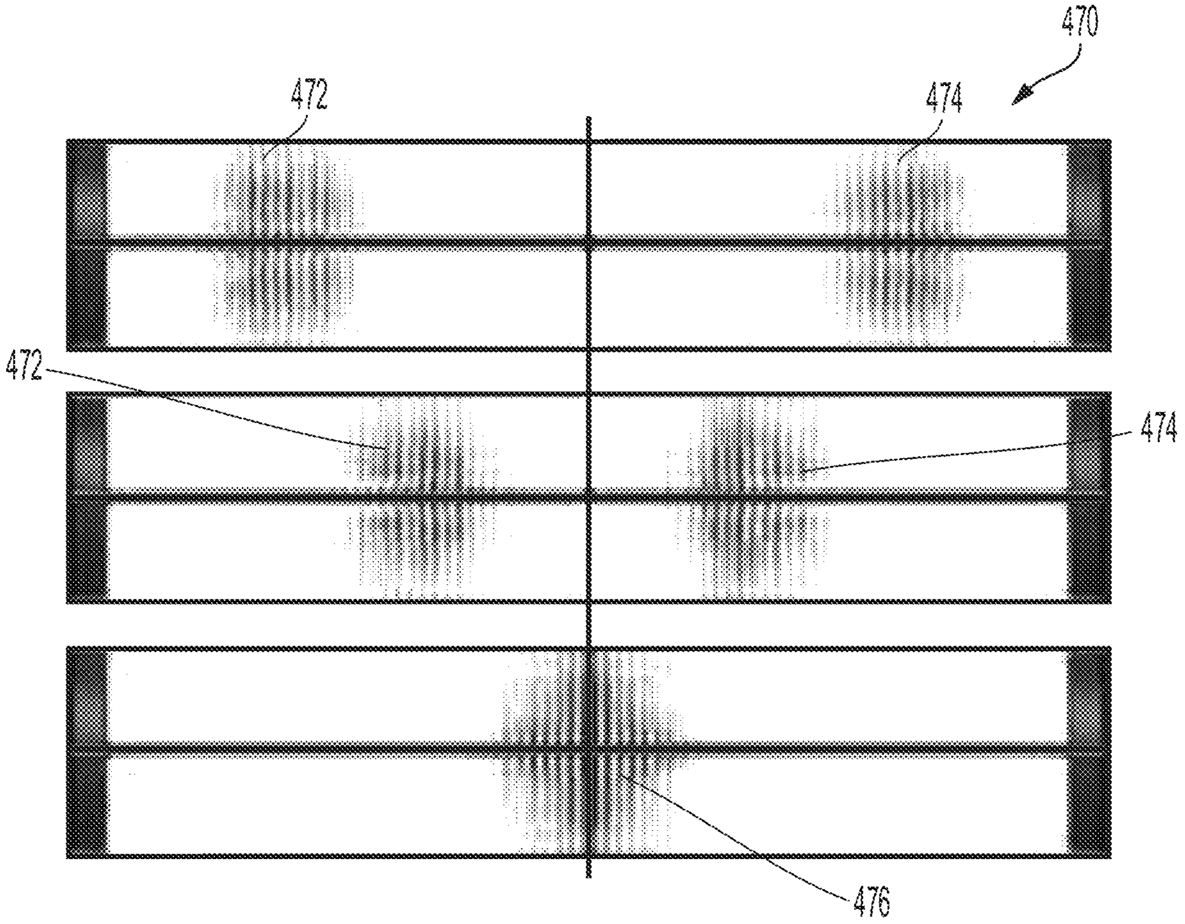
FIG. 9 is a diagram of two acoustic ultrasonic pulses without delay that constructively interfere, according to at least one aspect of the present disclosure.

FIG. 9 is a diagram 470 of two acoustic ultrasonic pulses 472, 474 without delay that constructively interfere, according to at least one aspect of the present disclosure. As previously described, the transducers 150, 400, 450 may be adapted and configured to produce a "focused" acoustic wave by coordinating time between multiple acoustic wavefronts and producing wavefronts that constructively interfere. The coordination of acoustic wavefronts is independent of the vergence of the acoustic wavefronts. The point at which the wavefronts focus can be adjusted by delaying one signal relative to another. The diagram 470 shown in FIG. 9 shows two pulses 472, 474 produced without any relative delay. The two pulses 472, 474 constructively interfere when they reach the center and may be said to be focused in the center to produce a combined pulse 474. If the acoustic pulse 472 on the left is delayed relative to the acoustic pulse 474 on the right, the two pulses 472, 474 would meet at a point left of center, thus shifting the point of constructive interference to the left of center. Likewise, if the acoustic pulse 474 on the right is delayed relative to the acoustic pulse 474 on the right, the two pulses 472, 474 would meet at a point to the right of center, thus shifting the point of constructive interference to the right of center.

In another aspect, a mixture of convergent/divergent/planar acoustic waves may be timed to meet and constructively interfere at one location. A divergent acoustic wave may be timed to meet and destructively interfere at one location.

Control of the converging and diverging wavefronts produced by the transducers 150, 400, 450 can be taken into account as part of pretreatment planning. Based on inputs from the pretreatment planning processes the controller can adaptively modulate the transducers 150, 400, 450 such that the acoustic wavefronts coordinate to preferentially target a desired treatment region. In one aspect a digital imaging and communications (DICOM) image from a computerized tomography (CT) or other imaging source could be an input to the device controller to generate customized modulation pattern that optimizes the treatment region for a particular patient. In another aspect the pretreatment planning could include selection of a preferred transducer type or arrangement of transducer types that will produce an optimized treatment region for a particular disease state. In another aspect, the patient interface may come in various arrangements that can be selected during pretreatment planning to coordinate the transducer(s) in preferred arrangement for treatment.

"Defocused" acoustic waves may be measured based on the volume of tissue treated according to the number of nodes and antinodes. A histogram of intensities or pressures over some volume may be employed to measure "defocused" acoustic waves. In one aspect, a dose-volume histogram may be employed in planning sonodynamic therapy. Alternatively, a cumulative histogram may be employed.

Figure 10:
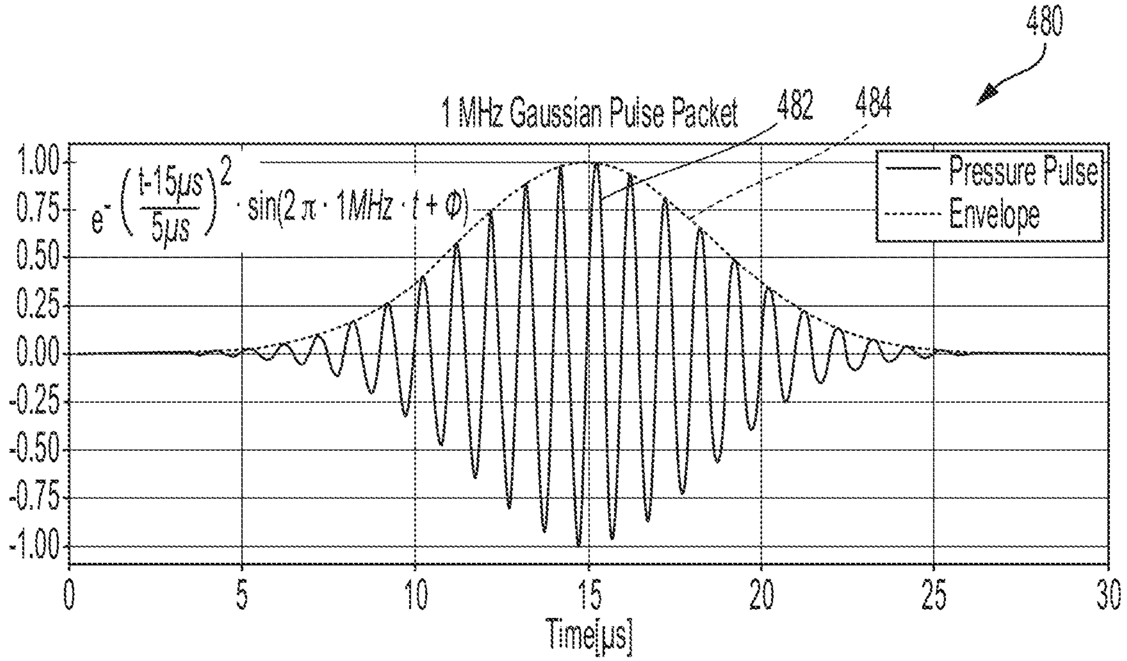
FIG. 10 is a diagram of a pulse packet made of a sine wave signal modulated by a Gaussian pulse signal, according to at least one aspect of the present disclosure.

FIG. 10 is a diagram of an acoustic pulse packet 480 made of a repeating signal modulated by a Gaussian pulse signal, according to at least one aspect of the present disclosure. In one aspect, the acoustic wave generated by the transducer 150, 400, 450 may be amplitude modulated. The acoustic pulse packet 480 may be produced by modulating a repeating signal, such as a sine wave, with a Gaussian pulse where the repeating signal is independent from the Gaussian pulse. When the transducer 150, 400, 450 is driven by the modulated signal, it produces an acoustic pressure pulse 482 where the amplitude varies according to the envelope 484, which is in the form of the Gaussian pulse. Although, in the illustrated example, the repeating signal is a sine wave, the repeating signal may take many forms. The repeating signal may be modulated by rectangular pulses, triangular pulses, or pulses of a predefined mathematical shape. In addition to amplitude modulation, a repeating signal may be pulse-width modulated, duty-cycle modulated, phase modulated, frequency modulated, randomized phase modulated, or may be modulated using any suitable modulation technique to produce a desired acoustic pulse packet. The repeating signal may include inter or intra pulse variations.

Figure 11:
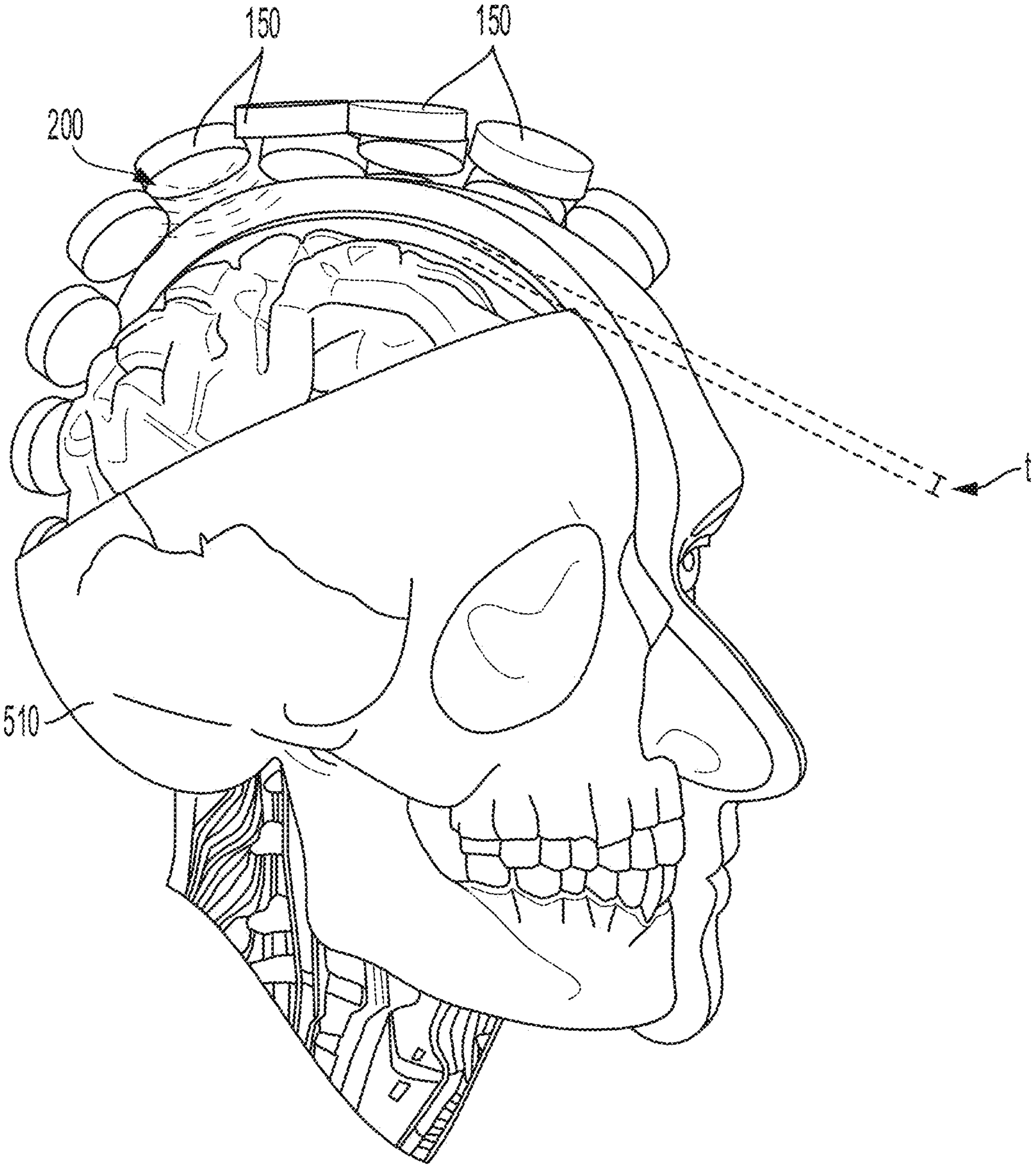
FIG. 11 is a partial cutaway view of a transcranial sonodynamic therapy device placed over the head of a patient showing a partial view of the skull and brain of the patient and multiple transducers with one transducer emitting energy into the brain of the patient, according to at least one aspect of the present disclosure.

FIG. 11 is a partial cutaway view of a transcranial sonodynamic therapy device placed over the head of a patient showing a partial view of the skull 510 and brain of the patient and multiple transducers 150 with one transducer emitting energy 200 into the brain of the patient, according to at least one aspect of the present disclosure. It can be possible to take measurements or get a rough image of the skull 510 as shown in FIG. 11. This can be facilitated if the transducers 150 are fixed to a rigid shell and their relative positions and orientations are known. Rough measurements can be used to adjust the treatment algorithm by measured parameters such as skull thickness, "t." Each transducer 150 may send out an acoustic pulse and listen for an echo. The echoes can be used for a quick estimate of the skull thickness, "t," under each transducer 150. For treatment of tumors in other body parts of the patient, the sonodynamic therapy device may be adapted and configured to the couple to the body of the patient.

For designs with transducers 150 that have an adjustable focus, the focus of each transducer 150 can be set beforehand with treatment planning. Alternatively, the transducers 150 can adjust their focus automatically based on temperature readings of the head or based on skull thickness, "t," measurements.

The amplitude of the electrical drive signal driving the transducers 150 can be controlled or modulated. In some cases, it can be beneficial to modulate the electrical drive signal driving the transducers 150 based on the temperature of the head or other body part being treated. For example, if the temperature sensors are detecting a sharp rise in temperature, the amplitude of the transducers 150 can be decreased, shut off for a period, or the duty cycle can be decreased. By modulating the intensity of the acoustic pulses, the temporal average acoustic intensity may be regulated to activate the sensitizer while maintaining the temperature of the tumor cells below a temperature (e.g., below 42° C.) capable of causing thermal damage to the cell and in some circumstances necrotic cell death. In another aspect, sonodynamic therapy can function at a variety of different frequencies. Each frequency can transmit through a skull 510 efficiently with certain thicknesses of skulls. Using a variety of frequencies can allow a non-invasive sonodynamic therapy device 100 to operate on a broad range of skull thicknesses, "t."

In aspects where the transducers 150 can operate at multiple frequencies, the frequency of each transducer 150 can be selected manually or automatically. As stated in the foregoing description, the transducers 150 may be driven at ultrasonic frequencies in a range of about 20.00 kHz to about 12.00 MHz. More particularly, the transducers 150 may be driven at ultrasonic frequencies in a range of about 650.00 kHz to about 2.00 MHz. In a preferred range, the transducers 150 may be driven at ultrasonic frequencies in a range of about 900.00 kHz to about 1.20 MHz and more preferably at about 1.06 MHz. The frequencies can be preselected by a physician. The frequencies can be selected based on a measurement of head anatomy (e.g. skull thickness, "t"). For example, each transducer 150 can send out a sequence of pulses to measure the thickness of the skull 510 closest to it. Based on the result of the skull thickness, "t," measurement, an algorithm can be used to select frequencies from a set of frequencies or from a range of frequencies that may be best suited for the skull thickness, "t," and energize the transducers 150 accordingly.

The size and shape of the transducers 150, as can be seen in FIG. 2, may vary across various disclosed aspects. For a cost-effective and simple system, larger transducers 150, which may have directional acoustic waves, may be used. Large transducers 150 can be made less directional by applying to each transducer 150 an acoustic lens that bends the acoustic waves as described further elsewhere herein. For a system that can conform to the skull, smaller transducers 150, which can radiate more broadly than larger transducers 150, can be used. Such small transducers 150 can have a greater ability to image or beam steer as an array.

Instead of focusing an acoustic wave 200 to a small point, the acoustic wave 200 can be defocused to minimize the spatial variation of the acoustic wave intensity in the brain as shown in FIG. 4. The size and shape of the transducers 150 may defocus or focus each transducer 150. Defocused transducers can be formed using a transducer 150 with a convex emitting surface 310 as seen in FIG. 5. As seen in FIG. 4, design of the transducers can focus the sound from each transducer 150 using a concave emitting surface 304 with a center of curvature where the sound can focus. As shown in FIG. 6, an array of transducers 150*a*-150*h* can be used to generate acoustic waves that are convergent, divergent, or more complex.

Each transducer 150 can cycle through several frequencies so that at least one of the frequencies can transmit nearly optimally for the given skull thickness, "t." Each transducer 150 may also sweep continuously from one frequency to another. A frequency can be pre-selected for each transducer 150 based on the thickness of skull 510 nearest to it (e.g., during treatment planning by the physician). Prior to treatment, each transducer 150 can transmit test signals and monitor the reflected sound to automatically determine which frequency or frequencies can work best for that one of the transducers 150. The test signals can be used to measure the skull thickness, "t," directly by measuring delays in pulse echoes, or they can be used to detect the relative amount of reflected acoustic energy.

Each transducer 150 can be made up of a broad-spectrum ultrasonic transducer or can be made up of several smaller transducers (e.g., piezo-electric elements as shown in FIGS. 6-8) designed to work at particular frequencies. Each transducer 150 can have an element specifically designed to monitor the waves reflected from the head. In the case where the transducers 150 are made of several smaller transducers 150, while one transducer 150 is transmitting sound, the other transducers 150 may be used to monitor the incoming acoustic pulses.

Of all the frequencies that work with sonodynamic therapy, a subset of frequencies can be selected to best cover a range of common skull thicknesses, "t." Frequencies that share many common factors (e.g., harmonics such a 1 MHz and 2 MHz) may not make good choices to cover the most number of skull thicknesses because many of the transmission peaks between the two frequencies can be shared. Frequencies without many or any common factors (e.g., coprime numbers) may make for good choices for frequencies because the transmission peaks can occur at different skull thicknesses.

Figure 12:
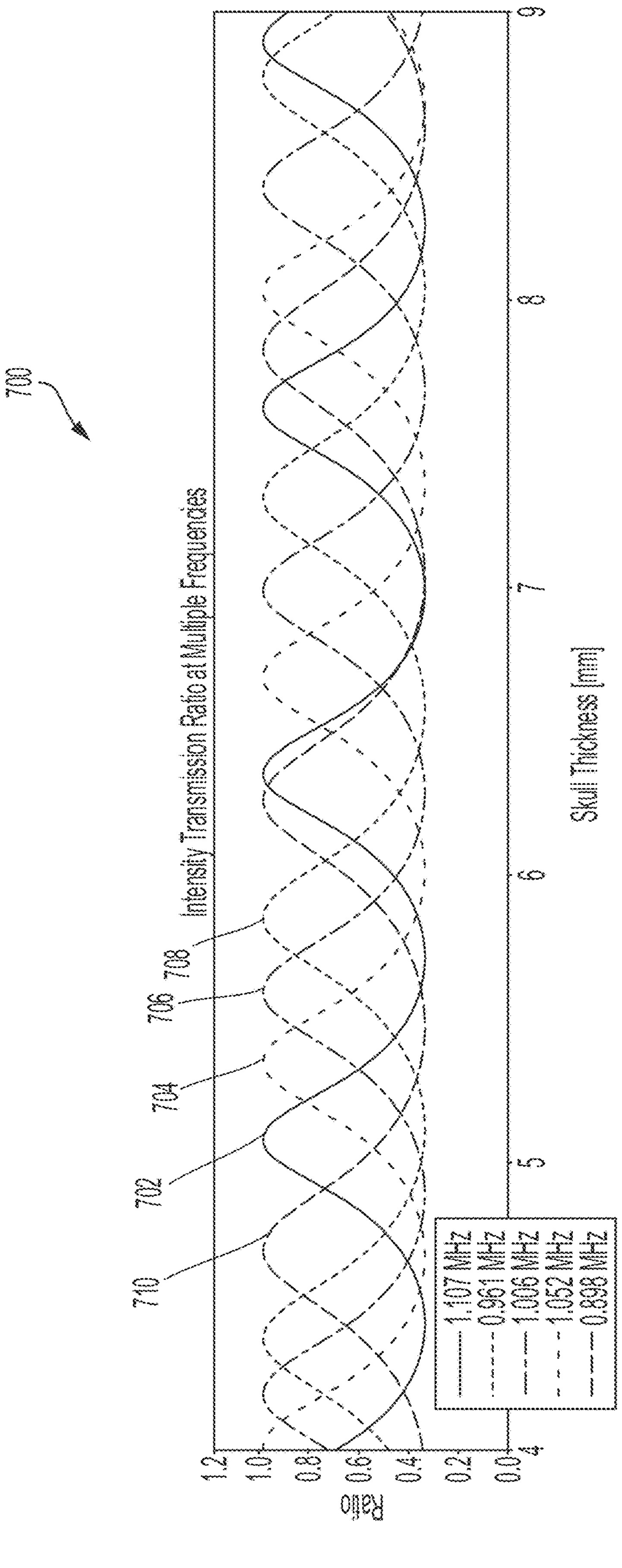
FIG. 12 is a chart showing an intensity transmission ratio across multiple frequencies, according to at least one aspect of the present disclosure.

FIG. 12 is a chart 700 showing an intensity transmission ratio across multiple frequencies, according to at least one aspect of the present disclosure. As shown in FIG. 12, the transmission of 5 different frequencies across different skull thicknesses between 4 mm and 9 mm. A first frequency 702 at 1.107 MHz, a second frequency 704 at 1.052 MHz, a third frequency 706 at 1.000 MHz, a fourth frequency 708 at 0.961 MHz, and a fifth frequency at 0.898 MHz. There can be good coverage of different skull thicknesses. In this example, each skull thickness can have at least one frequency that can transmit 75% or more of its energy. This can be accomplished with frequencies between 898 kHz and 1.107 MHz, a range of only 0.2 MHz.

Transmission of sound through an absorbing layer of tissue may not monotonically decrease as function of thickness. Instead, transmission can be enhanced when the thickness of the skull is a multiple of half the wavelength of the sound in that layer. Similarly, when the thickness of the skull is an odd multiple of quarter wavelengths (halfway between A/2 multiples), the transmission can be reduced.

Figure 13A:
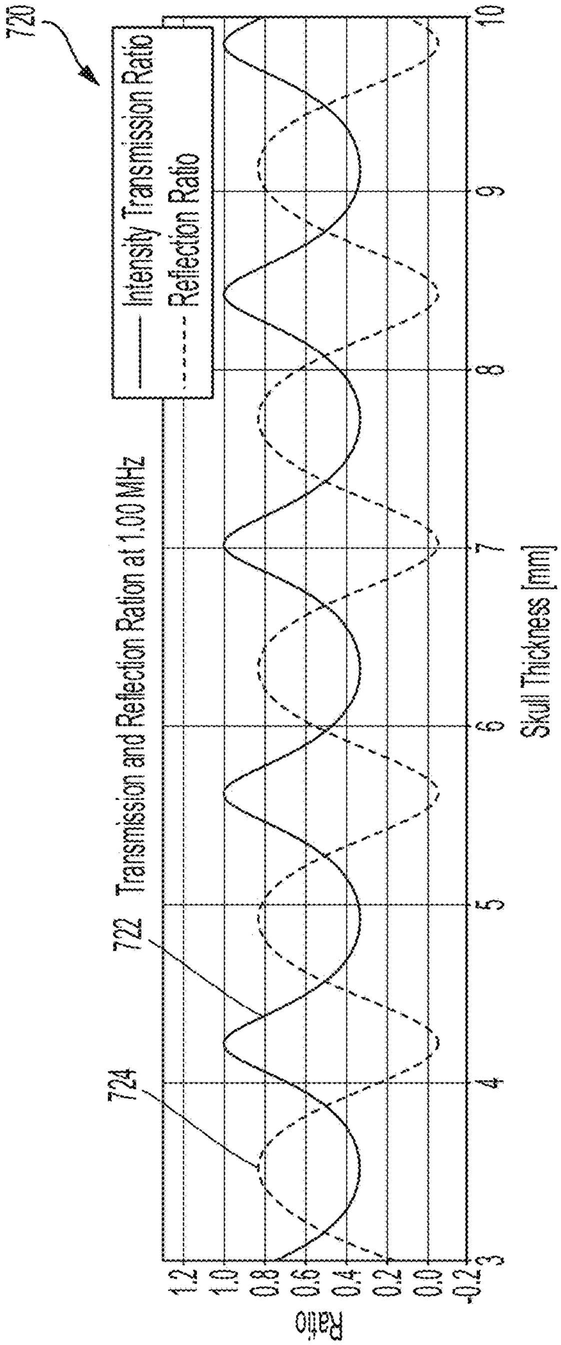
FIG. 13A is a chart showing a transmission and reflection ratio at 1 MHz versus skull thickness in millimeters, according to at least one aspect of the present disclosure.
Figure 13B:
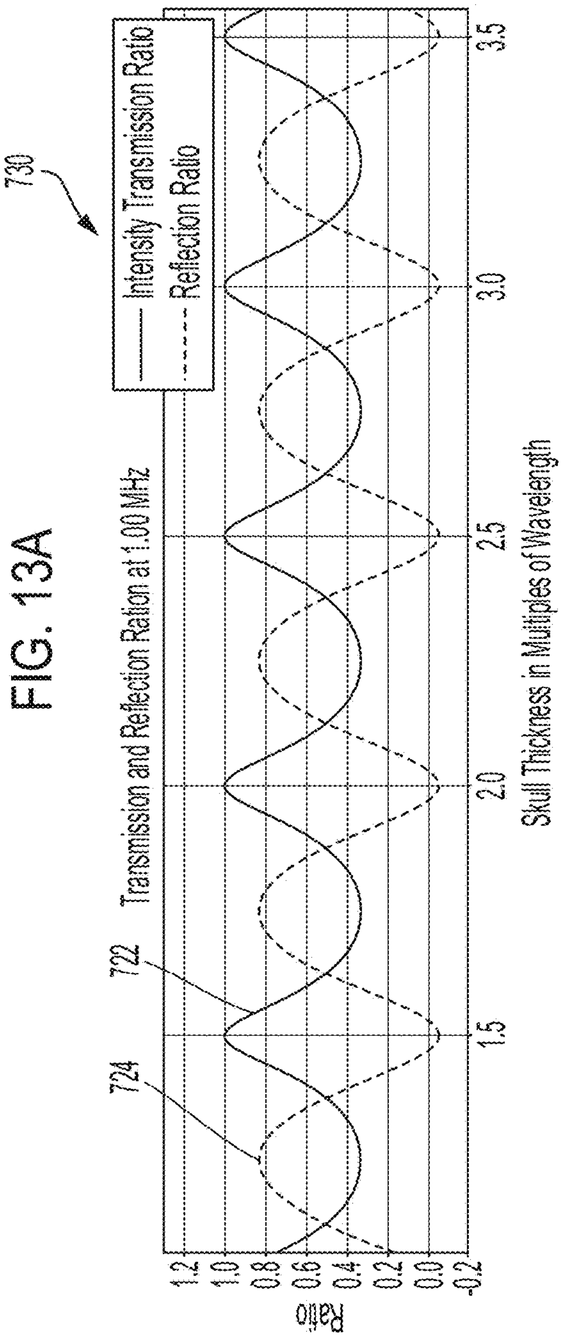
FIG. 13B is a chart showing a transmission and reflection ratio at 1 MHz versus skull thickness in wavelengths, according to at least one aspect of the present disclosure.

FIG. 13A is a chart 720 showing an intensity transmission and pressure reflection ratio at 1 MHz versus skull thickness in millimeters and FIG. 13B is a chart 730 showing a transmission and reflection ratio at 1 MHz versus skull thickness in wavelengths, according to at least one aspect of the present disclosure. As shown in FIGS. 13A and 13B, the transmission of a 1 MHz soundwave through various skull thicknesses. FIG. 7A shows the skull thickness in millimeters and FIG. 13B shows the skull thickness in multiples of wavelength of the intensity transmission ratio 722 and the reflection ratio 724. The intensity transmission ratio 722 can reach a peak whenever the skull is a multiple of a half wavelength. Likewise, the ratio of sound reflected shown as the reflection ration 724 can be at a minimum whenever the skull is a multiple of a half wavelength.

Figure 14B:
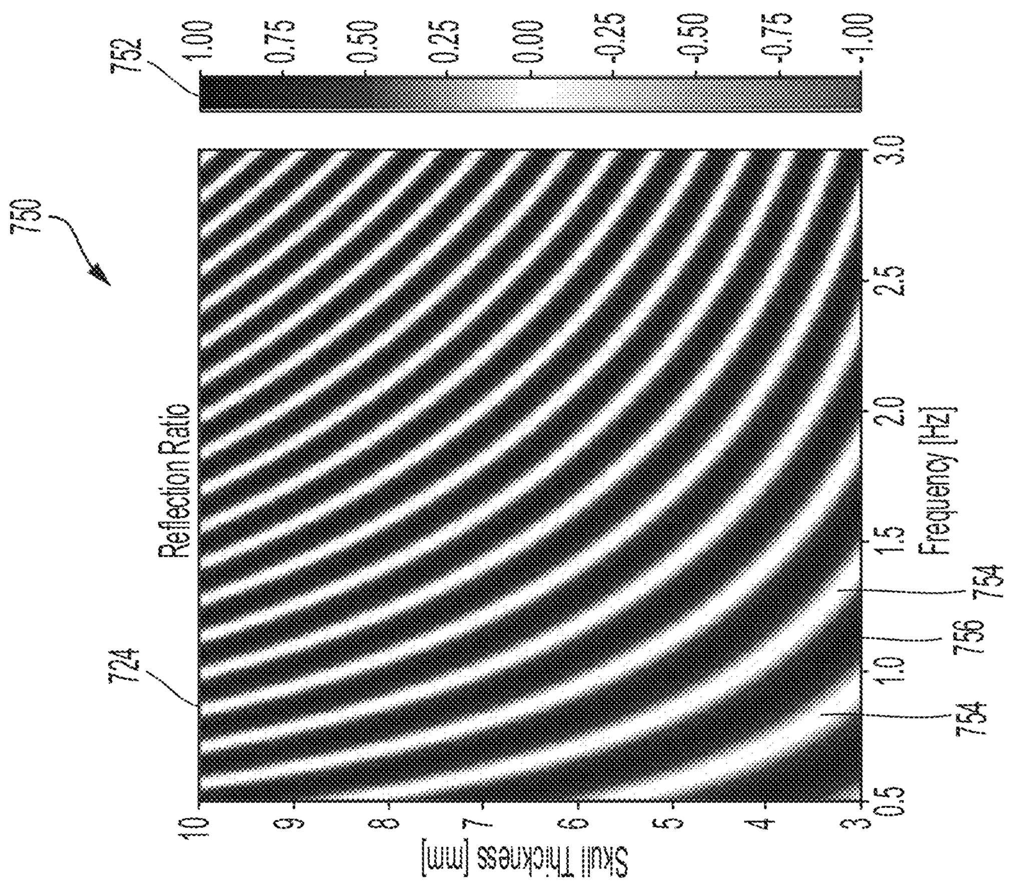
FIG. 14B is a chart showing a reflection ratio as a function of frequency, according to at least one aspect of the present disclosure.
Figure 14A:
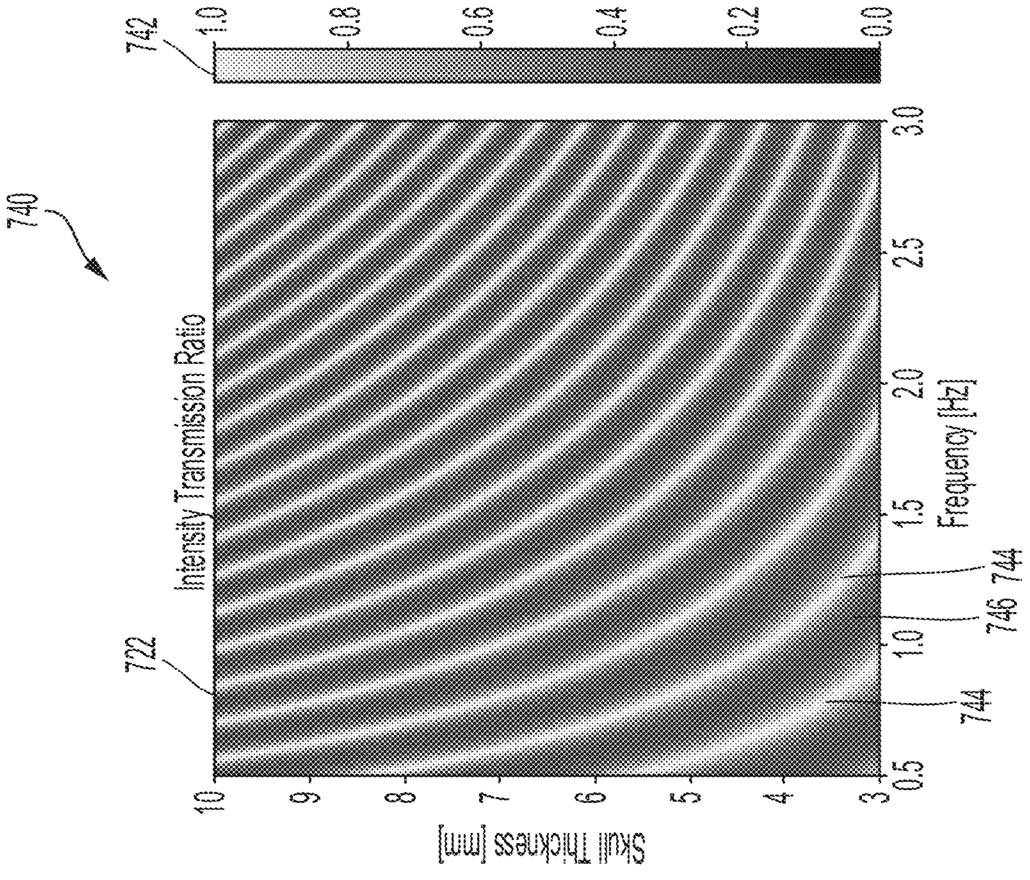
FIG. 14A is a chart showing an intensity transmission ratio as a function of frequency, according to at least one aspect of the present disclosure.

The intensity transmission ratio 722 and the pressure reflection ratio 724 can be functions of both the skull thickness and the frequency. FIG. 14A is a chart 740 showing an intensity transmission ratio 722 as a function of frequency and FIG. 14B is a chart 750 showing a reflection ratio 724 as a function of frequency, according to at least one aspect of the present disclosure. To the right of the chart 740 in FIG. 14A is a scale 742 of the intensity transmission ratio 722 ranging from 0.0 to 1.0 and the right of the chart 750 in FIG. 14B is a scale of the reflection ratio 724 ranging from −1.0 to +1.0. FIGS. 14A and 14B show how the intensity transmission ratio 722 and the reflection ratio 724 change with skull thickness and frequency. Negative reflection ratios can be achieved wherever peak transmission may be occurring. Negative reflection ratios can indicate that the reflected wave can be phase shifted 180° relative to the incident wave. As shown in the chart 740 of FIG. 14A, the intensity transmission ratio 722 has a maximum ratio 744 of about 1.0 and a minimum ratio 746 of about 0.4, which is consistent with the maximum/minimum ratios shown in charts 720, 730 in FIGS. 13A and 13B. The chart 750 shown in FIG. 14B shows that the reflection ratio 724 has a minimum ratio 754 of about 0.0 and a maximum ratio 756 of about 0.8, which is consistent with maximum/minimum ratios shown in the charts 720, 730 in FIGS. 13A and 13B.

Frequencies that are different by an irrational number may make good choices because they can have peak transmissions at different thicknesses. The golden ratio (e.g., the "most irrational number") may be useful in selecting frequencies. It may not be sufficient for selected frequencies' transmission to avoid peaking at the same skull thickness, "t."

It can also be allowable for two frequencies to share a peak transmission at a certain thickness, provided that the shared peak occurs at a skull thickness, "t," outside of the thicknesses expected to occur naturally. If the device can select the best frequency (e.g., the greatest transmission ratio) at each skull thickness, "t," then to get optimal coverage across many skull thicknesses, "t," with a limited number of frequencies can mean to maximize the average transmission ratio of the best frequency across the selected skull thicknesses, "t," or to maximize the minimum transmission ratio of the best frequency within the selected skull thicknesses, "t."

Hair on the patient's head may need to be shaved or shortened to allow for efficient transmission of sound into the brain. Some aspects may allow the hair to remain untouched. A comb-like structure can be able to pass through hair to contact the skull in many locations to transmit sound. The hair may also be wet and matted down to allow for the sound to transmit relatively unimpeded.

Figure 15:
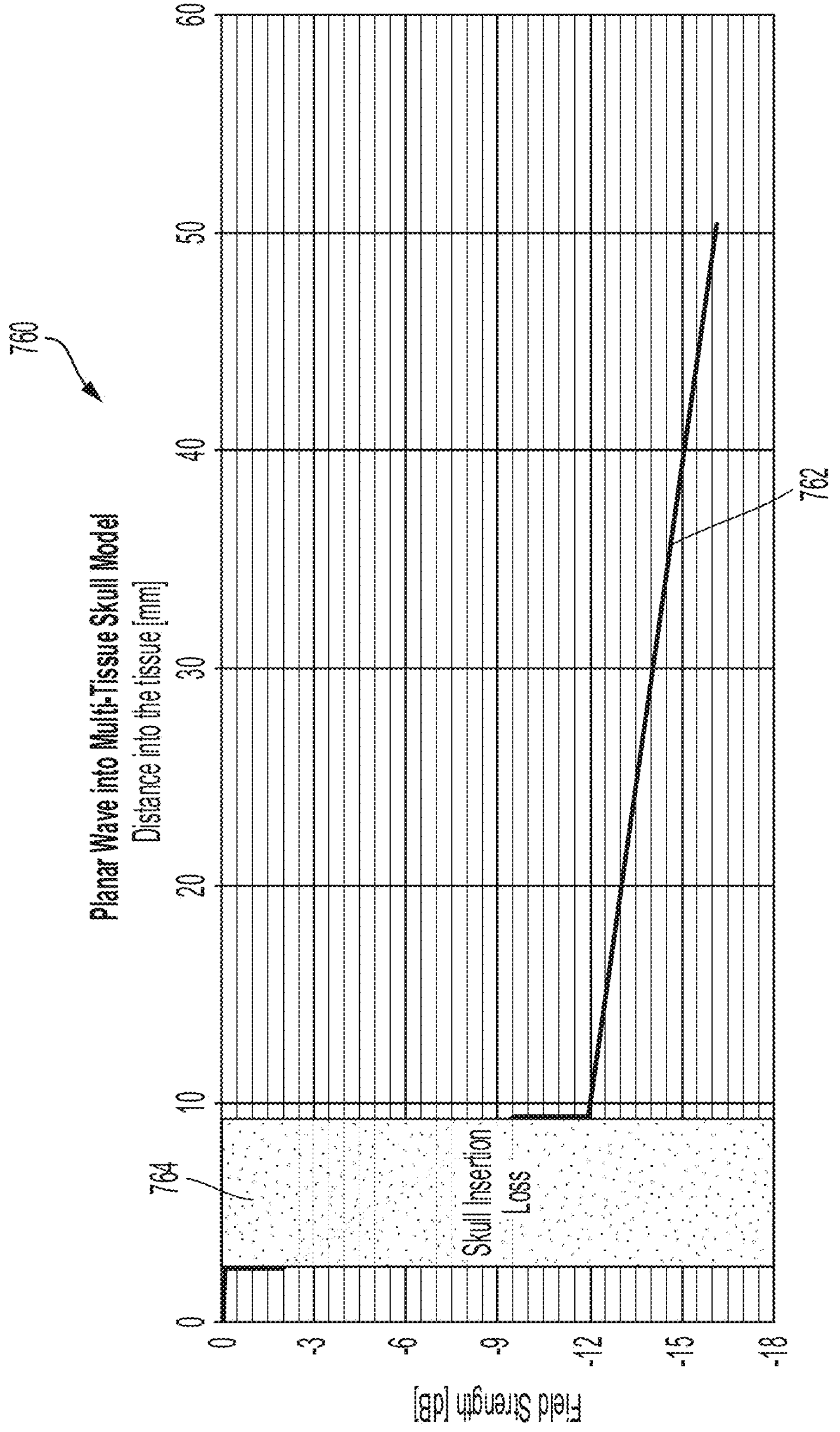
FIG. 15 is a chart showing the field strength of a planar wave into a multi-tissue skull model, according to at least one aspect of the present disclosure.

FIG. 15 is a chart 760 showing the field strength of a planar wave 762 into a multi-tissue skull model, according to at least one aspect of the present disclosure. With reference to FIG. 15, the skull may absorb a large proportion of the ultrasonic energy in a short distance. The insertion loss 764 (the amount of energy that can be lost by adding the skull into the acoustic wave 200) can be centered around 12 dB. Every additional 3 dB worth of loss can correspond to approximately half of the energy being reduced. A 12 dB loss can be equivalent to a sixteenth of the energy introduced at the surface of the skin being left at the surface of the skull. Because of this, the skull may heat up during transcranial sonodynamic therapy.

Table 1 is a summary of the parameters that can be used in the model of the skull. In addition to the intrinsic acoustic properties of the skull, the skin can be assumed to be 2.5 mm thick, and the skull can be assumed to be around 6.8 mm thick. FIG. 15 shows the acoustic intensity in terms of field strength (dB) as a function of distance within the head model. The insertion loss 764 highlighted region emphasizes the jumps of energy lost at the interfaces and steep attenuation within the skull.

TABLE 1

| Parameters Used In The Model Of The Skull<br>Interface Transmission Loss | | | |
|---|---|---|---|
| Interface | Ratio | | dB |
| Skin-Bone | T = 0.650 | | −1.87 |
| Bone-Skin | T − 0.567 | | −2.46 |
| Frequency | 1 MHz | | |
| Attenuation | Skin | −0.5 | dB/(cm-MHz) |
| | Bone | −11.1 | dB/(cm-MHz) |
| | Brain | −1 | dB/(cm-MHz) |
| Acoustic Impedance | Skin | 1.99 | Kg/sec-m$^2$) × 106 |
| | Bone | 7.75 | Kg/sec-m$^2$) × 106 |
| | Brain | 1.6 | Kg/sec-m$^2$) × 106 |

The model uses an average of various human skull thicknesses. The thickness of the "frontal, parietal and occipital bones were (in mm) 6.58, 5.37 and 7.56, respectively, for the male; and 7.48, 5.58 and 8.17, respectively, for the female." As mentioned elsewhere herein, human skulls vary considerably by gender and anatomical location. The model can represent an average amount of attenuation, but thicker sections of skull can have a greater amount of attenuation. In general, every additional 2.7 mm worth of skull can increase the attenuation by 3 dB (a factor of 2).

This model can be based on a simple plane wave model impinging on planar layers of tissue. Each layer of tissue can be assumed to be homogenous and uniform thickness. The effect of the acoustic wavelength (λ) matching with various thicknesses of skull are ignored in this model. It can also be assumed that all reflected waves are lost and do not reenter the brain.

Pichardo et al. investigated the transmission of ultrasound through freshly excised human skulls at various frequencies. They report the ratio of absorbed energy for seven skulls at several locations at the frequencies of 0.270, 0.836, and 1.402 MHz. While they did not measure the energy lost at 1 MHz specifically, their study allows interpolation and estimation that the insertion loss can be centered around 12 dB. Their study also can confirm that the insertion loss can be expected to vary by skull and anatomical location.

Figure 16:
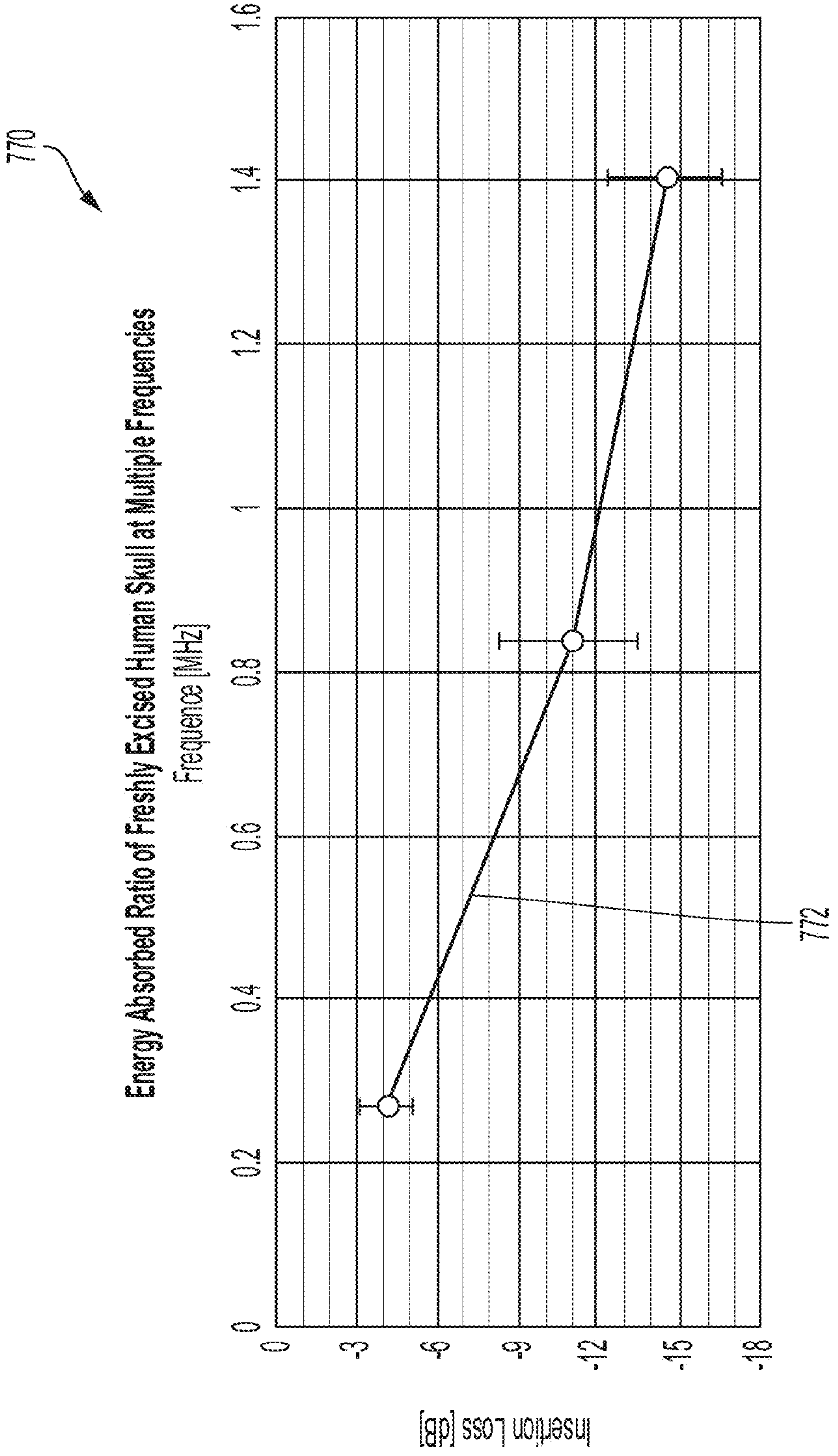
FIG. 16 is a chart showing the energy absorbed ratio of a freshly excised human skull at multiple frequencies, according to at least one aspect of the present disclosure.

FIG. 16 is a chart 770 showing the energy absorbed ratio 772 of a freshly excised human skull at multiple frequencies, according to at least one aspect of the present disclosure. As shown in FIG. 16, Pinton et al. also measured the attenuation at 1 MHz of nine points along an 8 mm thick section of skull bone and found an insertion loss of 12.6±1.33 dB (higher loss due to a thick skull section). Both the simplified head model and measurements taken from different laboratories agree that the insertion loss (the amount of energy lost by adding the skull into the model) can be centered around 12 dB (a factor of 16) with considerable variation.

The energy lost as the sound passes through the skull may be converted into heat primarily in the skull. The temperature of the skull can begin to heat up and, over time, heat can disperse to nearby tissue. Most of the heating can originate at the outer surface of the skull and disperse into the skin and other layers of bone. Above certain intensities, the blood can be unable to transport enough heat away, and the temperature in the bone and skin can rise to unsafe levels. Adding more transducers into the system can decrease the intensity at which this threshold can be reached because the blood can be warmed by each successive transducer it passes and lose its ability to absorb additional heat from the tissue.

There can be several ways to combat the effects of heating. In particular, cooling, intermittent treatment, monitoring, and transducer modulation can be used to reduce the consequences of heating.

Figure 17:
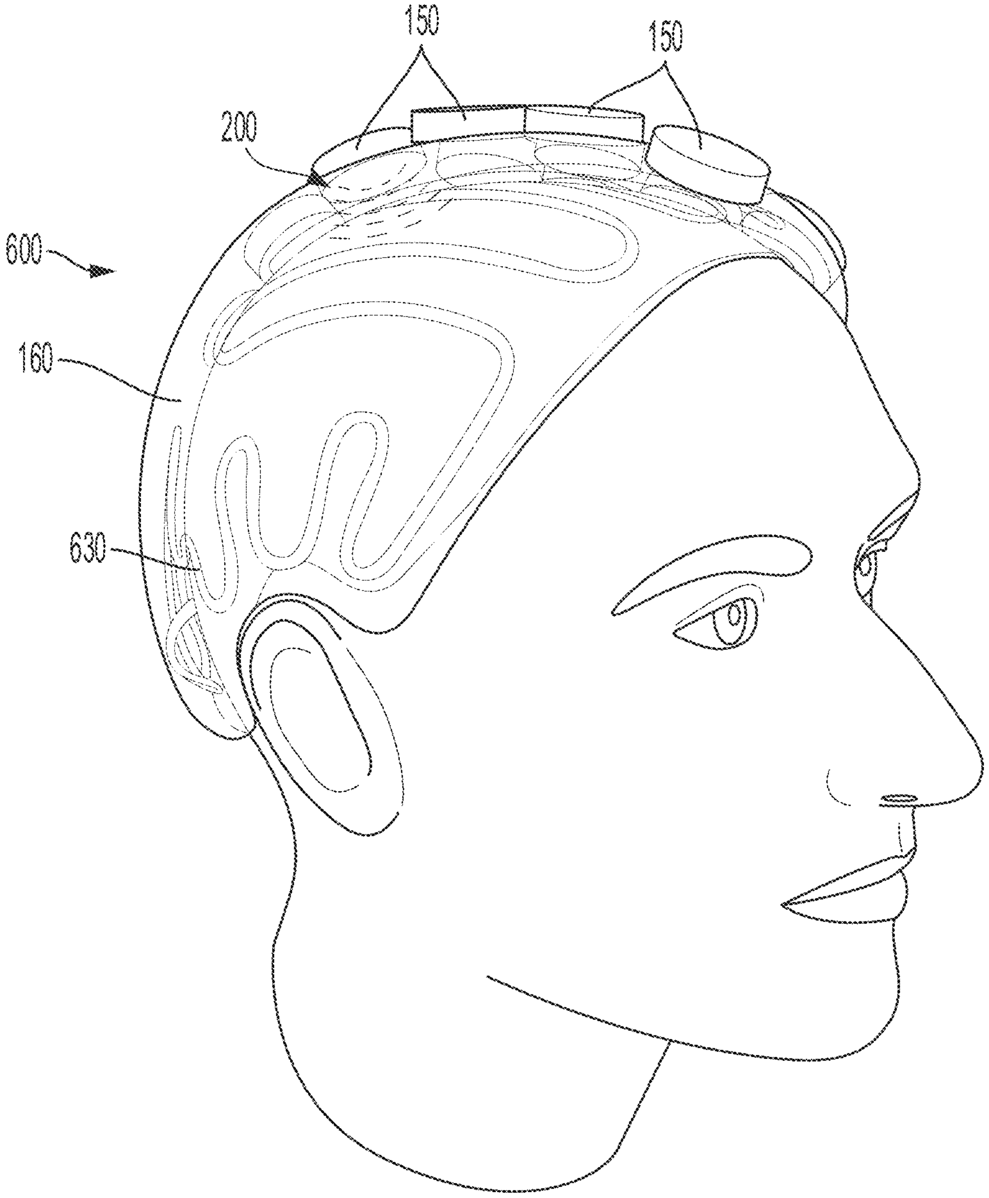
FIG. 17 is a partial cutaway view of a transcranial sonodynamic therapy device placed over the head of a patient showing a partial view of the multiple transducers and a full view of the cooling system, according to at least one aspect of the present disclosure.

FIG. 17 is a partial cutaway view of a transcranial sonodynamic therapy device placed over the head of a patient showing a partial view of the multiple transducers 150 and a full view of a cooling system 600, according to at least one aspect of the present disclosure. The cooling system 600 shown in FIG. 17 may be implemented to keep the temperature of the skull and surrounding tissue within safe levels. A cooling layer (e.g., of water) may be provided between the transducers 150 and the patient's head. The cooling layer can be made of a flexible membrane or balloon that can conform to each patient's head. A large cooling layer may be reusable and, thus, may require cleaning between each use.

The cooling system 600 can be made of a flexible cavity (not shown) with an inlet and an outlet for a coolant such as water to circulate. The head of the patient can be inserted into a concave shape (e.g., a "bowl") with an elastic opening. The elastic opening can seal against the head of the patient. Water can fill up the space between the patient's head and the bowl.

Similar to the single cavity design, water can be circulated to keep the temperature of the water from rising. One advantage of such a system can be that water in the cooling system 600 can be in direct contact with the patient's head. The air around the patient's hair can be removed by the water, which may help couple the ultrasound transducers 150 to the patient's head.

Figure 18:
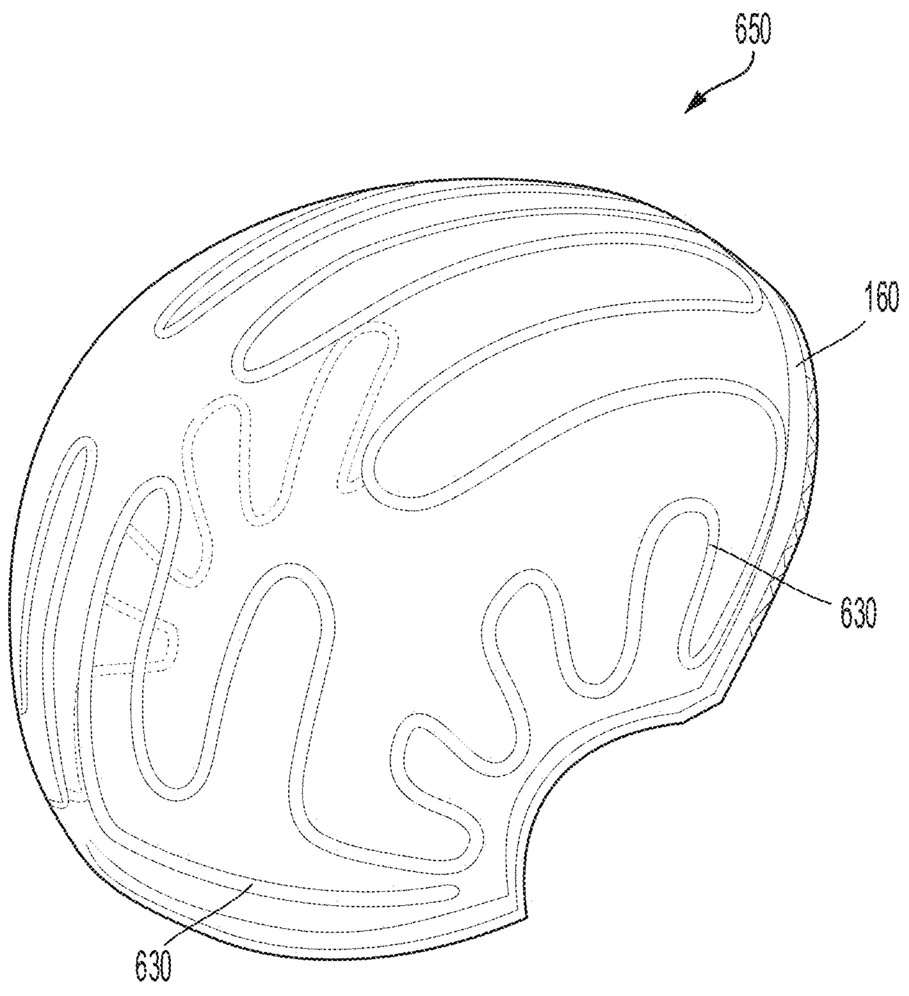
FIG. 18 is perspective view of a patient interface, according to at least one aspect of the present disclosure.

FIG. 18 is perspective view of a patient interface 650, according to at least one aspect of the present disclosure. The cooling system 600 can be a cap 160 with cooling channels 630 distributed throughout. The cap 160 can have one long loop of cooling channels 630, or it can have several independent loops. A system with several cooling loops can be connected to a single inlet and outlet tube via a manifold, or they can be controlled independently. Water or other heat transfer fluid can be circulated through the cooling channels 630 to exchange heat generated either by the transducers 150, the patient's body, or a combination thereof.

Water can flow past all regions of the head that can absorb heat. The water can be pumped to keep the water temperature from rising which would decrease the cooling efficacy of the water. Like patches with multiple transducers 150, each patch may have its own cooling channels 630. The cooling channels 630 can be water-filled tubes that may be larger and heavier than the wires going to the transducers 150. The number of unique cooling channels 630 can be optimized to avoid excessive weight in the cooling layer.

The effect of heating can be readily monitored with temperature sensors and reduced with the fluid cooling system 600. A layer of cool, degassed water between the ultrasonic transducers 150 and the head can serve a dual function of coupling the head to the transducers 150 and controlling the temperature of the skull. Prior to any insonication, the head can be cooled for several minutes by a constant flow of cool water. Once the treatment begins, the temperature of the skull can be monitored continuously, which can modulate the treatment over the entire skull, or it can individually modulate each transducer 150. Even without continuous monitoring of the skull temperature, a safe treatment algorithm can be devised with intermittent treatment and continuous cooling with a margin of safety for all patients. Intermittent treatment can also be more effective than the same effective treatment time done continuously due to the rate limiting step of oxygen diffusion around the sonosensitizer.

It can be likely that just surface temperature monitoring can be necessary. In any case, it can be possible to monitor the temperature throughout the skull using a variety of thermometry of deep-seated tissues. Any surface measurements of temperature may need to be insulated from the cooling layer of water to prevent the probe from being dominated by the cooling layer's effect.

The temperature of the patient's head may need to monitored. If temperature sensors (not shown) are simply placed between the cooling layer and the head, the temperature sensor can be reading some combination of the head temperature and the cooling layer temperature.

There can be several ways that the temperature sensor can be isolated from the temperature of the cooling layer. A layer of insulation can be placed between the cooling layer and each temperature sensor. In such instances, the area around each temperature sensor can receive less or no cooling.

Figure 19:
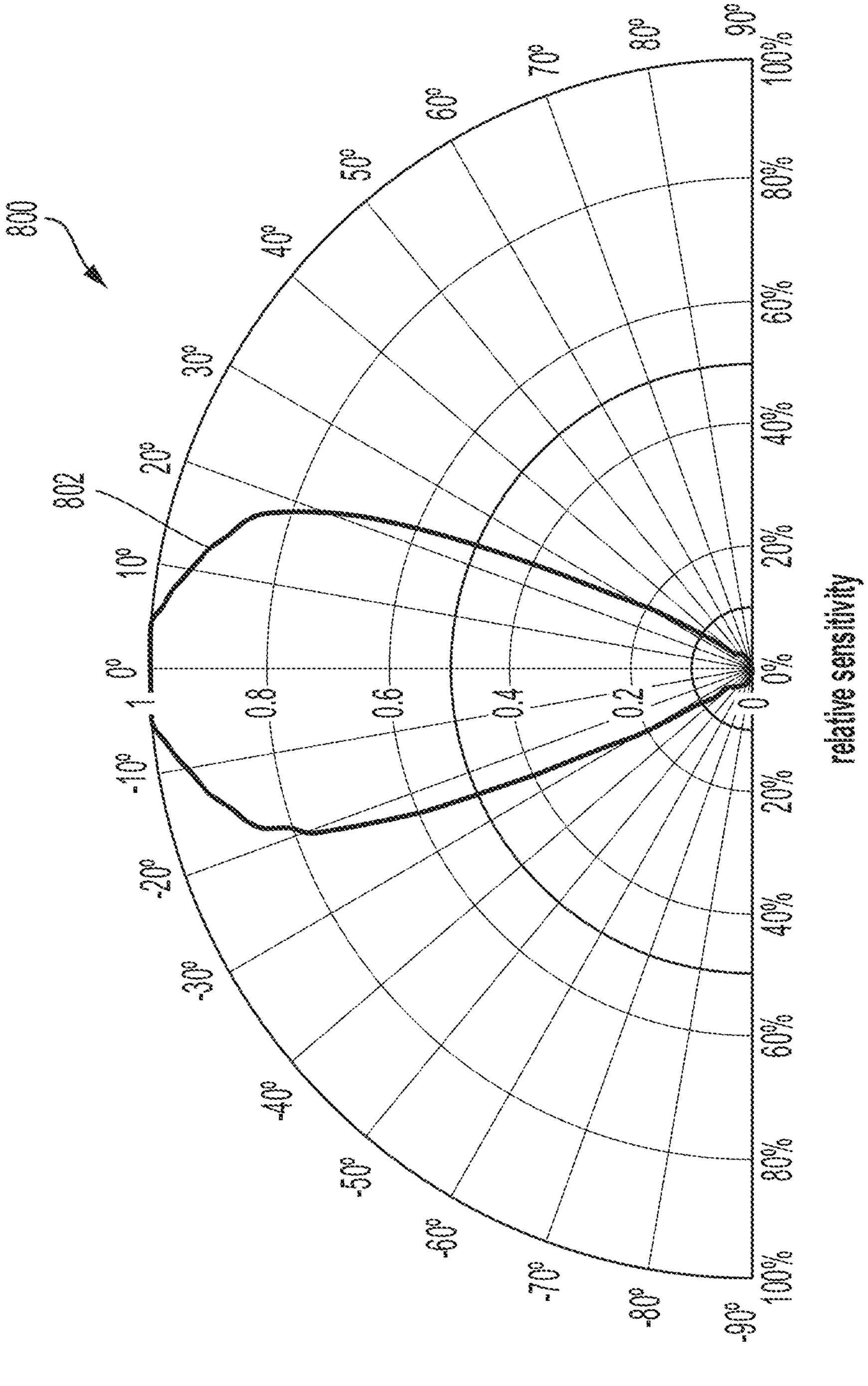
FIG. 19 is a chart showing the relative sensitivity plot of an infrared (IR) temperature sensor, according to at least one aspect of the present disclosure.

FIG. 19 is a chart 800 showing the relative sensitivity plot 802 of an infrared (IR) temperature sensor, according to at least one aspect of the present disclosure. As shown in FIG. 19, a temperature probe (not shown) that measures only in one direction (e.g., unidirectional) can be utilized. An example of a unidirectional temperature sensor can be an IR temperature sensor. IR temperature sensors measure the infrared light being emitted by an object via black body radiation. IR temperature sensors accept radiation coming in from a small range of angles (e.g., an acceptance cone). In this application, one or more IR sensors can be oriented so that the cone of acceptance of each sensor can be facing the patient's head. One or more methods above can be combined to accurately monitor the temperature of the patient's head.

Figure 20:
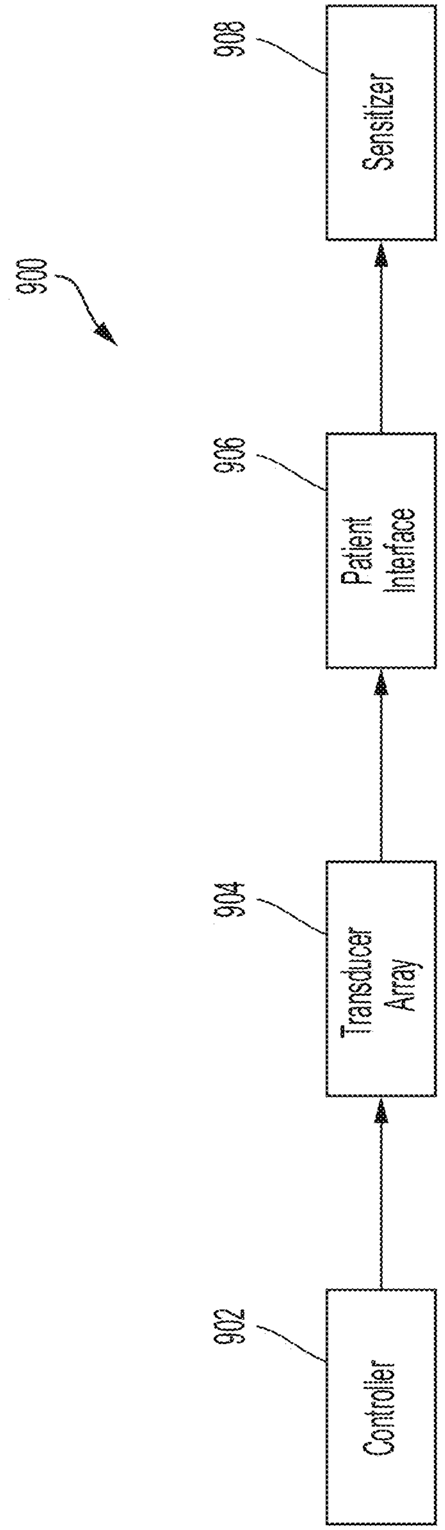
FIG. 20 is a block diagram of a general non-invasive sonodynamic therapy system, according to at least one aspect of the present disclosure.

FIG. 20 is a block diagram of a general non-invasive sonodynamic therapy system 900, according to at least one aspect of the present disclosure. The non-invasive sonodynamic therapy system 900 comprises a controller 902 coupled to an ultrasonic transducer array 904 to control the operation of the ultrasonic transducer array 904 to generate a suitable ultrasonic acoustic wave. The ultrasonic transducer array 904 is coupled to a patient interface 906 to couple the ultrasonic acoustic wave produced by the ultrasonic transducer array 904 to a sensitizer 908 that accumulates in tumor cells within the patient's body. Through a process called sonoluminescence, the ultrasonic acoustic wave produces light that activates the sensitizer 908 and causes necrosis of the tumor cells.

Sonodynamic therapy treatment employs a sensitizer 908 drug that only become cytotoxic upon exposure to ultrasound. Upon activation, sonodynamic therapy drugs generally referred to as "sonosensitisers" produce ROS that generate the cytotoxic effect to kill the tumor cell. Sonodynamic therapy provides much greater tissue depth that can be reached non-invasively by ultrasound as compared to in over photodynamic therapy. In one aspect, the sensitizer 908 may comprise 5-aminolevulinic acid (5-ALA) among other sensitizers 908 such as hematoporphyrin, Rose Bengal, curcumin, titanium nanoparticles, chlorine e6, and any combinations thereof. In addition, the sonodynamic process may comprise injecting microbubbles into the tumor tissue to "seed" cavitation, enabling bubble to accumulate in the tumor tissue, or injecting a drug to oxygenate tumor tissue. The sonodynamic therapy process described herein may be combined with one or more other adjuvant therapies such as chemotherapy, immunotherapy, radiotherapy, and/or HIFU.

The non-invasive sonodynamic therapy system 900 may be employed to treat a variety of tumors and to treat the area around the tumor cavity, whether malignant or nonmalignant. The area around the tumor cavity includes cells that cause the recurrence and eventual mortality in malignant tumors. In one aspect, the non-invasive sonodynamic therapy system 900 may be configured to treat prostate cancer via trans-rectal ultrasound sonodynamic therapy and cervical cancer via trans-vaginal ultrasound sonodynamic therapy, for example.

In one aspect, the controller 902 may be configured to drive the ultrasonic transducer array 904. The controller 902 may be configured to execute one or more than one control algorithm setup/reflection assessment and tune the drive frequency to skull thickness. This can be done automatically. In one aspect, the control algorithm may be configured to pulse or control the "duty cycle" of the ultrasonic transducer array 904 drive waveform to generate high temporal peak acoustic intensity of ultrasonic acoustic waves with low temporal average acoustic intensity sufficient to activate the sensitizer 908 while preventing thermal necrotic death of the tumor cells in the treatment region. In another aspect, the control algorithm may be configured to generate packets of waves that are delayed to overlap the tumor. In another aspect, the control algorithm may be configured to control the intensity of the ultrasonic acoustic wave.

In another aspect, the control algorithm may be configured to control the phase of the ultrasonic acoustic wave. In another aspect, the control algorithm may be configured to randomize the phase of the ultrasonic acoustic wave. Modulating acoustic waves with phase randomization promotes broad consistent coverage across a treatment region where acoustic wavefronts constructively combine at varying pseudo random locations within the treatment region, rather than the exact same location with each cycle. This control scheme provides a more homogeneous treatment region to aid broad consistent treatment coverage and avoid sub therapeutic dead spots in the treatment region. Phase randomization provides additional benefit in adapting to the treatment environment. Repeating the exact same excitation pattern in some types of acoustical environments could lead to the potential for standing waves to form. Standing waves are inherently dangerous as they can deliver unintended treatment energy to the patient. A controller scheme that provides phase randomization of the acoustic waveform can mitigate the risks of repetitive excitation that can lead to standing waves.

A feedback loop may be provided back to the controller 902 to adjust the drive signal to the ultrasonic transducer array 904 based on in situ variables such as tissue depth, tissue thickness, tissue volume, skull thickness, temperature, among other variables. In one aspect, the controller 902 may be located in an ultrasonic generator or may be located elsewhere. In various aspects, in situ variables may include a disease state or an inner body location. The disease state may include alternative treatment ultrasonic transducer probe that is driven differently for each disease state. Examples of feedback loops are described hereinbelow in connection with FIGS. 22-24.

In one aspect, the ultrasonic transducer array 904 may be configured according to the transducers 150, 400, 450 described hereinabove. In various aspects, however, the form factor of the ultrasonic transducer array 904 may be configured to couple ultrasonic acoustic waves in various locations on the patient's body other than the head. For example, the ultrasonic transducer array 904 may be configured to generate ultrasound that activates a sensitizer 908 to treat tumors in the brain, such as glioblastoma, lung, breast, stomach, liver, pancreas, intestines, rectum, colon, vagina, testes, among others, whether the tumors are malignant or nonmalignant.

In various configurations, the ultrasonic transducer array 904 is non-invasive and produces ultrasonic acoustic waves capable of reaching the target tumor cells non-invasively. As described hereinabove, the ultrasonic transducer array 904 may be configured as annular array, 2D grid array, a linear array, and the like, to generate an adaptively focused ultrasonic acoustic wave optimized based on in situ variables such as tissue depth, tissue thickness, tissue volume, skull thickness, among other variables. In other aspects, the ultrasonic transducer array 904 may adaptively focus or adjust the ultrasonic acoustic wave based on pretreatment planning or safety. In one aspect, the controller 902 executes a control algorithm to generate selectively convergent/divergent ultrasonic acoustic waves including adaptive focus for collaborative transducer performance. The ultrasonic acoustic array 904 may be configured to perform transmitter and receiver functions that may be controlled by the controller 902.

The ultrasonic transducer array 904 is coupled to the patient interface 906 to facilitate acoustic coupling of the ultrasonic vibrations generated by the ultrasonic transducer array 904 into the patient's body. The patient interface 906, like the ultrasonic transducer array 904, is non-invasive. In one aspect, the patient interface 906 may be configured to remove air between the ultrasonic transducer array 904 and the patient's body to facilitate acoustic coupling. In one aspect, the patient interface 906 may be configured to remove excess heat from the patient's body. In some configurations, the patient interface 906 may comprise a variety of sensors, such as a temperature sensor, for example. Signals from such sensors may be provided as feedback to the controller 902 (see FIG. 22 for example). Such feedback may be employed to control the ultrasonic transducer array 904 to generate a desired ultrasonic acoustic wave. The patient interface 906 also may include gel or hydrogel layers to improve the acoustical coupling between the ultrasonic transducer array 904 and the patient's body. In one aspect, the patient interface 1022 may be configured to locally apply cooling. In one aspect, the patient interface 1022 may be configured for sensor feedback to the processing unit 902.

Finally, the non-invasive sonodynamic therapy system 900 comprises a sensitizer 908 that may be absorbed by the tumor cells. Sonodynamic therapy requires the combination of the sensitizer 908, such as a sensitizing drug, ultrasound generated by the ultrasonic transducer array 904 coupled into the patient's body by the patient interface 906, and molecular oxygen. Although these components are non-toxic individually, when combined together, a cytotoxic ROS is generated to kill the tumor cells. Sonodynamic therapy may be configured to provide penetration of ultrasound through the patient's body and can be used to treat a wide array of deep and hard to access tumors.

Figure 21:
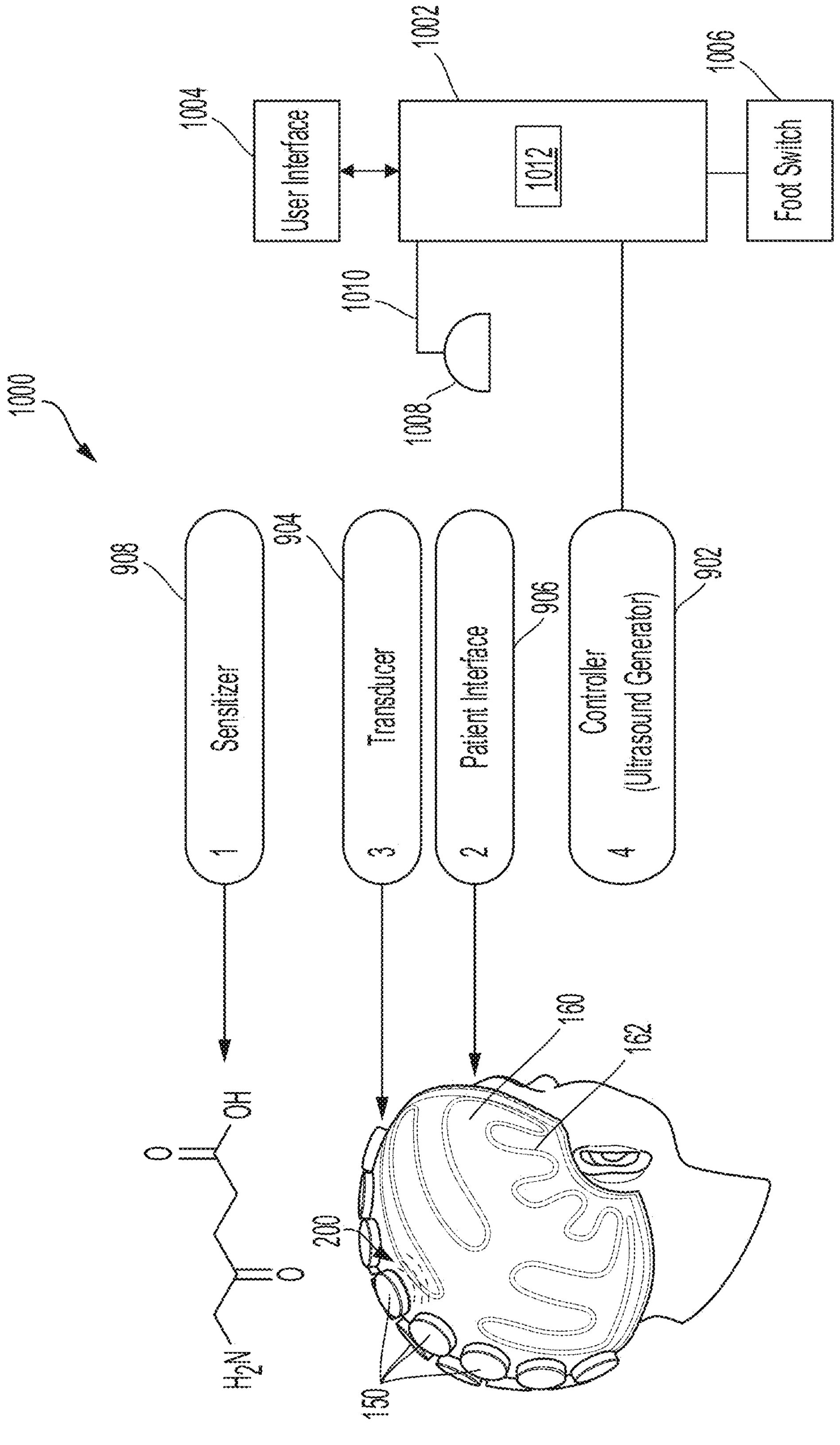
FIG. 21 is an illustrative diagram of the sonodynamic therapy system shown in FIG. 18, according to at least one aspect of the present disclosure.

FIG. 21 is an illustrative diagram 1000 of the sonodynamic therapy system 900 shown in FIG. 20, according to at least one aspect of the present disclosure. In one aspect, the sonodynamic therapy system 900 comprises a controller 902 that may be located in an ultrasonic generator 1002. The ultrasonic generator 1002 comprises a controller 1012, a user interface 1004, a foot switch 1006 for activating the controller 1012, and a cap or helmet 1008 that is placed over the head of the patient. A cable 1010 that carries electrical signals to and from the ultrasonic transducer array 904 couples the transducer array 904 and the ultrasonic generator 1002. The ultrasonic transducer array 904 comprises an array of ultrasonic transducers 150, 400, 450 placed over a patient interface 906 such as the skull cap 160. The ultrasonic generator 1002 drives the ultrasonic transducers 150, 400, 450 to generate an ultrasonic acoustic wave 200 that is coupled into the body of the patient to excite the sensitizer 908 ingested by the patient and absorbed by the tumor cells. The controller 1012 shapes the acoustic wave to achieve a convergent, divergent, or planar acoustic wave, or more complex acoustic waves. As previously described, in one aspect the sensitizer 908 may comprise an ALA sensitizing drug that is activated in a sonoluminescence process, for example.

Figure 22:
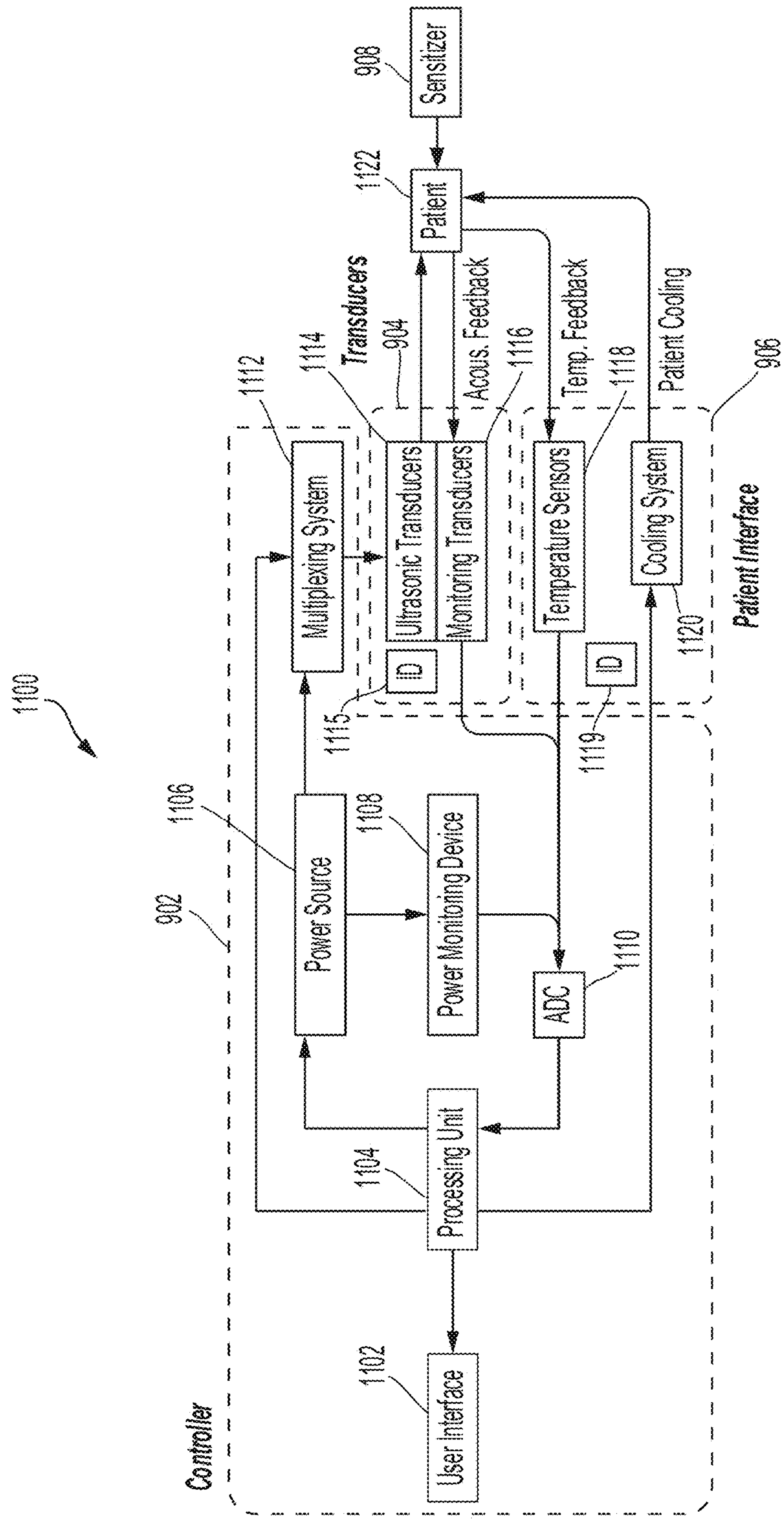
FIG. 22 is a schematic diagram of the sonodynamic therapy system shown in FIGS. 18 and 19, according to at least one aspect of the present disclosure.

FIG. 22 is a schematic diagram 1100 of the sonodynamic therapy system 900 shown in FIGS. 20 and 21, according to at least one aspect of the present disclosure. The controller 902 of the sonodynamic therapy system 900 comprises a user interface 1102 coupled to a processing unit 1104 and configured to receive input from a user and providing output to the user. The processing unit 1104 may be a processor or microcontroller coupled to a memory, a control circuit, or a combination thereof. The ultrasonic transducer array 904 comprises one or more than one ultrasonic transducer 1114 and one or more than one monitoring ultrasonic transducer 1116. It will be appreciated that the same ultrasonic transducer element may be configured to implement an ultrasonic transmitter function as well as a receiver function (see FIG. 24 for example). The patient interface 906 comprises one or more than one temperature sensors 1118 to monitor the temperature of the patient 1122. The patient interface 906 also comprises a cooling system 1120 to reduce the temperature of the patient 1122. In one aspect, the patient interface 906 may be configured to eliminate air gaps between the transducer 1114 and the patient 1122 to enable acoustical coupling.

The processing unit 1104 is configured to execute machine executable instructions to implement various control algorithms as previously described. The processing unit 1104 may comprise a memory to store such machine executable instructions and processing engines to execute the control algorithms. The processing unit 1104 also may be implemented in hardware with digital and analog electronic components. The processing unit 1104 is coupled to a multiplexing system 1112 and a power source 1106 suitable for driving the ultrasonic transducers 1114.

The ultrasonic transducers 1114 are coupled to the body of the patient 1122 to activate the sensitizer 908 administered to the patient 1122. In one aspect, at least one sonosensitizer 908 agent may be configured for preferential accumulation in selective tissue of the patient 1122. Monitoring ultrasonic transducers 1116 monitor acoustic feedback from the patient 1122 and generate signals that are provided as feedback to the processing unit 1104 via an analog-to-digital converter 1110 (ADC). In addition to the acoustic feedback, a power monitoring device 1108 monitors the power source 1106 and provides feedback to the processing unit 1104 through the ADC 1110. The processing unit 1104 controls the ultrasonic transducer drive signals based on the acoustic feedback signal and/or the power monitoring signal to achieve a desired ultrasonic acoustic wave inside the body of the patient 1122. In one aspect, at least one ultrasonic transducer 1114 is configured to output selectively convergent and divergent acoustic waves. The transducer 1114 may be configured in an annular array or a grid array. The transducer 1114 may be configured with multiple electrodes. The transducer 1114 may be configured to receive reflected acoustical signals.

The processing unit 1104 is coupled to the temperature sensors 1118 and receives patient temperature feedback through the ADC 1010. The processing unit 1104 controls the cooling system 1120 based at least in part on the patient temperature feedback signal.

In one aspect, the processing unit 1102 is configured to produce a pulsed acoustical signal with temporal-average intensity output below 8 $W/cm^2$. The processing unit 1102 is adapted to apply amplitude-modulated acoustical signals including constructive interference over a plurality of wave cycles. The processing unit 1102 further may be configured to output packets of acoustic waves at various delayed sequences to provide diffused tissue coverage. The processing unit 1102 may be configured to execute frequency adaptive algorithms to optimize transmission of acoustical signals. The processing unit 1102 may be configured to control phased randomization of acoustical signals.

In various aspects, the present disclosure provides a sonodynamic therapy device comprising a transducer 904, a patient interface 906, and a controller 902 adapted to activate a sensitizer 908 within the body of the patient 1122. The transducer 904 may comprise one or more than one transducer 1114, 1116 where the controller 902 is configured to generate a broadband range of ultrasonic frequencies to drive the transducer 904 and produce divergent, convergent, or planar acoustic waves.

In one aspect, the patient interface 906 is configured to transmit acoustic waves produced by the transducer(s) 904 into the body of the patient 1122 thus acoustically coupling the transducer(s) 904 to the patient 1122. In one aspect, the patient interface 906 provides a cooling system 1120 to remove any excess heat that builds up in the patient 1122 as a of the coupling acoustic energy to the body of the patient 1122. In one aspect, the patient interface 906 may comprise an integral cooling system 1120. The patient interface 906 may comprise a hydrogel cap filled with gel or a water-filled cap with cooling channels. In one aspect, the patient interface 906 comprises one or more than one sensor 1118 to provide feedback to the processing unit 1104 of the controller 902. The sensors 1118 may include, for example, temperature sensors, optical temperature sensors to measure temperature in a particular direction, acoustic sensors, which may include the same transducers 904 used for transmitting acoustic signals. The patient interface 906 may be configured to remove air from the patient interface 906 to improve acoustic coupling between the transducer 904 and the body of the patient 1122. In another aspect, the patient interface 906 may be configured to cool the patient 1122. In yet another aspect, the patient interface 906 may be configured to cool the transducers 904, for example, to keep the transducers at the same temperature to achieve frequency stability.

In one aspect, the patient interface 906 may be adapted and configured to fit various patient anatomies. For example, the patient interface 906 may be adapted and configured to fit patient anatomies for sonodynamic therapy specifically adapted to treat tumors located in the brain, lung, breast, stomach, liver, pancreas, intestines, rectum, colon, vagina, testes, among others, for example. A sonodynamic therapy device may be adapted to wrap around the torso or limb of the patient and/or employed to treat osteosarcoma into the bone. The controller 902 may be adapted to detect either the patient interface 906 or the sonodynamic therapy device such as the transducer 904 or patient interface 906 and select a treatment algorithm to produce acoustic waves optimized for treating the various tumors. The transducer 904 or patient interface 906 may be identified using identification (ID) circuits 1115, 1119 comprising a single-wire serial EEPROM, for example. The ID circuit 1115, 1119 EEPROM may contain both a preprogrammed unique serial number and memory sections. Any or all of the memory sections can be permanently locked by the end-equipment manufacturer to allow tracking of products and identifying attachments. Other identification techniques may include detecting the impedance of the transducer 904 or patient interface 906 and associating the impedance with a treatment algorithm.

In one aspect, the controller 902 is configured to generate electrical drive signals to actuate one or more than one ultrasonic transducer 904 to produce an acoustic wave to activate a sensitizer 908 located within the body of the patient 1122. In one aspect, the electrical drive signals generated by the controller 902 may actuate the one or more than one ultrasonic transducer 904 to produce acoustic waves of varying intensities, amplitudes, or frequencies. In another aspect, the acoustic waves may be amplitude modulated, frequency modulated, phase modulated, continuous, discontinuous, pulsed, randomized, or combinations thereof. In other aspects, the acoustic waves my be produced in a packet of wave cycles, where the number of cycles per packet may be predetermined to achieve a desired outcome that is different from a focused ultrasound pulse, for example. In other aspects, the controller 902 is configured to generate a frequency modulation signal to produce a frequency-modulated acoustic wave. In one aspect, the controller may be configured to generate an intra or inter pulse variation signal that can be used to reduce standing acoustic waves.

In one aspect, the controller 902 is configured to apply an amplitude-modulated acoustic ultrasound signal which constructively interferes over a plurality of wave cycles. In one aspect, the intensity of each of the plurality of acoustic waves remain within a safe range wherein the ultrasound energy carried by each of the plurality of acoustic waves is safe to the tissue of the patient 1122, such as the brain or other body part. In one aspect, the controller 902 may be configured to drive the transducer 904 to generate an amplitude-modulated acoustic wave which produces a constructive wavefront.

In one aspect where the sonodynamic therapy device comprises one transducer 904 and the controller 902 may be configured to generate a drive signal to actuate the transducer 904 to produce a long acoustic ultrasonic wave packet. In one aspect, the controller 902 may be configured to generate a drive signal to actuate the transducer 904 to produce an ultrasonic acoustic wave packet composed of a sinusoidal wave amplitude modulated by a Gaussian pulse (see FIG. 10 for example). In another aspect, the controller 902 may be configured to generate a drive signal to actuate the transducer 904 to produce an ultrasonic acoustic wave packet composed of a sinusoidal wave amplitude modulated by a rectangular pulse. In another aspect, the controller 902 may be configured to generate a drive signal to actuate the transducer 904 to produce an ultrasonic acoustic wave packet composed of a sinusoidal wave amplitude modulated by a triangular pulse. The ultrasonic acoustic wave packet may comprise intra or inter wave packet variation. In one aspect, the controller 902 may be configured to generate a drive signal to actuate the transducer 904 to produce an acoustic ultrasonic pulse. The acoustic wavefronts of the ultrasonic pulse may either converge to focus the ultrasonic energy to a specific region or diverge to spread the ultrasonic energy to a larger region.

In other aspects, where the sonodynamic therapy device comprises two or more transducers 904 and the controller 902 may be configured to generate a drive signal to actuate the two or more transducers 904 to produce acoustic ultrasonic pulses where the individual wavefronts, whether converging or diverging, will meet at the same location at the same time to focus the ultrasonic energy. In one aspect, the controller 902 may adapt the frequency drive for each transducer 904.

Figure 23:
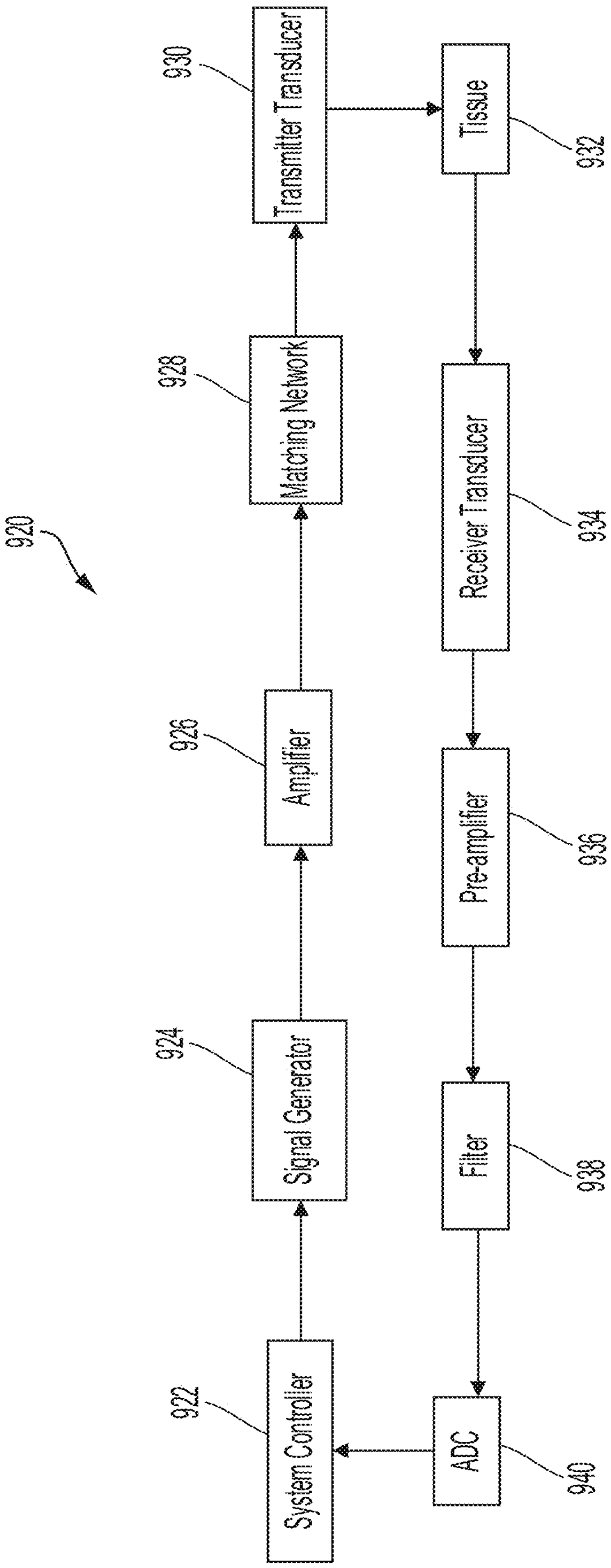
FIG. 23 is a schematic diagram of a sonodynamic therapy system with separate transmitting and receiving transducers, according to at least one aspect of the present disclosure.

FIG. 23 is a schematic diagram of a sonodynamic therapy system 920 with a separate transmitter transducer 930 and receiver transducer 934, according to at least one aspect of the present disclosure. The sonodynamic therapy system 920 comprises a system controller 922 to control a signal generator 924 to generate an electrical signal to drive the transmitter transducer 930. The electrical signal is amplified by an amplifier 926 and the drive signal is coupled to the transmitter transducer 930 by a matching network 928 to maximize power transferred to the transmitter transducer 930. The transmitter transducer 930 transmits an acoustic wave into tissue 932 (e.g., lesions) in the treatment region. A receiver transducer 934 detects acoustic waves emitted by the tissue 932. The output of the receiver transducer 934 is a weak electrical signal that is provided to an electronic pre-amplifier 936 that converts the weak electrical signal into an output signal strong enough to be noise-tolerant and strong enough for further processing such as filtering by a filter 938. The output of the filter 938 is provided to an analog-to-digital converter 940 (ADC) that provides a feedback signal to the system controller 922 in digital form. Based on the feedback signal received from the receiver transducer 934 the system controller 922 can adjust the drive signal applied to the transmitter transducer 930. The adjustment may include adjusting the modulation, strength, frequency, phase, or randomization, of the drive signal, or any combinations thereof. The feedback signal may represent tissue depth, tissue thickness, tissue volume, skull thickness, temperature, distance to the treatment region, or a combination thereof.

Figure 24:
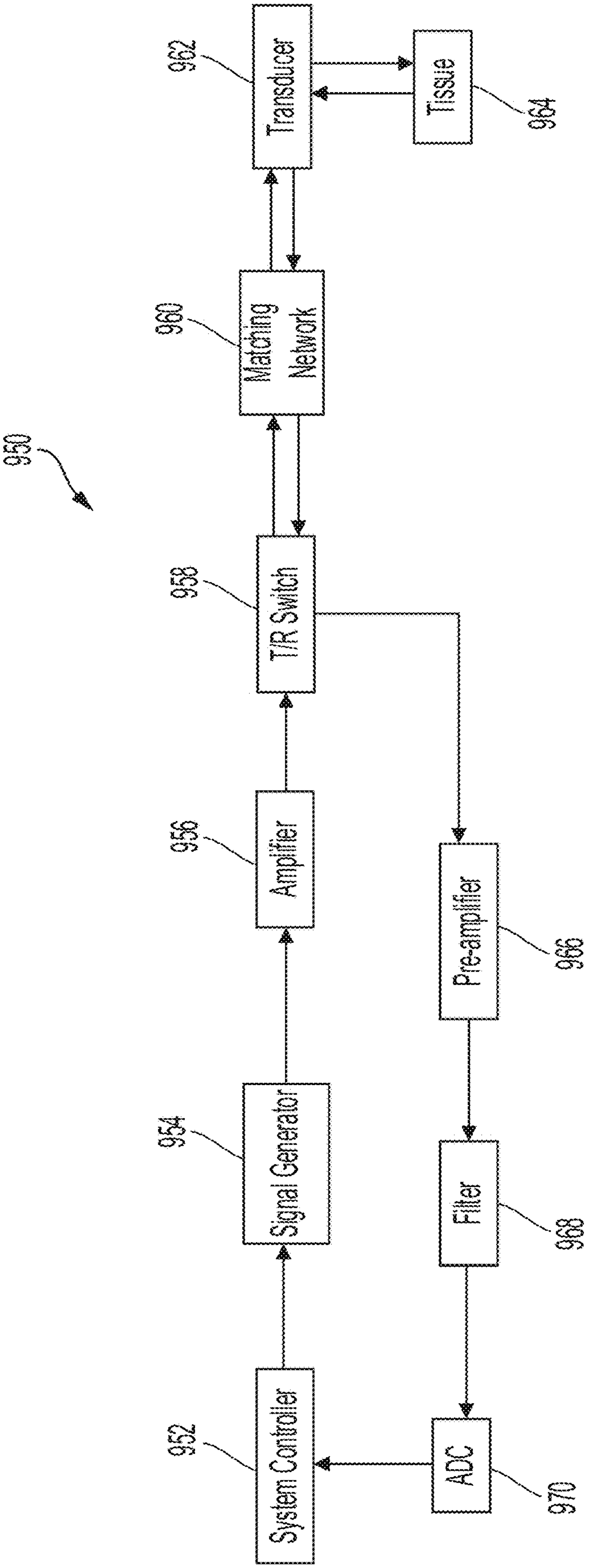
FIG. 24 is a schematic diagram of a sonodynamic therapy system with a single transmitting and receiving transducer, according to at least one aspect of the present disclosure.

FIG. 24 is a schematic diagram of a sonodynamic therapy system 950 with a single transmitting and receiving transducer 962, according to at least one aspect of the present disclosure. The sonodynamic therapy system 950 comprises a system controller 952 to control a signal generator 954 to generate an electrical signal to drive the transducer 962 in transmitter mode. The electrical signal is amplified by an amplifier 956 and is applied to a transmitter/receiver (T/R) switch 958. When the transducer 962 is in transmitter mode, the T/R switch 958 couples the drive signal to the transducer 962 via a matching network 960 to optimize power transferred to the transducer 962. In transmitter mode, the transducer 962 transmits an acoustic wave into tissue 964 (e.g., lesions) in the treatment region. In receiver mode, the transducer 962 detects acoustic waves emitted by the tissue 964. The output of the transducer 962 is a weak electrical signal that is coupled to the T/R switch 958 by the matching network 960. The T/R switch 958 provides the weak electrical signal to an electronic pre-amplifier 966 that converts the weak electrical signal into an output signal strong enough to be noise-tolerant and strong enough for further processing such as filtering by a filter 968. The output of the filter 968 is provided to an ADC 970 that provides a feedback signal to the system controller 952 in digital form. Based on the feedback signal received from the transducer 962 in receiver mode, the system controller 952 can adjust the drive signal applied to the transducer 962 in transmitter mode. The adjustment may include adjusting the modulation, strength, frequency, phase, or randomization, of the drive signal, or any combinations thereof. The feedback signal may represent tissue depth, tissue thickness, skull thickness, temperature, distance to the treatment region, or a combination thereof.

Having described various aspects of a sonodynamic therapy system 920, 950, 1100 and components of the sonodynamic therapy system 920, 950, 1100, the disclosure now turns to a description of a sonodynamic therapy process that can be implemented with the sonodynamic therapy systems 920, 950, 1100 described hereinabove. For conciseness and clarity of disclosure, a sonodynamic therapy process according to FIGS. 25-31 hereinbelow will be described in connection with FIGS. 20-24.

Figure 25:
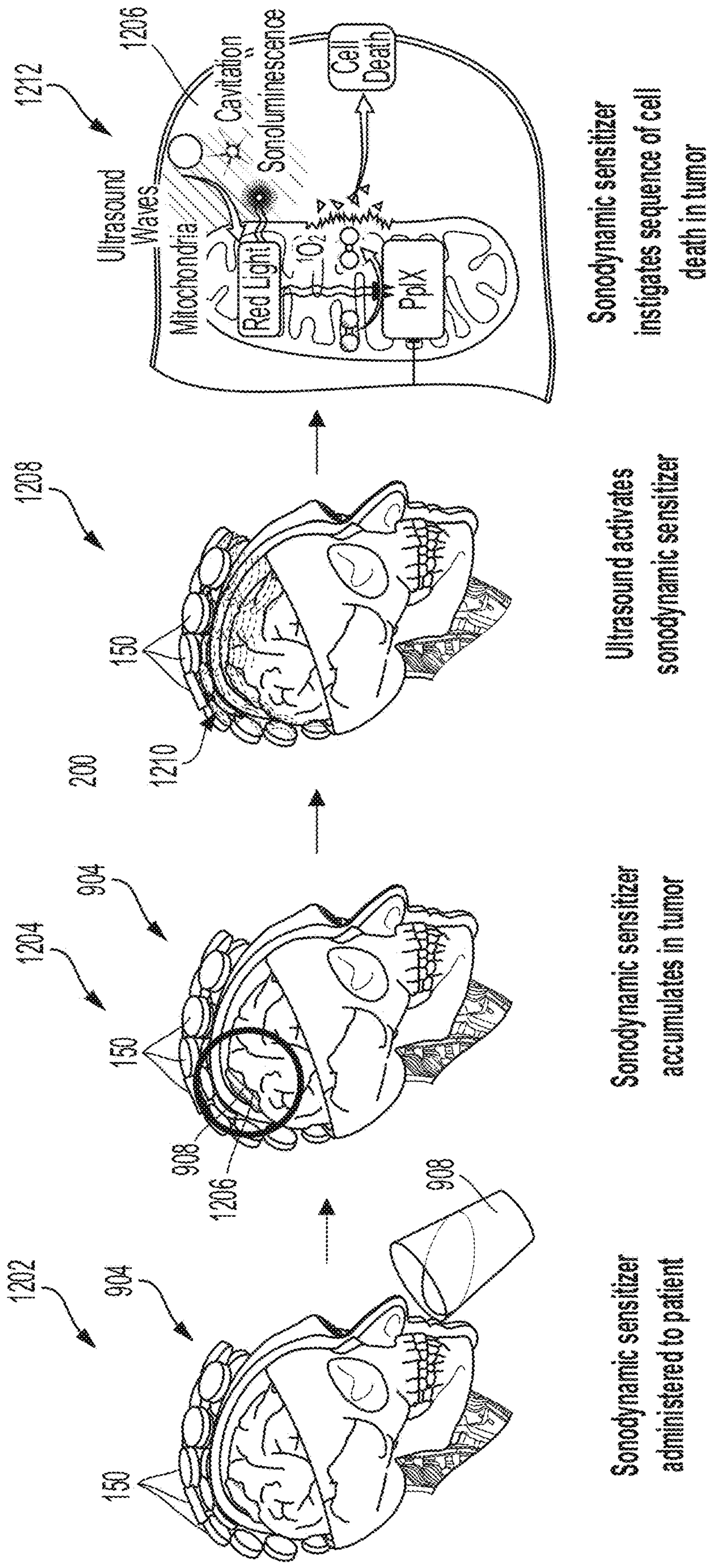
FIG. 25 is an overview of a sonodynamic therapy process, according to at least one aspect of the present disclosure.

FIG. 25 is an overview of a sonodynamic therapy process 1200, according to at least one aspect of the present disclosure. In a first phase 1202 of the sonodynamic therapy process, the patient is administered a sonodynamic sensitizer 908 as described herein, and dons an ultrasonic transducer array 904 comprising a plurality of ultrasonic transducers 150. The sonodynamic sensitizer 908 may be administered orally or through other natural orifices, by injection, intravenously, topically, or other suitable technique. In a second phase 1204 of the sonodynamic therapy process, the sonodynamic sensitizer 908 accumulates in tumor cells 1206. In a third phase 1208 of the sonodynamic therapy process 1200, an ultrasound acoustic wave 1210 generated by the ultrasonic generator 1002 activates the sonodynamic sensitizer 908. In a fourth phase 1212 of the sonodynamic therapy process 1200, the sonodynamic sensitizer 908 instigates a sequence of death of a tumor cell 1206.

Figure 26:
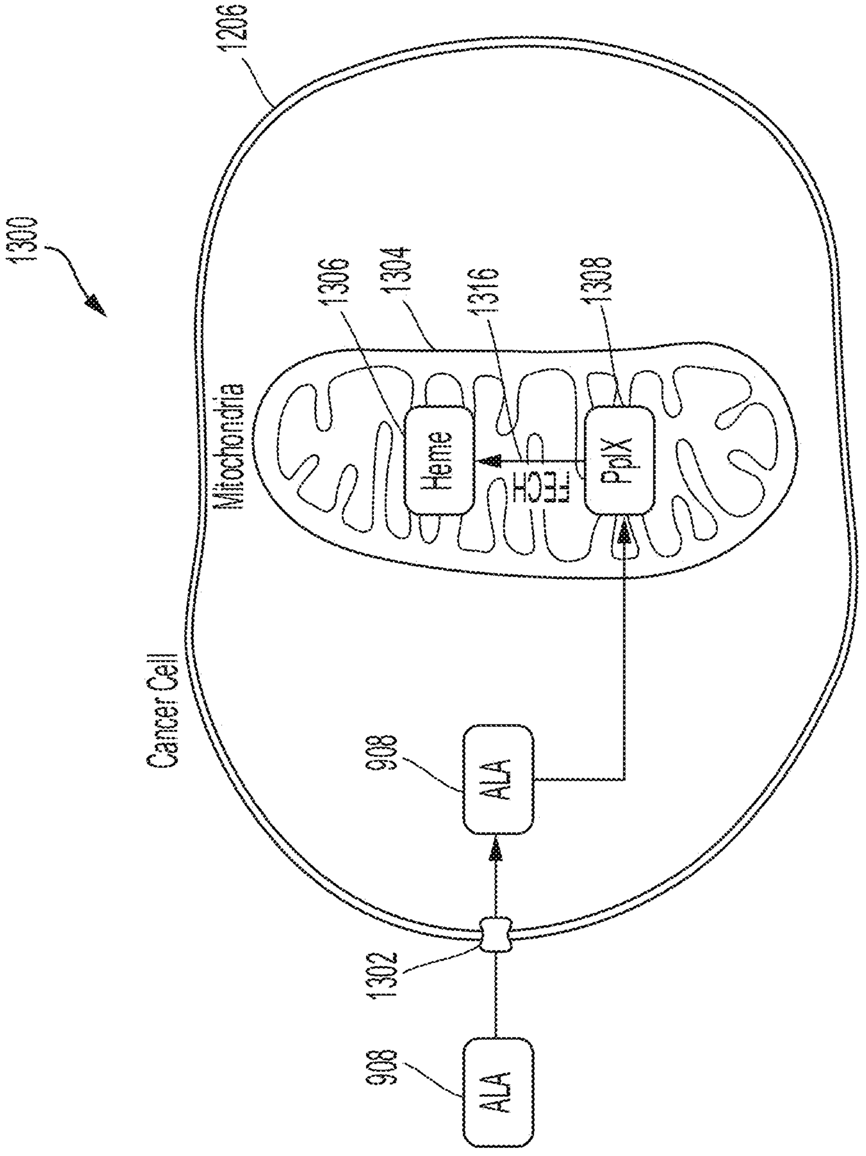
FIG. 26 is a diagram of a cancer cell illustrating the initial stage of selective accumulation of a sensitizer, according to at least one aspect of the present disclosure.

FIG. 26 is a diagram 1300 of a tumor cell 1206 illustrating the initial stage of selective accumulation of a sensitizer 908, according to at least one aspect of the present disclosure. In the illustrated example, the sensitizer 908 is absorbed 1302 into the mitochondria 1304 of the cancer cell 1206. The patient is administered 5-ALA, pro drug sensitizer 908, orally, which puts the heme 1306 biosynthesis pathway 1316 into overdrive. In general, the body's natural feedback mechanism prevents the production of too much heme 1306. Heme 1306 will result in lower activity of the aminolevulinic acid synthase (ALAS) enzyme which produces 5-ALA endogenously. By introducing the sensitizer 908 exogenously, heme 1306 biosynthesis keeps producing even though the ALAS enzyme is inactivated. As a result, protoporphyrin IX 1308 (PpIX) accumulates preferentially in many types of cancer cells 1206 including glioblastoma multiforme (GBM). PpIX 1308 is a catalyst that converts dissolved molecular oxygen into ROS by absorbing photons. Protoporphyrin IX 1308 is in the same class of molecules as chlorophyll (i.e., porphyrins), and is capable of converting light into chemical energy.

Figure 27:
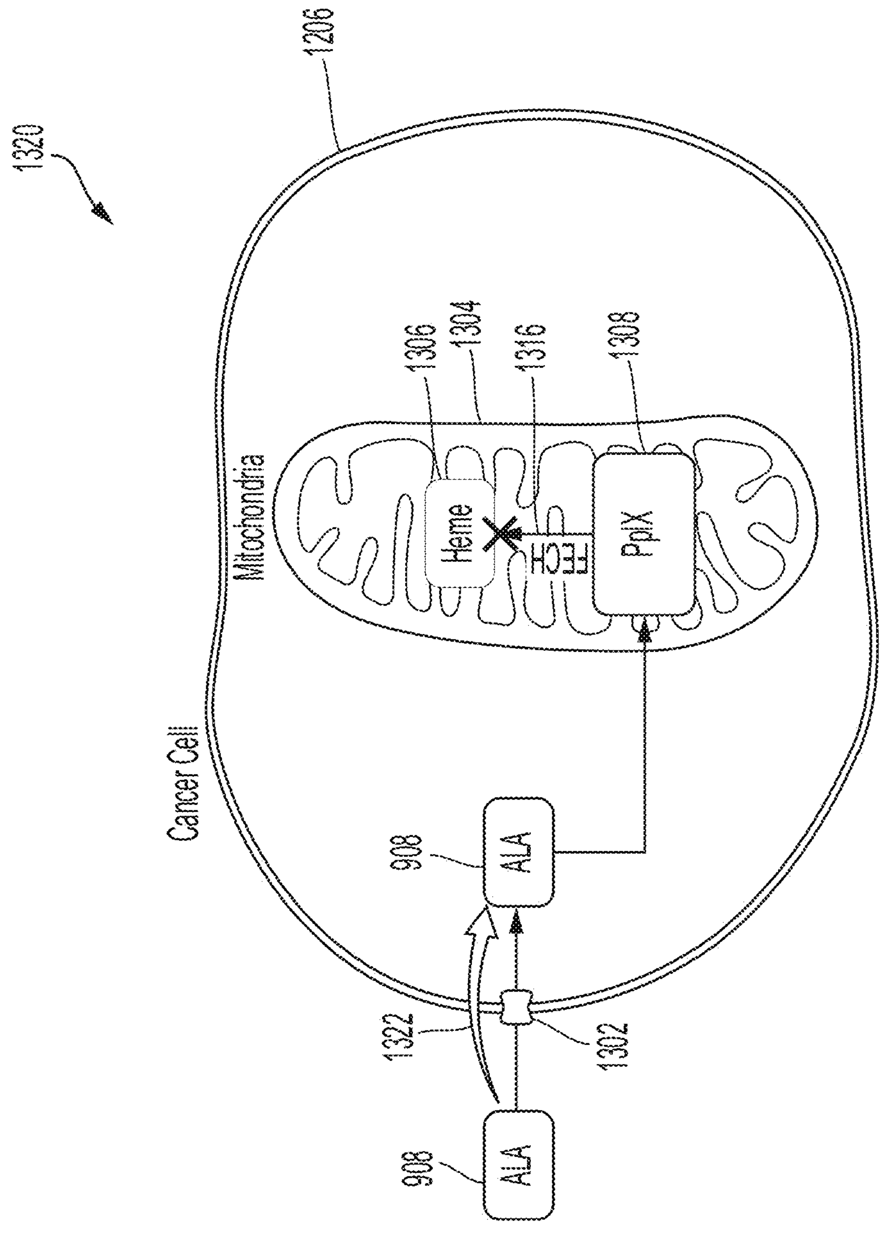
FIG. 27 is a diagram of the cancer cell illustrating the increased selective accumulation of a sensitizer, according to at least one aspect of the present disclosure.

FIG. 27 is a diagram 1320 of the cancer cell 1206 illustrating the increased selective accumulation 1322 of the sensitizer 908, according to at least one aspect of the present disclosure. As shown in FIG. 27, the PpIX 1308 is an active compound and the second to last intermediate product in the heme 1306 biosynthesis pathway 1316. The accumulation of PpIX 1308 in the cancer cell 1206 mitochondria 1304 is due to increased accumulation 1322 of the 5-ALA sensitizer 908 and reduced conversion of PpIX 1308 into heme 1306 (reduced expression of ferrochelatase).

Figure 28:
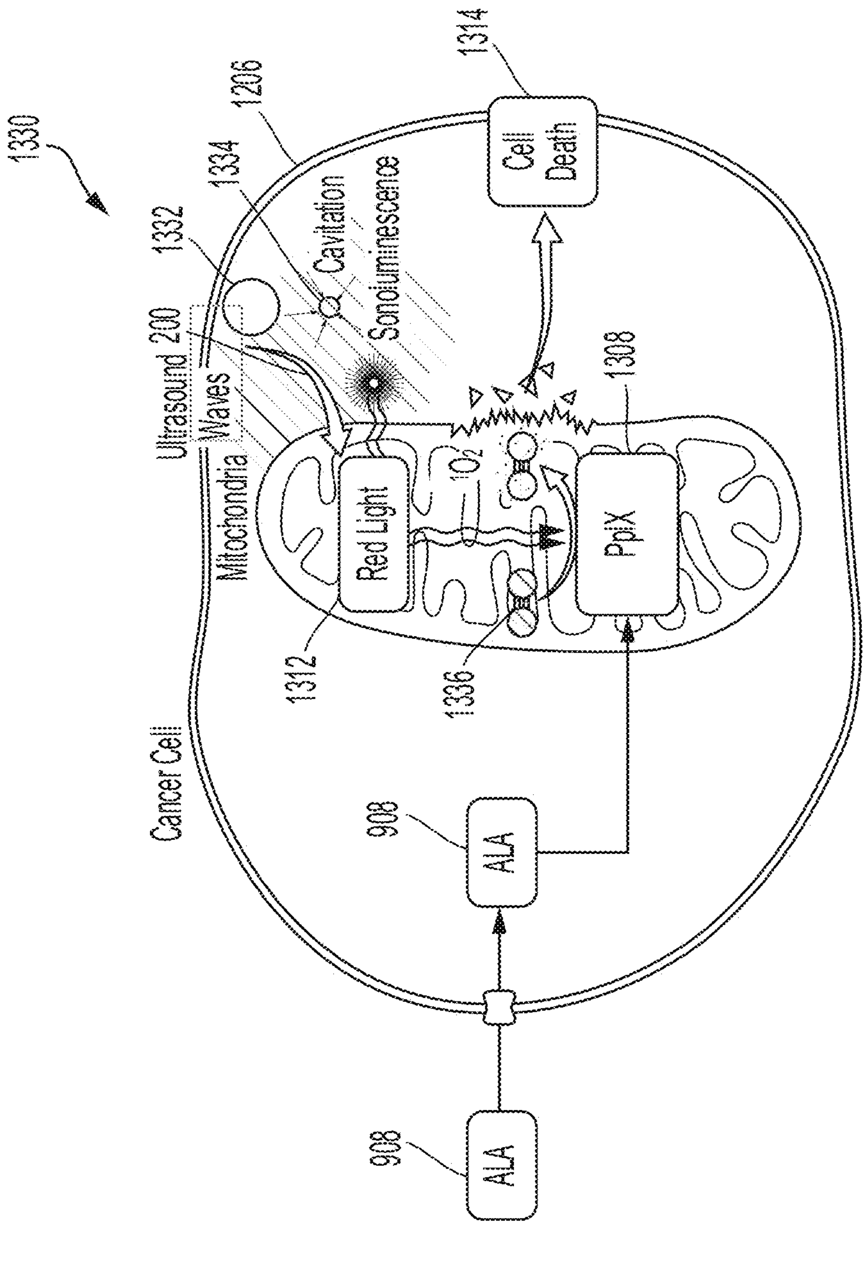
FIG. 28 is a diagram of the cancer cell shown in FIGS. 24 and 25 undergoing sonodynamic therapy, according to at least one aspect of the present disclosure.

FIG. 28 is a diagram 1330 of the cancer cell 1206 shown in FIGS. 26 and 27 undergoing sonodynamic therapy, according to at least one aspect of the present disclosure. The ultrasonic transducer 904 generates an ultrasound acoustic wave 200 that penetrates the cancer cell 1206 and the mitochondria 1304. The ultrasound acoustic wave 200 produces light 1312 through a process called sonoluminescence. Sonoluminescence occurs when the ultrasound acoustic wave 200 collapses fluid bubbles 1332 causing cavitation 1334 and produces light 1312 in the process. The production of light 1312 happens far away from the ultrasonic transducer 904. The light 1312 produced through sonoluminescence activates the PpIX 1308 to produce ROS 1336. Sonoluminescence can occur anywhere the intensity of the ultrasound acoustic wave 200 is sufficient, which allows sonodynamic therapy to treat much deeper than photodynamic therapy. The ROS 1336 species cause oxidative stress which results in the cancer cell 1206 undergoing programmed cell death 1314 (apoptosis), which is the same as photodynamic therapy.

Figure 29:
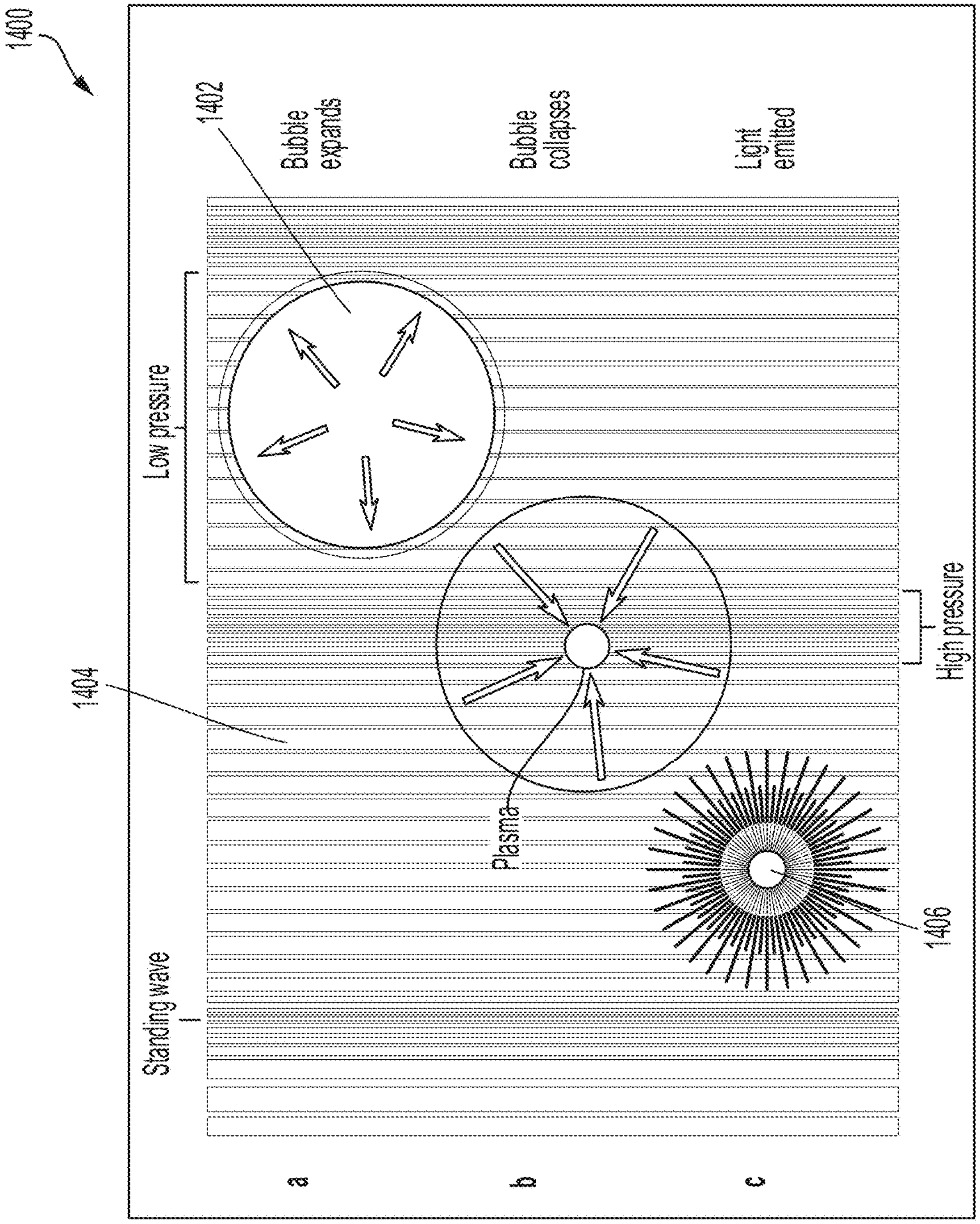
FIG. 29 is a diagram illustrating the process of sonoluminescence, according to at least one aspect of the present disclosure.

FIG. 29 is a diagram 1400 illustrating the sonoluminescence process, according to at least one aspect of the present disclosure. The diagram 1400 can be found in Detlef Lohse, Sonoluminescence, Inside a micro-reactor, Nature volume 418, pages 381-383 (2002), which is incorporated herein by reference. In a standing ultrasonic acoustic wave 200, at low sound-wave pressure, a gas bubble 1402 expands dramatically, until an increase in sound-wave pressure triggers a collapse of the gas bubble 1402. As the temperature inside the gas bubble 1402 soars to over 10,000 K, the gas in the bubble 1402 becomes partly ionized, forming a plasma 1404. Finally, recombination of electrons and ions results in light emission 1406.

Figure 30:
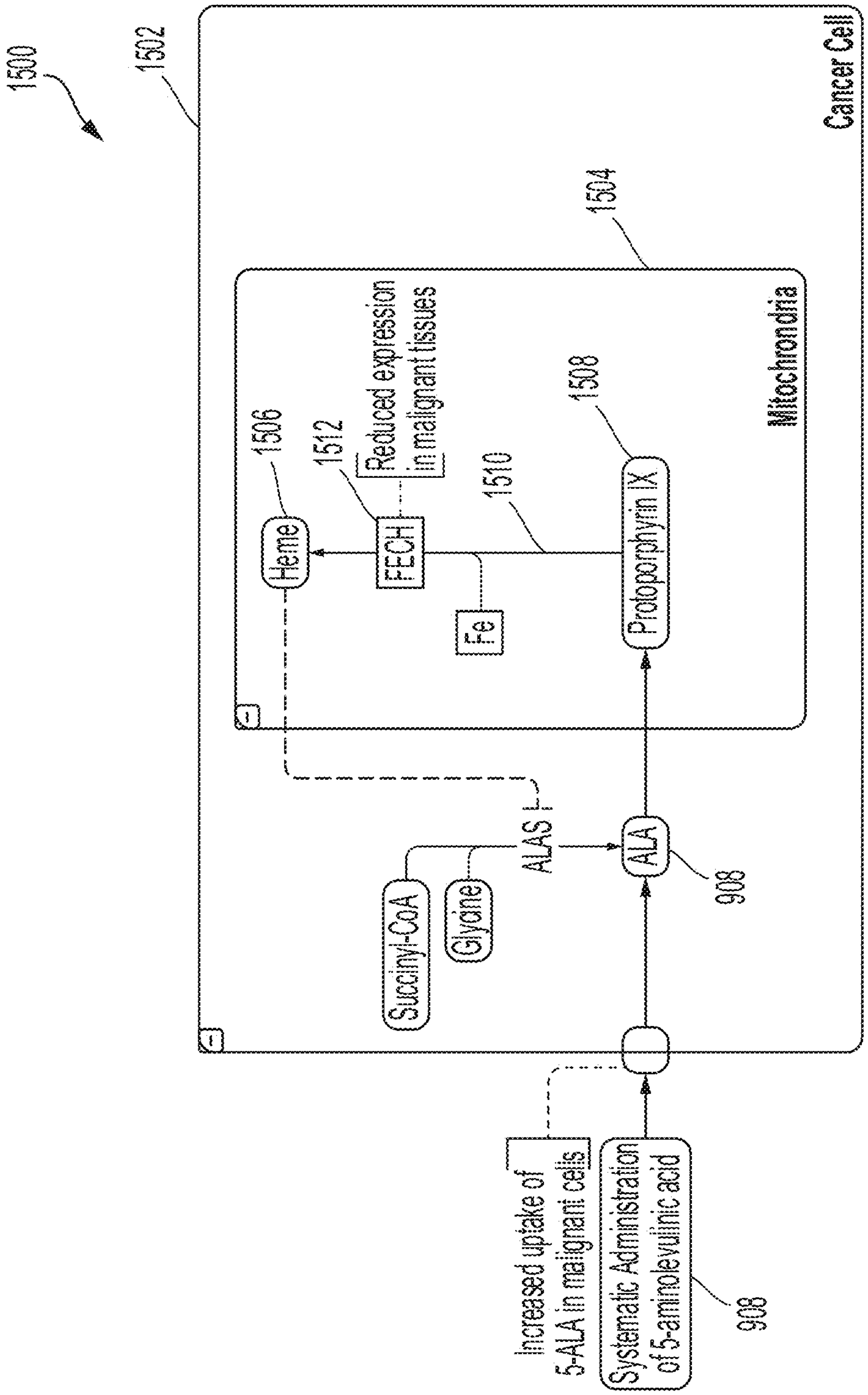
FIG. 30 is a schematic diagram of a cancer cell illustrating the selective accumulation of a sensitizer, according to at least one aspect of the present disclosure.

FIG. 30 is a schematic diagram 1500 of a cancer cell 1502 illustrating the selective accumulation of a sensitizer 908, according to at least one aspect of the present disclosure. In the illustrated example, the 5-ALA sensitizer 908 is systematically administered into the cancer cell 1502 and is absorbed into the mitochondria 1504 of the cancer cell 1502.

The 5-ALA sensitizer 908 is administered to the patient orally, which puts the heme 1506 biosynthesis pathway into overdrive. The natural feedback mechanism of the patient's body prevents the production of too much heme 1506. Heme 1506 will result in lower activity of the aminolevulinic acid synthase (ALAS) enzyme which produces 5-ALA endogenously. By introducing the ALA sensitizer 908 exogenously, heme 1506 biosynthesis keeps producing even though the ALAS enzyme is inactivated. As a result, PPIX 1508 accumulates preferentially in many types of cancer cells 1502 including glioblastoma multiforme (GBM).

The PpIX 1508 is an active compound and the second to last intermediate product in the heme 1506 biosynthesis pathway 1510. The accumulation of PPIX 1508 in the cancer cell 1502 mitochondria 1504 is due to increased uptake of the 5-ALA sensitizer 908 and reduced conversion of PpIX 1508 into heme 1506 reduced expression of ferrochelatase 1512.

The PpIX 1508 is a catalyst that converts dissolved molecular oxygen into ROS by absorbing photons. Protoporphyrin IX 1508 is in the same class of molecules as chlorophyll (i.e., porphyrins), and is capable of converting light into chemical energy.

Figure 31:
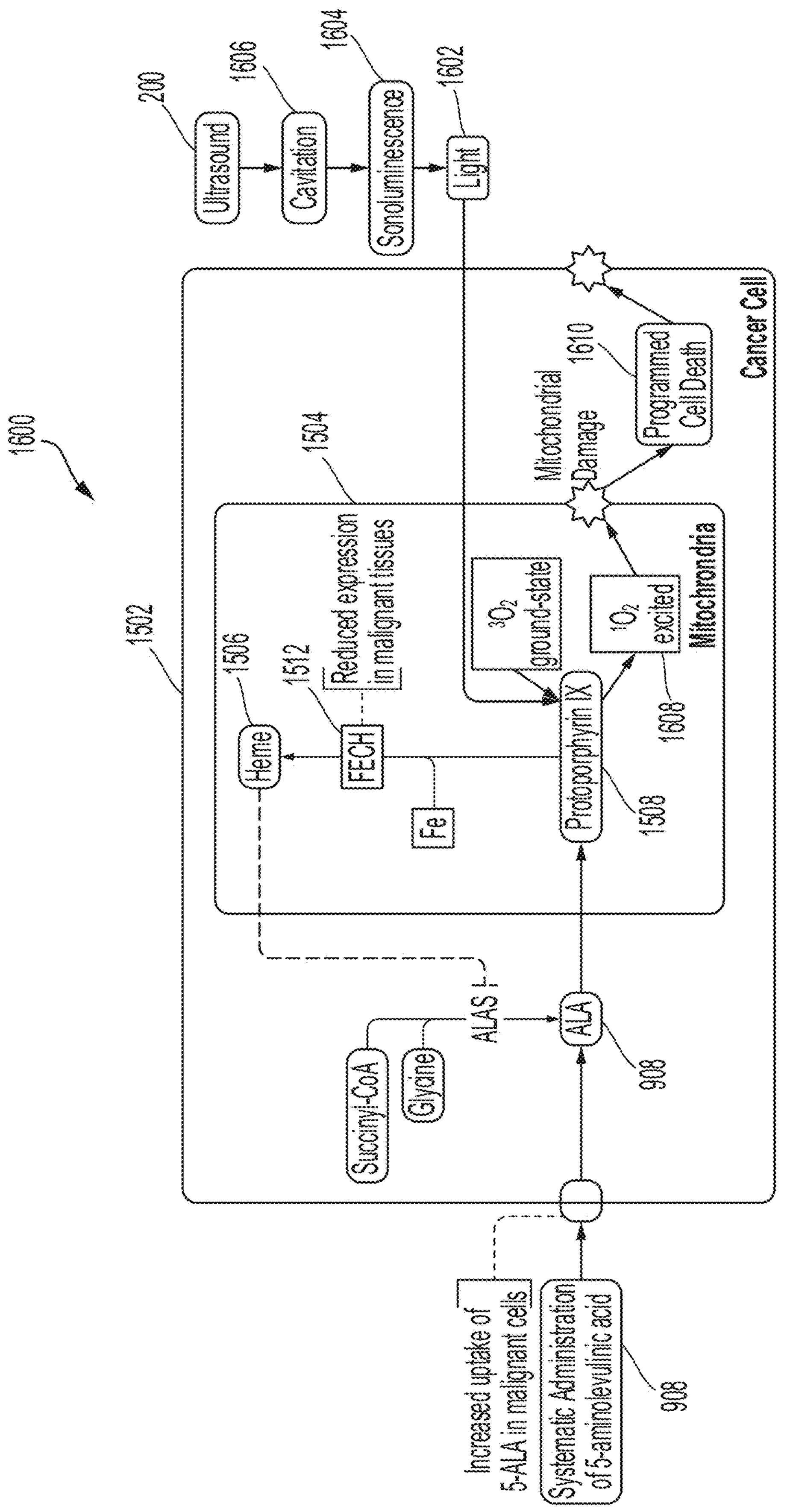
FIG. 31 is a schematic diagram of the cancer cell shown in FIG. 28 undergoing sonodynamic therapy, according to at least one aspect of the present disclosure.

FIG. 31 is a schematic diagram 1600 of the cancer cell 1502 shown in FIG. 30 undergoing sonodynamic therapy, according to at least one aspect of the present disclosure. The ultrasonic transducer 904 generates an ultrasound acoustic wave 200 that penetrates the cancer cell 1502 and the mitochondria 1504. The ultrasound acoustic wave 200 produces light 1602 through cavitation 1606 and a process called sonoluminescence 1604. The production of light 1602 happens far away from the ultrasonic transducer 904. The light 1602 produced through sonoluminescence 1604 activates the PPIX 1508 to produce ROS 1608. Sonoluminescence 1604 can occur anywhere the intensity of the ultrasound acoustic wave 200 is sufficient, which allows sonodynamic therapy to treat much deeper than photodynamic therapy. The ROS 1608 species cause oxidative stress which results in the cancer cell 1502 undergoing programmed cell death 1610 (apoptosis), which is the same as photodynamic therapy.

The interaction of acoustic waves 200 with an aqueous medium may result in cavitation 1606. Cavitation 1606 involves nucleation, growth, and implosive collapse of gas-filled bubbles, under the appropriate ultrasound conditions. In sonoluminescence 1604, inertial cavitation 1606 involves the growth of gas bubbles to a near resonance size and expanding to a maximum before collapsing violently. The energy released by this implosion results in temperatures of up to 10,000 K and pressures of up to 81 MPa in the surrounding microenvironment. Such extreme temperatures and pressures at the point of implosion create a sonochemical reactor. Cavitation 1606 generates ROS 1608 in sonodynamic therapy under two mechanisms of action.

One possible mechanism of action is sonoluminescence 1604. This is process upon which light 1602 is generated upon exposure of the cancer cell 1502 energy produced by the acoustic wave 200. Another possible mechanism of action may be pyrolysis. This is a process whereby localized temperature elevation that accompanies inertial cavitation 1606 breaks apart the sensitizer 908 generating free radicals that can react with other endogenous substrates to generate ROS 1608. Although ROS 1608 plays an important role is SDT, in some aspects sonodynamic therapy may be based on sonomechanical mechanisms. This conclusion was based on their observation that HP-sensitized cells can be sensitive to the acoustic wave 200 at intensities that were shown not to induce inertial cavitation.

In various aspects of the present disclosure, sonodynamic therapy may be carried out using one or more than one sensitizer 908. Such sensitizers 908 used in sonodynamic therapy may be selected from a variety of compounds. These compounds include, without limitation, porphyrins such as Photofrin, protoporphyrin IX precursor, xanthene-based sensitizers 908 such as Rose Bengal and derivatives thereof, acridine orange, methylene blue, curcumin, hypocrellin, indocyanine green, nanoparticle/microparticle sensitizer conjugates. Additional information on sonodynamic therapy may be found in Treating Cancer With Sonodynamic Therapy: A Review, David Costley et al., pages 107-117, received 17 Oct. 2014, accepted 23 Nov. 2014, published online 13 Jan. 2015, which is herein incorporated by reference in its entirety. In various aspects, the sonodynamic therapy techniques described in this disclosure may be applied to animals as well as humans. In one aspect, the sonodynamic therapy techniques described in this disclosure may be applied to mammals. In this regard, use of the term "patient" throughout this disclosure is intended to cover humans and animals alike.

In various aspects, the sonodynamic therapy techniques described in this disclosure may be adapted to other parts of the body. These other parts of the body may be accessed through natural orifice (mouth, nasal cavity, anus, vagina) or minimally invasive processes such as intravascular access. The sonodynamic therapy device may be specifically adapted to have a flexible, navigable catheter shaft to reach tumors in specific organs such as liver, stomach, breast, or lungs, for example. The sonodynamic therapy device may be adapted to wrap around the torso or limb and may be employed to treat osteosarcoma into the bone.

In various aspects, the sonodynamic therapy techniques described in this disclosure may be adapted for use with adjuvant therapies. The disclosed sonodynamic therapy techniques may be employed in other cancer therapies including chemotherapy, immunotherapy, radiotherapy, HIFU/hyperthermia. Further, the disclosed sonodynamic therapy techniques employ additional drugs which increase oxygen in the brain or increase oxygen in a brain tumor to a preferential oxygen concentration to provide an effective sonodynamic therapy. The disclosed sonodynamic therapy techniques may employ a sensitizer which is modified or encapsulated to effectively target a tumor. The disclosed sonodynamic therapy techniques may deliver 0 2 systematically with nose tubes. The disclosed sonodynamic therapy techniques may employ multiple sensitizers in conjunction and may include the introduction of gas bubbles into the tumor to oxygenate the tumor, create more cavitation, and provide a possible contrast mechanism for imaging.

In various aspects, the sonodynamic therapy techniques described in this disclosure may be adapted for use with ultrasound imaging. The process may include the addition of a contrast agent for ultrasound which goes to the tumor.

As used herein a processor or processing unit is an electronic circuit which performs operations on some external data source, usually memory or some other data stream. The term is used herein to refer to the central processor (central processing unit) in a system or computer systems (especially systems on a chip (SoCs)) that combine a number of specialized "processors."

As used herein, a system on a chip or system on chip (Soc or SOC) is an integrated circuit (also known as an "IC" or "chip") that integrates all components of a computer or other electronic systems. It may contain digital, analog, mixed-signal, and often radio-frequency functions-all on a single substrate. A Soc integrates a microcontroller (or microprocessor) with advanced peripherals like graphics processing unit (GPU), Wi-Fi module, or coprocessor. A Soc may or may not contain built-in memory.

As used herein, a microcontroller or controller is a system that integrates a microprocessor with peripheral circuits and memory. A microcontroller (or MCU for microcontroller unit) may be implemented as a small computer on a single integrated circuit. It may be similar to a Soc; an Soc may include a microcontroller as one of its components. A microcontroller may contain one or more core processing units (CPUs) along with memory and programmable input/output peripherals. Program memory in the form of Ferroelectric RAM, NOR flash or OTP ROM is also often included on chip, as well as a small amount of RAM. Microcontrollers may be employed for embedded applications, in contrast to the microprocessors used in personal computers or other general purpose applications consisting of various discrete chips.

As used herein, the term controller or microcontroller may be a stand-alone IC or chip device that interfaces with a peripheral device. This may be a link between two parts of a computer or a controller on an external device that manages the operation of (and connection with) that device.

Any of the processors or microcontrollers described herein, may be implemented by any single core or multicore processor such as those known under the trade name ARM Cortex by Texas Instruments. In one aspect, the processor may be an LM4F230H5QR ARM Cortex-M4F Processor Core, available from Texas Instruments, for example, comprising on-chip memory of 256 KB single-cycle flash memory, or other non-volatile memory, up to 40 MHz, a prefetch buffer to improve performance above 40 MHz, a 32 KB single-cycle serial random access memory (SRAM), internal read-only memory (ROM) loaded with StellarisWare® software, 2 KB electrically erasable programmable read-only memory (EEPROM), one or more pulse width modulation (PWM) modules, one or more quadrature encoder inputs (QEI) analog, one or more 12-bit Analog-to-Digital Converters (ADC) with 12 analog input channels, details of which are available for the product datasheet.

In one aspect, the processor may comprise a safety controller comprising two controller-based families such as TMS570 and RM4x known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

As used herein, the terms "component," "system," "module" and the like can refer to a computer-related entity, either hardware, a combination of hardware and software, software, or software in execution, in addition to electro-mechanical devices. For example, a component may be, but is not limited to being, a process running on a processor, a processor, an object, an executable, a thread of execution, a program, and/or a computer. By way of illustration, both an application running on computer and the computer can be a component. One or more components may reside within a process and/or thread of execution and a component may be localized on one computer and/or distributed between two or more computers. The word "exemplary" is used herein to mean serving as an example, instance, or illustration. Any aspect or design described herein as "exemplar" is not necessarily to be construed as preferred or advantageous over other aspects or designs.

As used herein, the term control circuit may be any stand alone or combination electronic circuit such as, for example, a processing unit, processor, microcontroller, microcontroller unit, controller, digital signal processor (DSP), programmable gate array (PGA), field PGA (FPGA), programmable logic device (PLD), system on chip (SoC), application specific integrated circuit (ASIC), graphics processing unit (GPU), and the like. According to various aspects, process flow diagrams described herein may be implemented by a digital device such as a control circuit.

Although the various aspects of the present disclosure describe instruction handling and distribution in the context of execution units and logic circuits, other aspects of the present disclosure can be accomplished by way of data and/or instructions stored on a machine-readable, tangible medium, which when performed by a machine cause the machine to perform functions consistent with at least one aspect. In one aspect, associated functions of the present disclosure are embodied in machine-executable instructions. The instructions can be used to cause a general-purpose or special-purpose processor that is programmed with the instructions to perform the steps of the functions described in the present disclosure. Aspects of the present disclosure may be provided as a computer program product or software which may include a machine or non-transitory computer-readable medium having stored thereon instructions which may be used to program a computer (or other electronic devices) to perform one or more operations according to aspects of the present disclosure. Alternatively, functions according to the present disclosure might be performed by specific hardware components that contain fixed-function logic for performing the functions, or by any combination of programmed computer components and fixed-function hardware components.

Instructions used to program logic to perform various disclosed aspects can be stored within a memory in the system, such as DRAM, cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, Compact Disc, Read-Only Memory (CD-ROMs), and magneto-optical disks, Read-Only Memory (ROMs), Random Access Memory (RAM), Erasable Programmable Read-Only Memory (EPROM), Electrically Erasable Programmable Read-Only Memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

Various examples have been described with reference to certain disclosed aspects. The various aspects are presented for purposes of illustration and not limitation. One skilled in the art will appreciate that various changes, adaptations, and modifications can be made without departing from the scope of the disclosure or the scope of the appended claims.

What is claimed is:

1. A method of producing ultrasound waves for sonodynamic therapy to treat tumor cells harboring a sonosensitizer, comprising:

coupling a sonodynamic therapy device to a skin surface over a treatment region with the tumor cells of a patient, the sonodynamic therapy device comprising:

an array of piezoelectric ultrasound transducer elements, wherein each of the piezoelectric ultrasound transducer elements comprises an emitting surface configured to emit an ultrasound wave, a controller, wherein the controller is coupled to the array of piezoelectric ultrasound transducer elements and the controller is configured to generate a plurality of signals for driving the piezoelectric ultrasound transducer elements and generating ultrasound waves, and a patient interface, wherein the patient interface is configured for conforming to the skin surface of the patient, driving the array of piezoelectric ultrasound transducer elements with the plurality of signals to activate the sonosensitizer in the treatment region of the patient, wherein the sonosensitizer comprises a porphyrin, wherein the plurality of signals comprises one or more frequencies in a range of 20 kHz to 2 MHz, wherein the plurality of signals comprises at least one selected from the group consisting of: a sine wave, a rectangular pulse, and a triangular pulse, wherein individual ones of the plurality of signals are configured to drive individual ones of the piezoelectric ultrasound transducer elements to emit the ultrasound waves to minimize a spatial variation of an acoustic intensity in the treatment region, wherein the controller uses an algorithm for the array of piezoelectric ultrasound transducer elements to provide the acoustic intensity in a range of 0.1 $W/cm^2$ to 50 $W/cm^2$, wherein the controller is configured to modulate the ultrasound waves with randomized phases, and wherein the patient interface comprises a cooling system placed between the array of piezoelectric ultrasound transducer elements and the treatment region, the cooling system comprising one or more cooling loops or channels and a flexible membrane configured to allow circulation of a coolant therein.

2. The method of claim 1, wherein the plurality of signals comprises one or more frequencies in a range of 650 kHz to 1 MHz.

3. The method of claim 1, wherein the plurality of signals comprises a modulated wave parameter configured to emit the ultrasound waves to damage the tumor cells in the treatment region.

4. The method of claim 1, wherein the controller uses the algorithm for the array of piezoelectric ultrasound transducer elements to provide the acoustic intensity in a range of 0.1 $W/cm^2$ to 20 $W/cm^2$.

5. The method of claim 1, wherein the plurality of signals is modulated by a duty cycle modulated drive signal configured to produce duty cycle modulated acoustic waves.

6. The method of claim 1, wherein the controller uses at least one in situ variable selected from the group consisting of: a tissue depth, a tissue volume, a skull thickness, and a temperature, and generates the ultrasound waves based on the at least one in situ variable.

7. The method of claim 1, wherein the plurality of signals is configured to drive each of the piezoelectric ultrasound transducer elements to produce high temporal peak acoustic intensities within the treatment region with a low temporal average acoustic intensity when activating the sonosensitizer.

8. The method of claim 1, wherein the driving the array of piezoelectric ultrasound transducer elements comprises driving multiple elements with multiple signals.

9. A method of producing ultrasound waves for sonodynamic therapy to treat tumor cells harboring a sonosensitizer, the method comprising:

coupling a sonodynamic therapy device to a skin surface over a treatment region of a patient, wherein the sonodynamic therapy device comprises:

a patient interface comprising a flexible membrane conforming to the skin surface of the patient and one or more cooling loops or channels, wherein the patient interface comprises at least one of a cap, a rigid shell, or a flexible shell, an array of piezoelectric ultrasound transducer elements, and a controller configured to generate a plurality of signals for driving the piezoelectric ultrasound transducer elements, wherein the controller drives the array of piezoelectric transducer elements at a plurality of frequencies in a range of 650 kHz to 2 MHz, wherein the controller uses an algorithm for the array of piezoelectric ultrasound transducer elements to provide an acoustic intensity in a range of 0.1 $W/cm^2$ to 50 $W/cm^2$, wherein the plurality of signals comprises at least one selected from the group consisting of: a sine wave, a rectangular pulse, and a triangular pulse, wherein each of the piezoelectric ultrasound transducer elements comprises an emitting surface configured to emit an ultrasound wave, driving the array of piezoelectric ultrasound transducer elements with the plurality of signals to activate the sonosensitizer in the treatment region, wherein the sonosensitizer comprises a porphyrin, circulating a coolant via the one or more cooling loops or channels, wherein individual ones of the plurality of signals are configured to drive individual ones of the piezoelectric ultrasound transducer elements to emit a plurality of ultrasound waves configured to minimize a spatial variation of the acoustic intensity in the treatment region, wherein the plurality of signals comprise a modulated wave parameter configured to modulate the plurality of ultrasound waves with randomized phases thereby promoting broad coverage across the treatment region, and wherein the plurality of signals are modulated by a duty cycle modulated drive signal configured to produce a low temporal average acoustic intensity within the treatment region.

10. The method of claim 9, wherein the controller drives the array of piezoelectric transducer elements at a plurality of frequencies in a range of 650 kHz to 1 MHz.

11. The method of claim 9, wherein the plurality of signals comprise a frequency modulated drive signal.

12. The method of claim 9, wherein the plurality of signals comprises at least one selected from the group consisting of: a sine wave, a rectangular pulse, and a triangular pulse.

13. The method of claim 9, wherein the sonodynamic therapy is configured to minimize a spatial variation of the acoustic intensity in the tumor cells.

14. The method of claim 9, wherein the sonodynamic therapy is configured to minimize a spatial variation of the acoustic intensity in the tumor cells, wherein the plurality of signals is selected from the group consisting of: duty cycle modulated drive signals and frequency modulated drive signals.

15. The method of claim 9, wherein the patient interface comprises at least one of the cap and the flexible shell.

16. The method of claim 9, further comprising administering a pro drug to the patient, wherein the pro drug comprises aminolevulinic acid (ALA).

17. The method of claim 16, wherein the ALA comprises 5-ALA.

18. The method of claim 9, wherein the porphyrin comprises protoporphyrin IX.

19. The method of claim 9, wherein the driving the array of piezoelectric ultrasound transducer elements occurs with the patient in a seated position on a chair.

20. A method of producing ultrasound waves for sonodynamic therapy to treat tumor cells harboring a sonosensitizer, comprising:

coupling a sonodynamic therapy device to a skin surface over a treatment region with the tumor cells of a patient, the sonodynamic therapy device comprising:

an array of piezoelectric ultrasound transducer elements, wherein each of the piezoelectric ultrasound transducer elements comprises an emitting surface configured to emit an ultrasound wave, a controller, wherein the controller is coupled to the array of piezoelectric ultrasound transducer elements and the controller is configured to generate a plurality of signals for driving the piezoelectric ultrasound transducer elements and generating ultrasound waves, and a patient interface, wherein the patient interface is configured for conforming to the skin surface of the patient, driving the array of piezoelectric ultrasound transducer elements with the plurality of signals to activate the sonosensitizer in the treatment region of the patient, wherein the sonosensitizer comprises a porphyrin, wherein the plurality of signals comprises one or more frequencies in a range of 20 kHz to 2 MHz, wherein individual ones of the plurality of signals are configured to drive individual ones of the piezoelectric ultrasound transducer elements to emit the ultrasound waves to minimize a spatial variation of an acoustic intensity in the treatment region, wherein the plurality of signals is configured to drive each of the piezoelectric ultrasound transducer elements to produce high temporal peak acoustic intensities within the treatment region with a low temporal average acoustic intensity when activating the sonosensitizer, wherein the controller uses an algorithm for the array of piezoelectric ultrasound transducer elements to provide the acoustic intensity in a range of 0.1 $W/cm^2$ to 50 $W/cm^2$;

wherein the controller is configured to modulate the ultrasound waves with randomized phases, and wherein the patient interface comprises a cooling system placed between the array of piezoelectric ultrasound transducer elements and the treatment region, the cooling system comprising one or more cooling loops or channels and a flexible membrane configured to allow circulation of a coolant therein.

21. A method of producing ultrasound waves for sonodynamic therapy to treat tumor cells harboring a sonosensitizer, the method comprising:

coupling a sonodynamic therapy device to a skin surface over a treatment region of a patient, wherein the sonodynamic therapy device comprises:

a patient interface comprising a flexible membrane conforming to the skin surface of the patient and one or more cooling loops or channels, wherein the patient interface comprises at least one of a cap, a rigid shell, or a flexible shell, an array of piezoelectric ultrasound transducer elements, and a controller configured to generate a plurality of signals for driving the piezoelectric ultrasound transducer elements, wherein the controller drives the array of piezoelectric transducer elements at a plurality of frequencies in a range of 650 kHz to 2 MHz, wherein the controller uses an algorithm for the array of piezoelectric ultrasound transducer elements to provide an acoustic intensity in a range of 0.1 $W/cm^2$ to 50 $W/cm^2$, wherein each of the piezoelectric ultrasound transducer elements comprises an emitting surface configured to emit an ultrasound wave, driving the array of piezoelectric ultrasound transducer elements with the plurality of signals to activate the sonosensitizer in the treatment region, wherein the sonosensitizer comprises a porphyrin, circulating a coolant via the one or more cooling loops or channels, wherein individual ones of the plurality of signals are configured to drive individual ones of the piezoelectric ultrasound transducer elements to emit a plurality of ultrasound waves configured to minimize a spatial variation of the acoustic intensity in the treatment region, wherein the plurality of signals comprise a modulated wave parameter configured to modulate the plurality of ultrasound waves with randomized phases thereby promoting broad coverage across the treatment region, and wherein the plurality of signals are modulated by a duty cycle modulated drive signal configured to produce high temporal peak acoustic intensities within the treatment region with a low temporal average acoustic intensity within the treatment region.

22. A method of producing ultrasound waves for sonodynamic therapy to treat tumor cells harboring a sonosensitizer, comprising:

coupling a sonodynamic therapy device to a skin surface over a treatment region with the tumor cells of a patient, the sonodynamic therapy device comprising:

an array of piezoelectric ultrasound transducer elements, wherein each of the piezoelectric ultrasound transducer elements comprises an emitting surface configured to emit an ultrasound wave, a controller, wherein the controller is coupled to the array of piezoelectric ultrasound transducer elements and the controller is configured to generate a plurality of signals for driving the piezoelectric ultrasound transducer elements and generating ultrasound waves, and a patient interface, wherein the patient interface is configured for conforming to the skin surface of the patient, driving the array of piezoelectric ultrasound transducer elements with the plurality of signals to activate the sonosensitizer in the treatment region of the patient, wherein the sonosensitizer comprises a porphyrin, wherein the plurality of signals comprises one or more frequencies in a range of 20 kHz to 2 MHz, wherein individual ones of the plurality of signals are configured to drive individual ones of the piezoelectric ultrasound transducer elements to emit the ultrasound waves to minimize a spatial variation of an acoustic intensity in the treatment region, wherein the controller uses an algorithm for the array of piezoelectric ultrasound transducer elements to provide the acoustic intensity in a range of 0.1 $W/cm^2$ to 50 $W/cm^2$;

wherein the controller uses at least one in situ variable selected from the group consisting of: a tissue depth, a tissue volume, a skull thickness, and a temperature, and generates the ultrasound waves based on the at least one in situ variable, wherein the controller is configured to modulate the ultrasound waves with randomized phases, and wherein the patient interface comprises a cooling system placed between the array of piezoelectric ultrasound transducer elements and the treatment region, the cooling system comprising one or more cooling loops or channels and a flexible membrane configured to allow circulation of a coolant therein.

23. A method of producing ultrasound waves for sonodynamic therapy to treat tumor cells harboring a sonosensitizer, the method comprising:

coupling a sonodynamic therapy device to a skin surface over a treatment region of a patient, wherein the sonodynamic therapy device comprises:

a patient interface comprising a flexible membrane conforming to the skin surface of the patient and one or more cooling loops or channels, wherein the patient interface comprises at least one of a cap, a rigid shell, or a flexible shell, an array of piezoelectric ultrasound transducer elements, and a controller configured to generate a plurality of signals for driving the piezoelectric ultrasound transducer elements, wherein the controller drives the array of piezoelectric transducer elements at a plurality of frequencies in a range of 650 kHz to 2 MHz, wherein the controller uses an algorithm for the array of piezoelectric ultrasound transducer elements to provide an acoustic intensity in a range of 0.1 $W/cm^2$ to 50 $W/cm^2$, wherein the controller uses at least one in situ variable selected from the group consisting of: a tissue depth, a tissue volume, a skull thickness, and a temperature, and generates the ultrasound waves based on the at least one in situ variable, wherein each of the piezoelectric ultrasound transducer elements comprises an emitting surface configured to emit an ultrasound wave, driving the array of piezoelectric ultrasound transducer elements with the plurality of signals to activate the sonosensitizer in the treatment region, wherein the sonosensitizer comprises a porphyrin, circulating a coolant via the one or more cooling loops or channels, wherein individual ones of the plurality of signals are configured to drive individual ones of the piezoelectric ultrasound transducer elements to emit a plurality of ultrasound waves configured to minimize a spatial variation of the acoustic intensity in the treatment region, wherein the plurality of signals comprise a modulated wave parameter configured to modulate the plurality of ultrasound waves with randomized phases thereby promoting broad coverage across the treatment region, and wherein the plurality of signals are modulated by a duty cycle modulated drive signal configured to produce a low temporal average acoustic intensity within the treatment region.

24. A method of producing ultrasound waves for sonodynamic therapy to treat tumor cells harboring a sonosensitizer, comprising:

coupling a sonodynamic therapy device to a skin surface over a treatment region with the tumor cells of a patient, the sonodynamic therapy device comprising:

an array of piezoelectric ultrasound transducer elements, wherein each of the piezoelectric ultrasound transducer elements comprises an emitting surface configured to emit an ultrasound wave, a controller, wherein the controller is coupled to the array of piezoelectric ultrasound transducer elements and the controller is configured to generate a plurality of signals for driving the piezoelectric ultrasound transducer elements and generating ultrasound waves, and a patient interface, wherein the patient interface is configured for conforming to the skin surface of the patient, driving the array of piezoelectric ultrasound transducer elements with the plurality of signals to activate the sonosensitizer in the treatment region of the patient, wherein the sonosensitizer comprises a porphyrin, wherein the plurality of signals comprises one or more frequencies in a range of 20 kHz to 2 MHz, wherein individual ones of the plurality of signals are configured to drive individual ones of the piezoelectric ultrasound transducer elements to emit the ultrasound waves to minimize a spatial variation of an acoustic intensity in the treatment region, wherein the controller uses an algorithm for the array of piezoelectric ultrasound transducer elements to provide the acoustic intensity in a range of 0.1 $W/cm^2$ to 50 $W/cm^2$;

wherein the controller is configured to modulate the ultrasound waves with randomized phases, and wherein the patient interface comprises a cooling system placed between the array of piezoelectric ultrasound transducer elements and the treatment region, the cooling system comprising one or more cooling loops or channels and a flexible membrane configured to allow circulation of a coolant therein, wherein the driving the array of piezoelectric ultrasound transducer elements occurs with the patient in a seated position on a chair.

25. A method of producing ultrasound waves for sonodynamic therapy to treat tumor cells harboring a sonosensitizer, the method comprising:

coupling a sonodynamic therapy device to a skin surface over a treatment region of a patient, wherein the sonodynamic therapy device comprises:

a patient interface comprising a flexible membrane conforming to the skin surface of the patient and one or more cooling loops or channels, wherein the patient interface comprises at least one of a cap, a rigid shell, or a flexible shell, an array of piezoelectric ultrasound transducer elements, and a controller configured to generate a plurality of signals for driving the piezoelectric ultrasound transducer elements, wherein the controller drives the array of piezoelectric transducer elements at a plurality of frequencies in a range of 650 kHz to 2 MHz, wherein the controller uses an algorithm for the array of piezoelectric ultrasound transducer elements to provide an acoustic intensity in a range of 0.1 $W/cm^2$ to 50 $W/cm^2$, wherein each of the piezoelectric ultrasound transducer elements comprises an emitting surface configured to emit an ultrasound wave, driving the array of piezoelectric ultrasound transducer elements with the plurality of signals to activate the sonosensitizer in the treatment region, wherein the sonosensitizer comprises a porphyrin, circulating a coolant via the one or more cooling loops or channels, wherein individual ones of the plurality of signals are configured to drive individual ones of the piezoelectric ultrasound transducer elements to emit a plurality of ultrasound waves configured to minimize a spatial variation of the acoustic intensity in the treatment region, wherein the plurality of signals comprise a modulated wave parameter configured to modulate the plurality of ultrasound waves with randomized phases thereby promoting broad coverage across the treatment region, and wherein the plurality of signals are modulated by a duty cycle modulated drive signal configured to produce a low temporal average acoustic intensity within the treatment region, wherein the driving the array of piezoelectric ultrasound transducer elements occurs with the patient in a seated position on a chair.

* * * * *